(12) United States Patent
Brewer et al.

(10) Patent No.: US 6,541,620 B1
(45) Date of Patent: *Apr. 1, 2003

(54) NUCLEIC ACIDS ENCODING TNF INHIBITOR AND METHOD OF PRODUCTION

(75) Inventors: Michael T. Brewer, Boulder, CO (US); Robert C. Thompson, Boulder, CO (US); Tadahiko Kohno, Louisville, CO (US)

(73) Assignee: Angen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/484,337

(22) Filed: Jun. 7, 1995

Related U.S. Application Data

(60) Division of application No. 08/375,242, filed on Jan. 19, 1995, now Pat. No. 6,143,866, which is a continuation-in-part of application No. 07/479,661, filed on Feb. 7, 1990, now abandoned, which is a continuation-in-part of application No. 07/381,080, filed on Jul. 18, 1989, now abandoned, which is a continuation-in-part of application No. 07/450,329, filed on Dec. 11, 1989, now abandoned.

(51) Int. Cl.[7] ............................................. C07H 21/00
(52) U.S. Cl. ..................................... 536/23.5; 435/69.1
(58) Field of Search .................. 435/69.1, 69.5, 435/320.1, 252.3, 325; 536/23.5

(56) References Cited

U.S. PATENT DOCUMENTS

| | | | |
|---|---|---|---|
| 4,179,337 A | * 12/1979 | Harris et al. ................. | 530/350 |
| 4,289,690 A | 9/1981 | Pestka et al. | |
| 4,560,649 A | 12/1985 | Saxena et al. | |
| 4,578,335 A | 3/1986 | Uradal et al. | |
| 4,609,546 A | * 9/1986 | Hiratani et al. ................. | 514/2 |
| 4,675,285 A | 6/1987 | Clark et al. | |
| 4,789,658 A | 12/1988 | Yoshimoto et al. | |
| 4,847,325 A | 7/1989 | Shadle et al. | |
| 4,902,502 A | 2/1990 | Nitecki et al. | |
| 4,904,584 A | 2/1990 | Shaw et al. | |
| 4,917,888 A | 4/1990 | Katre et al. | |
| 4,931,544 A | 6/1990 | Katre et al. | |
| 4,935,233 A | 6/1990 | Bell et al. | |
| 4,966,888 A | 10/1990 | Saxena et al. | |
| 5,089,261 A | 2/1992 | Nitecki et al. | |
| 5,116,964 A | 5/1992 | Capon et al. | |
| 5,136,021 A | 8/1992 | Dembinski et al. | |
| 5,153,265 A | 10/1992 | Shadle et al. | |
| 5,162,430 A | 11/1992 | Rhee et al. | |
| 5,166,322 A | 11/1992 | Shaw et al. | |
| 5,211,945 A | 5/1993 | Wallach et al. | |
| 5,214,131 A | 5/1993 | Sano et al. | |
| 5,252,714 A | 10/1993 | Harris et al. | |
| 5,344,915 A | 9/1994 | LeMaire et al. | |
| 5,359,037 A | 10/1994 | Wallach et al. | |
| 5,382,657 A | 1/1995 | Karasiewicz et al. | |
| 5,395,760 A | 3/1995 | Smith et al. | |
| 5,478,925 A | 12/1995 | Wallach et al. | |
| 5,512,544 A | 4/1996 | Wallach et al. | |
| 5,605,690 A | 2/1997 | Jacobs et al. | |
| 5,610,279 A | 3/1997 | Brockhaus et al. | |
| 5,695,953 A | * 12/1997 | Wallach et al. ............ | 435/69.1 |
| 5,808,029 A | 9/1998 | Brockhaus et al. | |
| 5,811,261 A | 9/1998 | Wallach et al. | |
| 6,143,866 A | * 11/2000 | Brewer et al. | |

FOREIGN PATENT DOCUMENTS

| | | |
|---|---|---|
| DE | 39 10 323 A1 | 10/1989 |
| DE | 3913101.7 | 10/1990 |
| DE | 03 920 282.8 | 1/1991 |
| EP | 0154316 | * 3/1985 |
| EP | 0 154 316 A2 | 9/1985 |
| EP | 0 162 699 | 11/1985 |
| EP | 0 094 844 | 5/1986 |
| EP | 0 225 579 A3 | 6/1987 |
| EP | 0 247 860 A2 | 12/1987 |
| EP | 0 259 863 A2 | 3/1988 |
| EP | 0308378 | * 3/1989 |
| EP | 0 154 316 B1 | 9/1989 |
| EP | 0 334 165 A2 | 9/1989 |
| EP | 0 393 438 A2 | 10/1990 |
| EP | 0 398 327 A1 | 11/1990 |
| EP | 0 417 563 A2 | 3/1991 |
| EP | 0 418 014 A1 | 3/1991 |
| EP | 0 422 339 | 4/1991 |
| EP | 0 433 900 A1 | 6/1991 |
| EP | 0 512 528 A2 | 11/1992 |
| EP | 0 526 905 A2 | 2/1993 |
| GB | 2 218 101 | 11/1989 |
| GB | 2 246 569 A | 2/1992 |
| WO | WO 87/00056 | 1/1987 |
| WO | WO 88/00837 | 3/1988 |
| WO | WO 90/13575 | 11/1990 |
| WO | WO 91/03553 | 3/1991 |
| WO | WO 92/01474 | 2/1992 |
| WO | WO 92/07076 | 4/1992 |
| WO | WO 92/13095 | 8/1992 |
| WO | WO 92/15682 | 9/1992 |
| WO | WO 92/16221 | 10/1992 |
| WO | WO 94/06476 | 3/1994 |
| WO | WO 95/06058 | 3/1995 |

OTHER PUBLICATIONS

Yamasaki et al, *Agric. Biol. Chem* 52(8) 1988, p. 2125–2127.*

Abuchowski et al., "Effect of covalent attachment of polyethylene glycol on immunogenicity and circulating life of bovine liver catalase," *J. Biol. Chem.* 252(11):3582–86 (1977).

(List continued on next page.)

*Primary Examiner*—Lorraine Spector
*Assistant Examiner*—Eliane Lazar-Wesley
(74) *Attorney, Agent, or Firm*—McDonnell Boehnen Hulbert & Berghoff

(57) ABSTRACT

The present invention provides nucleic acid molecules encoding a 30kDa TNF inhibitor or a fragment thereof having at least one non-native cysteine residue at the N-terminus, C-terminus, residue 14, or residue 15.

2 Claims, 61 Drawing Sheets

OTHER PUBLICATIONS

Figure 1:
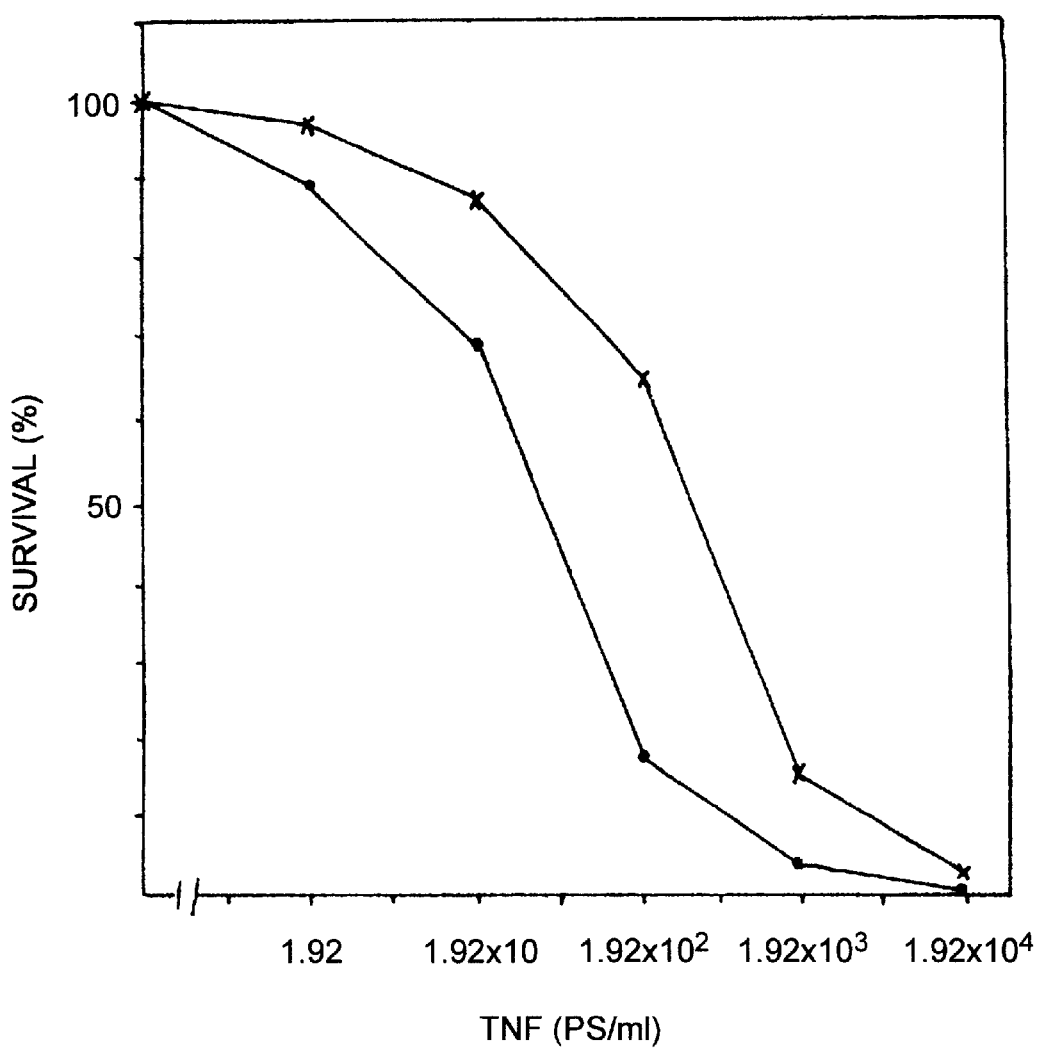

Beutler and Cerami, "The biology of cachectin/TNF—a primary mediator of the host response," *Annu. Rev. Immunol.* 7:625–55 (1989).

Davis et al., "Soluble, Nonantigenic Polyethylene Glycol–Bound Enzymes," in *Biomedical Polymers: Polymeric Materials and Pharmaceuticals for Biomedical Use* 441–451 (Goldberg et al. eds., Academic Press) (1980).

Glass et al., "4–Phenoxy–3,5–Dinitobenzoylpolyethyleneglycol: Reversible Attachment of Cysteine–Containing Polypeptides to Polymers in Aqueous Solutions," *Biopolymers* 18:383–92 (1979).

Harris, "Laboratory Synthesis of Polyethylene Glycol Derivatives," *Rev. Macromol. Chem. Phys.* C25(3):325–73 (1985).

Harris et al., "Synthesis and Characterization of Poly(ethylene Glycol) Derivatives," *J. Polymer Sci.* 22:341–52 (1984).

Suzuki et al., "Physicochemical and biological properties of poly(ethylene glycol)–coupled immunoglobulin G," Biochim. Biophys. Acta 788(2):248–55 (1984).

Anderson et al., "Quantative Filter Hybridisation," *Nucleic Acid Hybridization: A Practical Approach*, Hawes et al., (ed.), pp. 73–111 (1985).

Aggarwal et al., "Characterization of Receptors for Human Tumour Necrosis Factor and Their Regulation by y–Interferon," *Nature* 318:665–667 (1985).

Baglioni et al., "Binding of Human Tumor Necrosis Factor to High Affinity Receptors on HeLa and Lymphoblastoid Cells Sensitive to Growth Inhibition," *J. Biol. Chem.* 260(25):13395–13397 (1985).

Bakouche et al., "Plasma Membrane–Associated Tumor Necrosis Factor, A Non–Integral Membrane Protein Possibly Bound to Its Own Receptor," *J. Immunol.* 140:1142–1147 (1988).

Beutler et al., "Passive Immunization against Cachectin/Tumor Necrosis Factor Protects Mice from Lethal Effect of Endotoxin," *Science* 229:869–871 (1985).

Binkert et al., "Cloning, Sequence Analysis and Expression of a cDNA Encoding a Novel Insulin–like Growth Factor Binding Protein (IGFBP–2)," *The EMBO J.* 8(9):2497–2502 (1989).

Bowie et al., "Deciphering the Message in Protein Sequences: Tolerance to Amino Acid Substitutions," *Science*, 247:1306–1310 (1990).

Brennan et al., Lancet, vol. 2 (8657), pp. 244–247 (1989).

Brockhaus et al., "Identification of Two Types of Tumor Necrosis Factor Receptors on Human Cell Lines by Monoclonal Antibodies," *Proc. Natl. Acad. Sci. USA* 87:3127–3131 (1990).

Capaldi et al., "Changes in Order of Migration of Polypeptides in Complex III and Cytochrome c Oxidase under Different Conditions of SDS Polyacrylamide Gel Electrophoresis," *Biochem. & Biophys. Res. Comm.* 74(2):425–433 (1977).

Carlino et al., "Use *of a Sensitive Receptor Binding Assay to Discriminate Between Full–Length and Truncated Human Recombinant TNF Proteins*",*J. Biol. Chem.* 262(3):958–961 (1987).

Colletti et al., "The Production of Tumor Necrosis Factor Alpha and the Development of a Pulmonary Capillary Injury Following Hepatic Ischemia/Reperfusion," *Transplantation* 49(2):268–272 (1990).

Creasey et al., "A High Molecular Weight Component of the Human Tumor Necrosis Factor Receptor is Associated with Cytotoxicity," *Proc. Natl. Acad. Sci. USA* 84:3293–3297 (1987).

Dayer et al., "Purification and Characterization of Human Tumor Necrosis Factor α Inhibitor," *Chemical Abstracts* 113(38760n):454 (1990).

Dembic et al., "Two Human TNF Receptors Have Similar Extracellular, But Distinct Intracellular, Domain Sequences," *Cytokine* 2(4):231–237 (1990).

Engelmann et al., "A Tumor Necrosis Factor–Binding Protein Purified to Homogeneity from Human Urine Protects Cells from Tumor Necrosis Factor Toxicity," *J. Biol. Chem.* 264(20):11974–11980 (1989).

Engelmann et al., "Antibodies to a Soluble Form of a Tumor Necrosis Factor (TNF) Receptor Have TNF–Like Activity," *J. Biol. Chem.* 265(24):14497–14504 (1990).

Englemann et al., "Two Tumor Necrosis Factor–Binding Proteins Purified From Human Urine," *J. Biol. Chem.* 265(3):1531–1536 (1990).

Espevik et al., "Characterization of Binding and Biological Effects Monoclonal Antibodies Against a Human Tumor Necrosis Factor Receptor," *J. Exp. Med.* 171:415–426 (1990).

Evans et al., "The Steroid and Thyroid Hormone Receptor Superfamily," *Science* 240:889–895 (1988).

Frohman et al., "Rapid production of full–length cDNAs from rare transcripts: Amplification using a single gene–specific oligonucleotide primer," *Proc. Natl. Acad. Sci. USA* 85:8998–9002 (1988).

Gatanaga et al., "Purification and Characterization of an Inhibitor (Soluble Tumor Necrosis Factor Receptor) for Tumor Necrosis Factor and Lymphotoxin Obtained from the Serum Ultrafiltrates of Human Cancer Patients," *Proc. Natl. Acad. Sci. USA* 87:8781–8784 (1990).

Goodson et al., "Site–Directed Pegylation of Recombinant Interleukin–2 At Its Glycosylation Site," *Bio Technology* 8:343–346 (1990).

Goodwin et al., "Molecular Cloning and Expression of the Type 1 and Type 2 Murine Receptors for Tumor Necrosis Factor," *Molecular and Cell Biology* 11(6):3020–3026 (1991).

Gray et al., "Cloning of Human Tumor Necrosis Factor (TNF) Receptor cDNA and Expression of Recombinant soluble TNF–Binding Protein," *Proc. Natl. Acad. Sci. USA* 87(19):7380–7384 (1990).

Grizzard et al., "Affinity–Labeled Somatomedin–C Receptors and Binding Proteins From the Human Fetus," *J. Clin. Endocrinol. & Metab.* 58(3):535–543 (1984).

Hale et al., "Cytokines and Their Receptors: From Clonal to Clinical Investigation, Demonstration of In Vitro and In Vivo Efficacy of Two Biologically Active Human Soluble TNF Receptors Expressed in *E. Coli*," *J. Cell. Biochem- .Suppl..* 15F:113 (1991).

Hass et al., "Characterization of Specific High Affinity Receptors for Human Tumor Necrosis Factor on Mouse Fibroblasts," *J. Biol. Chem.* 260(22):12214–12218 (1985).

Hatakeyama et al., "Interleukin–2 Receptor β Chain Gene: Generation of Three Receptor Forms by Cloned Human α and β Chain cDNA's," *Science* 244:551 (1989).

Hauser et al., "Cytokine Accumulations in CSF of Multiple Sclerosis Patients: Frequent Detection of Interleukin–1 and Tumor Necrosis Factor but not Interleukin–6," *Neurology* 40:1735–1739 (1990).

Heller et al., "Amplified Expression of Tumor Necrosis Factor Receptor in Cells Transfected with Epstein–Barr Virus Shuttle Vector cDNA Libraries," *J. Biol. Chem.* 265(10):5708–5717 (1990).

Heller et al., "Complementary DNA Cloning of a Receptor for Tumor Necrosis Factor and Demonstration of a Shed From of the Receptor," *Proc. Natl. Acad. Sci. USA* 87:6151–6155 (1990).

Himmler et al., "Molecular Cloning & Expression of Human & Rat Tumor Necrosis Factor Receptor Chain (p60) and Its Soluble Derivative, Tumor Necrosis Factor–Binding Protein," *DNA and Cell Biology* 9(10):705–715 (1990).

Hofman et al., "Tumor Necrosis Factor Identified in Multiple Sclerosis Brain," *J. Exp. Med.* 170:607–612 (1989).

Hohmann et al., "Two Different Cell Types Have Different Major Receptors for Human Tumor Necrosis Factor (TNF alpha)," *J. Biol. Chem.* 264(25):14927–14934 (1989).

Israel et al., "Binding of Human TNF–alpha to High–Affinity Cell Surface Receptor: Effect of IFN," *Immunol. Lett.* 12:217–224 (1986).

Kasukabe et al., "Purification of a Novel Growth Inhibitory Factor for Partially Differentiated Myeloid Leukemic Cells," *J. Biol. Chem.* 263(11):5431–5435 (1988).

Kohno et al., "A Second Tumor Necrosis Factor Receptor Gene Product Can Shed a Naturally Occurring Tumor Necrosis Factor Inhibitor," *Proc. Natl. Acad. Sci. USA* 87:8331–8335 (1990).

Kull et al., "Cellular Receptors for $^{125}$I–Labeled Tumor Necrosis Factor: Specific Binding, Affinity Labeling, and Relationship to Sensitivity," *Proc. Natl. Acad. Sci. USA* 82:5756–5760 (1985).

Lantz et al., "Characterization In Vitro of a Human Tumor Necrosis Factor–Binding Protein," *J. Clin. Invest.* 86(5):1396–1402 (1990).

Le et al., "Tumor Necrosis Factor and Interleukin 1: Cytokines with Multiple Overlapping Biological Activities," *Lab Investigation* 56(3):234–248 (1987).

Lee et al., "Generation of cDNA Probes Directed by Amino Acid Sequence: Cloning of Urate Oxidase," *Science* 239:1288–1291 (1988).

Lehmann et al., "Demonstration of Membrane Receptors for Human Natural and Recombinant $^{125}$I–Labeled Tumor Necrosis Factor on HeLa Cell Clones and Their Role in Tumor Cell Sensitivity," *Eur. J. Biochem.* 158:1–5 (1986).

Leung et al., "Growth Hormone Receptor and Serum Binding Protein: Purification, Cloning and Expression," *Nature* 330:537–543 (1987).

Liao et al., "Characterization of a Human Interleukin 1 Inhibitor," *J. Immunol.* 134(6):3882–3886 (1985).

Liao et al., "Identification of a Specific Interleukin 1 Inhibitor in the Urine of Febrile Patients," *J. Exp. Med.* 159:126–136 (1984).

Liblau et al., "Tumor Necrosis Factor–α and Disease Progression in Multiple Sclerosis," *New Engl. J. Med.* 326(4):272–273 (1992).

Lindvall et al., "Modulation of the Constitutive Gene Expression of the 55 KD Tumor Necrosis Factor Receptor in Hematopoietic Cells," *Biochem. & Biophys. Res. Comm.* 172(2)557–563 (1990).

Loetscher et al., "Molecular Cloning and Expression of the Human 55kd TNF Necrosis Factor Receptor," *Cell* 61:351–359 (1990).

Loetscher et al., "Recombinant 55–kDa Tumor Necrosis Factor (TNF) Receptor," *J. Biol. Chem.* 266(27):18324–18329 (1991).

March et al., "Cloning, Sequence and Expression of Two Distinct Human Interleukin–1 Complementary DNAs," *Nature* 315:641–647 (1985).

Neda, Hiroshi, "Analysis of the Tumor Necrosis Factor (TNF) Receptor of Various Tumor Cells," *Tumor Necrosis Factor, (TNF) Receptor* 56(2):305–317 (1987). (Abstract in English).

Nexo et al., "Lectino–Agarose Immobilization, a New Method for Detecting Soluble Membrane Receptors," *J. Biol. Chem.* 254(18):8740–8743 (1979).

Nophar et al., "Soluble forms of tumor necrosis factor receptors (TNF–Rs). The cDNA for the type I TNF–R, cloned using amino acid sequence data of its soluble form, encodes both the cell surface and a soluble form of the receptor," *The EMBO J.* 9(10):3269–3278 (1990).

Novick et al., "Soluble Cytokine Receptors are Present in Normal Human Urine," *J. Exp. Med.* 170:1409–1414 (1989).

Novick et al, "Soluble Cytokine Receptors are Present in Normal Human Urine," *The Physiological and Pathological Effects of Cytokines*, pp. 413–421 (1990).

Novick et al., "Purification of Soluble Cytokine Receptors from Normal Human Urine by Ligand–Affinity and Immunoaffinity Chromatography," *J. Chromatog.* 510:331–337 (1990).

Olsson et al., "Isolation and Characterization of a Tumor Necrosis Factor Binding Protein from Urine," *Eur. J. Haematology* 42(3):270–275 (1989).

Peetre et al., "A Tumor Necrosis Factor Binding Protein is Present in Human Biological Fluids," *Eur. J. Haematology* 41:414–419 (1988).

Peppel et al., "A Tumor Necrosis Factor (TNF) Receptor–IgG Heavy Chain Chimeric Protein as a Bivalent Antagonist of TNF Activity," *J. Exp. Med.* 174:1483–1489 (1991).

Piguet et al., "Tumor Necrosis Factor/Cachectin Plays a Key Role in Bleomycin–Induced Pneumopathy and Fibrosis," *J. Exp. Med.* 170:655–663 (1989).

Powell et al., "Lymphotoxin and Tumor Necrosis Factor–alpha Production by Myelin basic Protein–Specific T Cell Clones Correlates With Encephalitogenicity," *International Immunology* 2(6):539–544 (1990).

Rhein et al., "Another Sepsis Drug Down—Immunex[1] TNF Receptor," Biotechnology *Newswatch*, pp. 1, 3(Monday, Oct. 4, 1993).

Ruddle et al., "An Antibody to Lymphotoxin and Tumor Necrosis Factor Prevents Transfer of Experimental Allergic Encephalomyelitis," *J. Exp. Med.* 172:1193–1200 (1990).

Schall et al., "Molecular Cloning and Expression of a Receptor for Human Tumor Necrosis Factor," *Cell* 61:361–370 (1990).

Scheurich et al., "Quantification and Characterization of High–Affinity Membrane Receptors for Tumor Necrosis Factor on Human Leukemic Cell Lines," *Int. J. Cancer* 38(1):127–133 (1986).

Seckinger et al., "A Human Inhibitor of Tumor Necrosis Factor Alpha," *J. Exp. Med.* 167:1511–1516 (1988).

Seckinger et al., "A Urine Inhibitor of Interleukin 1 Activity Affects Both Interleukin 1 α and 1 β But Not Tumor Necrosis Factor α," *J. Immunol.* 139(5):1541–1545 (1987).

Seckinger et al., "Characterization of a Tumor Necrosis Factor α (TNF–α) Inhibitor: Evidence of Immunological Cross–Reactivity with the TNF Receptor," *Proc. Natl. Acad. Sci. USA* 87:5188–5192 (1990).

Seckinger et al., "A Urine Inhibitor of Interleukin 1 Activity That Blocks Ligand Binding," *J. Immunol.* 139(5):1546–1549 (1987).

Seckinger et al., "Purification and Biologic Characterization of a Specific Tumor Necrosis Factor α Inhibitor," *J. Biol. Chem.* 264(20):11966–11973 (1989).

Selmaj et al., "Proliferation of Astrocytes In Vitro In Response to Cytokines: A Primary Role for Tumor Necrosis Factor," *J. Immunol.* 144(1):129–135 (1990).

Selmaj et al., "Tumor Necrosis Factor Mediates Myelin and Oligodendrocyte Damage In Vitro," *Annals of Neurology* 23(4):339–346 (1988).

Smith et al., "A Receptor for Tumor Necrosis Factor Defines an Unusual Family of Cellular and Viral Proteins," *Science* 248:1019–1023 (1990).

Smith et al., "Species Specificity of Human and Murine Tumor Necrosis Factor," *J. Biol. Chem.* 261(32):14871–14874 (1986).

Socher et al., "Antibodies against amino acids 1–15 of tumor necrosis factor block its binding cell–surface receptor," *Proc. Natl. Acad. Sci. USA* 84:8829–8833 (1987).

Spinas et al., "Induction of Plasma Inhibitors of Interleukin 1 and TNF–Alpha Activity by Endotoxin Administration to Normal Humans," *Am. J. Physiol.* 259:R993–R997 (1990).

Stauber et al., "Human Tumor Necrosis Factor–alpha Receptor," *J. Biol. Chem.* 263(35):19098–19104 (1988).

Stauber et al., "Characterization and Affinity Cross–Linking of Receptors for Human Recombinant Lymphotoxin (Tumor Necrosis Factor–Beta) on a Human Histiocytic Lymphoma Cell Line U–937," *J. Biol. Chem.* 264(6):3573–3576 (1989).

Suffys et al., "Involvement of a Serine Protease in Tumour–Necrosis–Factor–Mediated Cytotoxicity," *Eur. J. Biochem.* 178:257–265 (1988).

Suggs et al., "Use of Synthetic Oligonucleotides as Hybridization Probes: Isolation of Cloned cDNA Sequences for Human β2–Microglobulin," *Proc. Natl. Acad. Sci. USA* 78(11):6613–6617 (1981).

The Cytokine Factsbook, Callard (ed.), Academic Press Inc., San Diego, CA., pp. 244–246 (1994).

Tracey et al., "Anti–Cachectin/TNF Monoclonal Antibodies Prevent Septic Shock During Lethal Bacteraemia," *Nature* 330:662–664 (1987).

Tracey et al., "Cachectin/Tumor Necrosis Factor Induces Cachexia, Anemia, and Inflammation," *J. Exp. Med.* 167:1211–1227 (1988).

Tracey et al., "Metabolic Effects of Cachectin/Tumor Necorsis Factor Are Modified by Site of Production," *J. Clin. Invest.* 86:2014–2024 (1990).

Tracey et al., "Physiological responses to cachectin," *Tumor necrosis factor and related cytotoxins. Wiley, Chichester (Ciba Foundation Symposium 131)*, pp. 88–108 (1987).

Tsujimoto et al., "Characterization and Affinity Crosslinking of Receptors for Tumor Necrosis Factor on Human Cells," *Archives of Biochem. & Biophys.* 249(2):563–568 (1986).

Unglaub et al., "Downregulation of Tumor Necrosis Factor (TNF) Sensitivity Via Modulation of TNF Binding Capacity by Protein Kinase C Activators," *J. Exp. Med.* 166:1788–1797 (1987).

Vilcek et al., "Tumor Necrosis Factor: Receptor Binding and Mitogenic Action in Fibroblasts," *J. Cell. Physio. Supplement* 5:57–61 (1987).

Vitt et al., "Biological and Structural Characterization of the Tumor Necrosis Factor Receptor on Multiple Cell Types: Relationship to Function," *Fed. Proc. 78th Annual meeting of the American Society of Biological Chemists* 46(6):2117 (1987).

Wallach et al., "Mechanisms Which Take Part in Regulation of the Response to Tumor Necrosis Factor," *Lymphokine Research* 8(3):359–363 (1989).

Wallach, David, "Preparations of Lymphotoxin Induce Resistance to Their Own Cytotoxic Effect," *J. Immunol.* 132(5):2464–2469 (1984).

Wallach et al., "Regulation of the Response to Tumor Factor," Bonavida, Gifford, Kirchner, Old (eds), *Tumor Necrosis Factor/Cachectin and Related Cytokines Int. Conf. Tumor Necrosis Factor and Related Cytotoxins, Heidelberg* 1987, pp. 134–147 (1988).

Walsh et al., "Isolation and Purification of ILS, an Interleukin 1 Inhibitor Produced by Human Gingival Epithelial Cells," *Clin. Exp. Immunol.* 68:366–374 (1987).

Weber et al., "Production of an Epidermal Growth Factor Receptor–Related Protein," *Science* 224:294–297 (1984).

Yoshie et al., "Binding and Crosslinking of [125]I–Labeled Recombinant Human Tumor Necrosis Factor to Cell Surface Receptors," *J. Biochem.* 100:531–541 (1986).

Zeigler, Elizabeth J., "Tumor Necrosis Factor in Humans," *New Engl. J. Med.* 318(23):1533–1535 (1988).

* cited by examiner

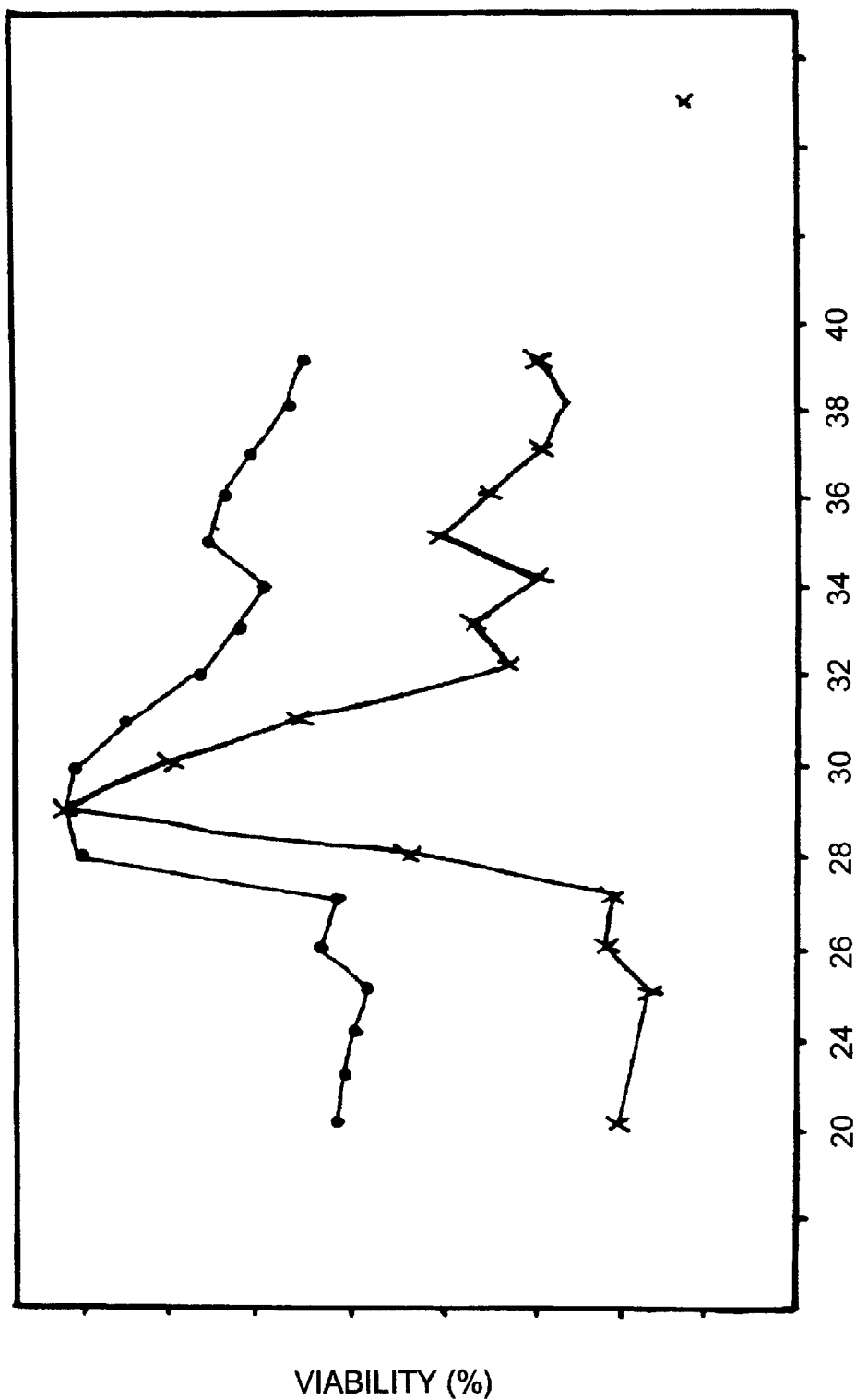

```
CATGCCTGCA GGTCGACTCT AGAGGATCTG GGGCCTACTA GCTTTGAGTT GAGGGAACAA AAATGAACAC
           80         90         100        110        120        130        140

ACAGGACAAC TAGAGAACAA TTAAGCATCA GATTGTATGC CCCAACTGTC TAAGTTTCAA GGAAGAACTC
           150        160        170        180        190        200        210

TAAACTTAGT GAGTGGCGTG GCCTGGGCGG AATGTTTCAC TGAGGAAGGA CTTGAGCCAG GGAAGTTTTA
           220        230        240        250        260        270        280

GATCTGCTAC CCCTAAGCTT CCCATCCCTC CCTCTCTTGA TGGTGTCTCC TCTATCTGAT TCTTCCCCAG
           289        298        307        316        325        334
```

| GTG | CTC | CTG | GAG | CTG | TTG | GTG | GGA | ATA | TAC | CCC | TCA | GGG | GTT | ATT | GGA | CTG | GTC |
|-----|-----|-----|-----|-----|-----|-----|-----|-----|-----|-----|-----|-----|-----|-----|-----|-----|-----|
| Val | Leu | Leu | Glu | Leu | Leu | Val | Gly | Ile | Tyr | Pro | Ser | Gly | Val | Ile | Gly | Leu | Val |

343                                    361                                    379                                    388

| CCT | CAC | CTA | GGG | GAC | AGG | GAG | AAG | AGA | GAT | AGT | GTG | TGT | CCC | CAA | GGA | AAA | TAT |
|-----|-----|-----|-----|-----|-----|-----|-----|-----|-----|-----|-----|-----|-----|-----|-----|-----|-----|
| Pro | His | Leu | Gly | Asp | Arg | Glu | Lys | Arg | Asp | Ser | Val | Cys | Pro | Gln | Gly | Lys | Tyr |

FIG. 13B

```
        397         406         415         424         433         444
ATC CAC CCT CAA AAT AAT TCG ATT TGC TGT ACC AAG TGC CAC AAA G  GTAGGGCAA
Ile His Pro Gln Asn Asn Ser Ile Cys Cys Thr Lys Cys His Lys Ala 454         464         474         484         494         504         514
GTGGAAACGG TGAATGCCCT CAGGTCTGGG GTGCTGCTTC TTTCTCTGCT TCTTCCAGTT GTTCTTCCCT 524         534         544         554         564         574         584
AACTTTGCTG TCTCTCCTGG GCTGGGATTT TCTCCCTCCC TCCTCTCCTA GAGACTTCAG GGAATCGGCC 594         604         614         624         634         644         654
CTGGCTGTTG TCCCTAGCAT GGGGCTCCTT CCTTGTGTTC TCACCCGCAG CCTAACTCTG CGGCCCCATT 664        673         682         691          700
CA  CA GGA ACC TAC TTG TAC AAT GAC TGT CCA GGC CCG GGG CAG GAT ACG GAC
    Gly Thr Tyr Leu Tyr Asn Asp Cys Pro Gly Pro Gly Gln Asp Thr Asp
```

FIG. 13C

```
709         718         727         736         745         754
TGC AGG GAG TGT GAG AGC GGC TCC TTC ACC GCT TCA GAA AAC CAC CTC AGA CAC
Cys Arg Glu Cys Glu Ser Gly Ser Phe Thr Ala Ser Glu Asn His Leu Arg His 763         772         781         797         807         817
TGC CTC AGC TGC TCC AAA TGC CGA AAG GGTGAGTGTG CACAGGCAGG AGAGTCAGGC
Cys Leu Ser Cys Ser Lys Cys Arg Lys 827        837        847        857        867        877        887
GGGTCTTGAG TGGTGTGTGG GTGCCTGTCT ATGTGCAGGC TGGTGGGTGT GGGCAGGAAG GTGTGTGTTT 897        907        917        927        937        947        957
TGGTGGGACA CTGCATGGAT GTGAGTGTGT ATTACAGAGA CACACACTTA GGGGTATGTC AGGAAGGGGA 967        977        987        997        1007       1016
TGCAGGGACA GGAGGATGCA GGACTCATAC CCCATCTTCT CCCCTCACCA GAA ATG GGT CAG
                                                        Glu MET Gly Gln

1025
GTG GAG ATC
Val Glu Ile
```

FIG. 14

```
  1         10         20         30         40         50         60         70         80
DSVCPQGKYIHPQNNSICCTKCHKGTYLYNDCPGPGQDTDCRECESGSFTASENHLRHCLSCSKCRKEMGQVEISSCTVDRDT
 90
VCGCRKN

KQNTVCTCHAGFFLRENECVSC

LECTKLCLPQIEN
```

FIG. 19

```
Asp Ser Val Cys Pro Gln Gly Lys Tyr Ile His Pro Gln Asn Asn Ser Ile Cys Cys Thr
                                                                              20
Lys Cys His Lys Gly Thr Tyr Leu Tyr Asn Asp Cys Pro Gly Pro Gly Gln Asp Thr Asp
                                                                              40
Cys Arg Glu Cys Glu Ser Gly Ser Phe Thr Ala Ser Glu Asn His Leu Arg His Cys Leu
                                                                              60
Ser Cys Ser Lys Cys Arg Lys Glu Met Gly Gln Val Glu Ile Ser Ser Cys Thr Val Asp
                                                                              80
Arg Asp Thr Val Cys Gly Cys Arg Lys Asn Gln Tyr Arg His Tyr Trp Ser Glu Asn Leu
                                                                             100
Phe Gln Cys Phe Asn Cys Ser Leu Cys Leu Asn Gly Thr Val His Leu Ser Cys Gln Glu
                                                                             120
Lys Gln Asn Thr Val Cys Thr Cys His Ala Gly Phe Phe Leu Arg Glu Asn Glu Cys Val
                                                                             140
Ser Cys Ser Asn Cys Lys Lys Ser Leu Glu Cys Thr Lys Leu Cys Leu Pro Gln Ile Glu
                                                                             160
Asn
```

FIG. 20A

```
                             297             306
                         |GAT AGT GTG TGT CCC CAA
                         |Asp Ser Val Cys Pro Gln
                315          324          333          342          351             360
|GGA AAA TAT ATC CAC CCT CAA AAT TCG ATT TGC TGT ACC AAG TGC CAC AAA
|Gly Lys Tyr Ile His Pro Gln Asn Ser Ile Cys Cys Thr Lys Cys His Lys
                369          378          387          396          405             414
|GGA ACC TAC TTG TAC AAT GAC TGT CCA GGC CCG GGG CAG GAT ACG GAC TGC AGG
|Gly Thr Tyr Leu Tyr Asn Asp Cys Pro Gly Pro Gly Gln Asp Thr Asp Cys Arg
                423          432          441          450          459             468
|GAG TGT GAG AGC GGC TCC TTC ACC GCT TCA GAA AAC CAC CTC AGA CAC TGC CTC
|Glu Cys Glu Ser Gly Ser Phe Thr Ala Ser Glu Asn His Leu Arg His Cys Leu
                477          486          495          504          513             522
|AGC TGC TCC AAA TGC CGA AAG GAA ATG GGT CAG GTG GAG ATC TCT TGC ACA
|Ser Cys Ser Lys Cys Arg Lys Glu MET Gly Gln Val Glu Ile Ser Cys Thr
```

FIG. 20B

```
      531       540       549       558       567       576
GTG   GAC   CGG   GAC   ACC   GTG   TGT   GGC   TGC   AGG   AAG   AAC   CAG   TAC   CGG   CAT   TAT   TGG
Val   Asp   Arg   Asp   Thr   Val   Cys   Gly   Cys   Arg   Lys   Asn   Gln   Tyr   Arg   His   Tyr   Trp
                      585                       594                       603                       612                       621                       630
AGT   GAA   AAC   CTT   TTC   CAG   TGC   TTC   AAT   TGC   AGC   CTC   TGC   CTC   AAT   GGG   ACC   GTG
Ser   Glu   Asn   Leu   Phe   Gln   Cys   Phe   Asn   Cys   Ser   Leu   Cys   Leu   Asn   Gly   Thr   Val
                      639                       648                       657                       666                       675                       684
CAC   CTC   TCC   TGC   CAG   GAG   AAA   CAG   AAC   ACC   GTG   TGC   ACC   TGC   CAT   GCA   GGT   TTC
His   Leu   Ser   Cys   Gln   Glu   Lys   Gln   Asn   Thr   Val   Cys   Thr   Cys   His   Ala   Gly   Phe
                      693                       702                       711                       720                       729                       738
TTT   CTA   AGA   GAA   AAC   GAG   TGT   GTC   TCC   TGT   AGT   AAC   TGT   AAG   AAA   AGC   CTG   GAG
Phe   Leu   Arg   Glu   Asn   Glu   Cys   Val   Ser   Cys   Ser   Asn   Cys   Lys   Lys   Ser   Leu   Glu
                      747                       756                       765
TGC   ACG   AAG   TTG   TGC   CTA   CCC   CAG   ATT   GAG   AAT
Cys   Thr   Lys   Leu   Cys   Leu   Pro   Gln   Ile   Glu   Asn
```

FIG. 21A

```
         10          20          30          40          50          60          70
GATCACTGGG ACCAGGCCGT GATCTCTATG CCCGAGTCTC AACCCTCAAC TGTCACCCCA AGGCACTTGG 80          90         100         110         120         130         140
GACGTCCTGG ACAGACCGAG TCCCGGGAAG CCCCAGCACT GCCGCTGCCA CACTGCCCTG AGCCCAAATG 150         160        171                                           198
GGGGAGTGAG AGGCCATAGC TGTCTGGC ATG GGC CTC TCC ACC GTG CCT GAC CTG CTG
                                 MET Gly Leu Ser Thr Val Pro Asp Leu Leu 207             216             225             234             243             252
CTG CCG GTG CTG CTC GAG CTG TTG GTG GGA ATA TAC CCC TCA CGG GTT ATT
Leu Pro Val Leu Leu Glu Leu Leu Val Gly Ile Tyr Pro Ser Gly Val Ile 261             270             279             288             297             306
GGA CTG GTC CCT CAC CTA GGG GAC AGG GAG AAG AGA GAT AGT GTG TGT CCC CAA
Gly Leu Val Pro His Leu Gly Asp Arg Glu Lys Arg Asp Ser Val Cys Pro Gln 315             324             333             342             351             360
GGA AAA TAT ATC CAC CCT CAA AAT AAT TCG ATT TGC TGT ACC AAG TGC CAC AAA
Gly Lys Tyr Ile His Pro Gln Asn Asn Ser Ile Cys Cys Thr Lys Cys His Lys
```

FIG. 21B

```
                                                                              414
     369       378       387       396       405
GGA ACC TAC TTG TAC AAT GAC TGT CCA GGC CCG GGG CAG GAT ACG GAC TGC AGG
Gly Thr Tyr Leu Tyr Asn Asp Cys Pro Gly Pro Gly Gln Asp Thr Asp Cys Arg
                                                                              468
     423       432       441       450       459
GAG TGT GAG AGC GGC TCC TTC ACC GCT TCA GAA AAC CAC CTC AGA CAC TGC CTC
Glu Cys Glu Ser Gly Ser Phe Thr Ala Ser Glu Asn His Leu Arg His Cys Leu
                                                                              522
     477       486       495       504       513
AGC TGC AAA TGC CGA AAG GAA ATG GGT CAG GTG GAG ATC TCT TCT TGC ACA
Ser Cys Lys Cys Arg Lys Glu MET Gly Gln Val Glu Ile Ser Ser Cys Thr
                                                                              576
     531       540       549       558       567
GTG GAC GAC ACC TGT GGC TGC AGG AAG AAC CAG TAC CGG CAT TAT TGG
Val Asp Asp Thr Cys Gly Cys Arg Lys Asn Gln Tyr Arg His Tyr Trp
                                                                              630
     585       594       603       612       621
AGT GAA AAC CTT TTC CAG TGC TTC AAT TGC AGC CTC CTC AAT GGG ACC GTG
Ser Glu Asn Leu Phe Gln Cys Phe Asn Cys Ser Leu Leu Asn Gly Thr Val
                                                                              684
     639       648       657       666       675
CAC CTC TCC TGC CAG GAG AAA CAG AAC ACC GTG TGC ACC TGC CAT GCA GGT TTC
His Leu Ser Cys Gln Glu Lys Gln Asn Thr Val Cys Thr Cys His Ala Gly Phe
```

FIG. 21C

```
       693         702         711         720         729         738
        |           |           |           |           |           |
 TTT CTA AGA GAA AAC GAG TGT GTC TCC TGT AGT AAC TGT AAG AAA AGC CTG GAG
 Phe Leu Arg Glu Asn Glu Cys Val Ser Cys Ser Asn Cys Lys Lys Ser Leu Glu 747         756         765         774         783         792
                    |           |           |           |           |           |
 TGC ACG AAG TTG TGC CTA CCC CAG ATT GAG AAT GTT AAG GGC ACT GAG GAC TCA
 Cys Thr Lys Leu Cys Leu Pro Gln Ile Glu Asn Val Lys Gly Thr Glu Asp Ser 801         810         819         828         837         846
                    |           |           |           |           |           |
 GGC ACC ACA GTG CTG TTG CCC CTG GTC ATT TTC TTT GGT CTT CTT TTA TCC
 Gly Thr Val Leu Leu Pro Leu Val Ile Phe Phe Gly Leu Leu Leu Ser 855         864         873         882         891         900
                    |           |           |           |           |           |
 CTC CTC ATT GGT TTA ATG TAT CGC TAC CAA CGG TGG AAG TCC AAG CTC TAC
 Leu Leu Ile Gly Leu MET Tyr Arg Tyr Gln Arg Trp Lys Ser Lys Leu Tyr 909         918         927         936         945         954
                    |           |           |           |           |           |
 TCC ATT GTT TGT GGG AAA TCG ACA CCT GAA AAA GAG GGG GAG CTT GAA GGA ACT
 Ser Ile Val Cys Gly Lys Ser Thr Pro Glu Lys Glu Gly Glu Leu Glu Gly Thr 963         972         981         990         999         1008
                    |           |           |           |           |           |
 ACT ACT AAG CCC CTG GCC CCA AAC AGC TTC AGT CCC ACT CCA GGC TTC ACC
 Thr Thr Lys Pro Leu Ala Pro Asn Ser Phe Ser Pro Thr Pro Gly Phe Thr
```

FIG. 21D

```
      1017        1026        1035        1044        1053        1062
      |           |           |           |           |           |
 CCC ACC CTG GGC TTC AGT CCC GTG CCC AGT TCC ACC TTC ACC TCC AGC TCC ACC
 Pro Thr Leu Gly Phe Ser Pro Val Pro Ser Ser Thr Phe Thr Ser Ser Ser Thr 1071        1080        1089        1098        1107
      |           |           |           |           |
                                                                  1116
 TAT ACC CCC GGT GAC TGT CCC AAC TTT GCG GCT CCC CGC AGA GAG GTG GCA CCA
 Tyr Thr Pro Gly Asp Cys Pro Asn Phe Ala Ala Pro Arg Arg Glu Val Ala Pro 1125        1134        1143        1152        1161        1170
      |           |           |           |           |           |
 CCC TAT CAG GGG GCT GAC CCC ATC CTT GCG ACA GCC CTC GCC TCC GAC CCC ATC
 Pro Tyr Gln Gly Ala Asp Pro Ile Leu Ala Thr Ala Leu Ala Ser Asp Pro Ile 1179        1188        1197        1206        1215        1224
      |           |           |           |           |           |
 CCC AAC CCC CTT CAG AAG GAG GAC TGG AGC GAC CAC AAG CCA CAG AGC CTA GAC
 Pro Asn Pro Leu Gln Lys Glu Asp Trp Ser Asp His Lys Pro Gln Ser Leu Asp 1233        1242        1251        1260        1269        1278
      |           |           |           |           |           |
 ACT GAT GAC CCC GCG ACG CTG TAC GCC GTG GTG GAG AAC GTG CCC TTG CGC
 Thr Asp Asp Pro Ala Thr Leu Tyr Ala Val Val Glu Asn Val Pro Pro Leu Arg 1287        1296        1305        1314        1323        1332
      |           |           |           |           |           |
 TGG AAG GAA TTC GTG CGG CGC CTA GGG CTG AGC GAC CAC GAG ATC GAT CGG CTG
 Trp Lys Glu Phe Val Arg Arg Leu Gly Leu Ser Asp His Glu Ile Asp Arg Leu
```

FIG. 21E

```
      1341              1350          1359          1368          1377              1386
GAG CTG CAG AAC GGG CGC TGC CTG CGC GAG GCG CAA TAC AGC ATG CTG GCG ACC
Glu Leu Gln Asn Gly Arg Cys Leu Arg Glu Ala Gln Tyr Ser MET Leu Ala Thr 1395              1404          1413          1422          1431              1440
TGG AGG CGG CGC ACG CGG CGC CCG GAG GCC ACG CTG GAG CTG CTG GGA CGC GTG
Trp Arg Arg Arg Thr Arg Arg Pro Glu Ala Thr Leu Glu Leu Leu Gly Arg Val 1449              1458          1467          1476          1485              1494
CTC CGC GAC ATG GAC CTG CTG GGC TGC CTG GAG GAC ATC GAG GAG GCG CTT TGC
Leu Arg Asp MET Asp Leu Leu Gly Cys Leu Glu Asp Ile Glu Glu Ala Leu Cys 1503              1512          1521          1530                            1546      1556
GGC CCC GCC CTC CCG CCC GCG CCC AGT CTT CTC AGA TGA GGCTGCGCCC CTGCGGGCAG
Gly Pro Ala Leu Pro Pro Ala Pro Ser Leu Arg 1566       1576       1586       1596       1606       1616       1626
CTCTAAGGAC CGTCCTGCGA GATCGCCCTTC CAACCCCACT TTTTTCTGGA AAGGAGGGGT CCTGCAGGGG 1636       1646       1656       1666       1676       1686       1696
CAAGCAGGAG CTAGCAGCCG CCTACTTGGT GCTAACCCCT CGATGTACAT AGCTTTTCTC AGCTGCCTGC
```

FIG. 21F

```
      1706       1716       1726       1736       1746       1756       1766
GCGCCGCCGA CAGTCAGCGC TGTGCGCGCG GAGAGAGGTG CGCCGTGGGC TCAAGAGCCT GAGTGGGTGG 1776       1786       1796       1806       1816       1826       1836
TTTGCGAGGA TGAGGGACGC TATGCCTCAT GCCCGTTTTG GGTGTCCTCA CCAGCAAGGC TGCTCGGGGG 1846       1856       1866       1876       1886       1896       1906
CCCCTGGTTC GTCCCTGAGC CTTTTTCACA GTGCATAAGC AGTTTTTTTT GTTTTTGTTT TGTTTTTGTTT 1916       1926       1936       1946       1956       1966       1976
TGTTTTTAAA TCAATCATGT TACACTAATA GAAACTTGGC ACTCCCTGTGC CCTCTGCCTG GACAAGCACA 1986       1996       2006       2016       2026       2036       2046
TAGCAAGCTG AACTGTCCTA AGGCAGGGGC GAGCACGGAA CAATGGGGCC TTCAGCTGGA GCTGTGGACT 2056       2066       2076       2086
TTTGTACATA CACTAAAATT CTGAAGTTAA AGCTCAAAAA AA
```

FIG. 22

GA ATT CCA CAA CGG TTT CCC TCT AGA AAT AAT TTT GTT TAA CTT TAA GAA GGA GAT ATA CAT

Start gene 10 protein
sequence

ATG GCT AGC ATG ACT GGT GGA CAG CAA ATG GGT ACG GAT CCG ATC TTG GAG GAT GAT TAA
Met Ala Ser Met Thr Gly Gly Gln Gln Met Gly Thr Asp Pro Ile Leu Glu Asp Asp stop Translational coupler ATG GAC AGC GTT TGC CCC
Met Asp Ser Val Cys Pro Start TNF inhibitor
sequence

FIG. 31

U937-derived TNF inhibitor1 (30 kDa)

( )-( )-Val-( )-Pro-Gln-Gly-Lys-Tyr-Ile-His-Pro-Gln-( )-Asn-( )-Ile-

U937-derived TNF inhibitor2 (40 kDa)

Leu-Pro-Ala-Gln-Val-Ala-Phe-Thr-Pro-Tyr-Ala-Pro-Glu-Pro-Gly-Ser-Thr-Cys-Arg-Leu-Arg-Glu-Tyr-Tyr-Asp-Gln-Thr-Ala-Gln-Met-Cys-Cys-Ser-Lys-Cys-

Urine-derived TNF inhibitor2 (40 kDa)

Ala-Gln-Val-Ala-Phe-Thr-Pro-Tyr-Ala-Pro-Glu-Pro-Gly-Ser-Thr-Cys-( )-Leu-( )-Glu-

V8 DIGEST

Arg.C  A215

FIG. 36

```
          10         20         30         40         50         60         70         80
LPAQVAFTPYAPEPGSTCRLREYYDQTAQMCCSKCSPGQHAKVFCTKTSDTVCDSCEDSTYTQL_N_VPECLSCGSRCSSDQVE_
     NT
                                            V34,35                    V37              V6
         V25                         R16                                              R4
           R12                                              R16T30V9
                                                                R16T30
                  R4                                                         R16T30V4

90        100        110        120        130        140        150
_ACTREQNRICTCRPGWYCALSKQEGCRLCAPLRKCRPGFGVARPGTETSDVVCKPCAPGTFS_TTSS(T)(D)(P)(C)(R)(P)
                V23                   V20                       R10
                  R14                              R16T13                    R10C17
  R4                                  R16T13                    R10C32
                                      R10-C19
                                                                R10
```

FIG. 37

```
          200       209       218       227
     CCG  GAG  GGG  AGC  ACA  TGC  CGG  CTC  AGA  GAA  TAC  TAT  GAC
     Pro  Glu  Gly  Ser  Thr  Cys  Arg  Leu  Arg  Glu  Tyr  Tyr  Asp
236                                                              281
CAG  ACA  GCT  CAG  ATG  TGC  AGC  AAG  TGC  CCG  GGC  CAA  CAT  GCA  AAA  GTC
Gln  Thr  Ala  Gln  MET  Cys  Ser  Lys  Cys  Pro  Gly  Gln  His  Ala  Lys  Val
245                  254       263       272                        335
CAG                                                             TCG
                                                                Ser
290                  308       317       326
TTC  TGT  ACC  AAG  ACC  TCG  GAC  ACC  GTG  TGT  GAC  TCC  TGT  GAG  GAC  AGC  ACA  TAC
Phe  Cys  Thr  Lys  Thr  Ser  Asp  Thr  Val  Cys  Asp  Ser  Cys  Glu  Asp  Ser  Thr  Tyr
344                  353       362       371       380                        389
ACC  CAG  CTC  TGG  AAC  TGG  GTT  CCC  GAG  TGC  TTG  AGC  TGT  GGC  TCC  CGC  TGT  AGC
Thr  Gln  Leu  Trp  Asn  Trp  Val  Pro  Glu  Cys  Leu  Ser  Cys  Gly  Ser  Arg  Cys  Ser
398                  407       416       425       434                        443
TCT  GAC  CAG  GTG  GAA  ACT  CAA  GCC  TGC  ACT  CGG  GAA  CAG  AAC  CGC  ATC  TGC  ACC
Ser  Asp  Gln  Val  Glu  Thr  Gln  Ala  Cys  Thr  Arg  Glu  Gln  Asn  Arg  Ile  Cys  Thr
452                  461       470
TGC  AGG  CCC  GGC  TGG  TAC  TGC
Cys  Arg  Pro  Gly  Trp  Tyr  Cys
```

FIG. 38

Leu Pro Ala Gln Val Ala Phe Thr Pro Tyr Ala Pro Glu Pro Gly Ser

Thr Cys Arg Leu Arg Glu Tyr Tyr Asp Gln Thr Ala Gln Met Cys Cys

Ser Lys Cys Ser Pro Gly Gln His Ala Lys Val Phe Cys Thr Lys Thr

Ser Asp Thr Val Cys Asp Ser Cys Glu Asp Ser Thr Tyr Thr Gln Leu

Trp Asn Trp Val Pro Glu Cys Leu Ser Cys Gly Ser Arg Cys Ser Ser

Asp Gln Val Glu Thr Gln Ala Cys Thr Arg Glu Gln Asn Arg Ile Cys

Thr Cys Arg Pro Gly Trp Tyr Cys Ala Leu Ser Lys Gln Glu Gly Cys

Arg Leu Cys Ala Pro Leu Arg Lys Cys Arg Pro Gly Phe Gly Val Ala

Arg Pro Gly Thr Glu Thr Ser Asp Val Val Cys Lys Pro Cys Ala Pro

Gly Thr Phe Ser Asn Thr Thr Ser Ser Thr Asp Ile Cys Arg Pro His

Gln Ile Cys Asn Val Val Ala Ile Pro Gly Asn Ala Ser Arg Asp Ala

Val Cys Thr Ser Thr Ser Pro Thr Arg Ser Met Ala Pro Gly Ala Val

His Leu Pro Gln Pro Val Ser Thr Arg Ser Gln His Thr Gln Pro Thr

Pro Glu Pro Ser Thr Ala Pro Ser Thr Ser Phe Leu Leu Pro Met Gly

Pro Ser Pro Pro Ala Glu Gly Ser Thr Gly Asp

FIG. 39A

```
           10         20         30         40         50         60         70
GAATTCGGCG CAGCGGAGCC TGGAGAGAAG GCGCTGGGCT GCGAGGGCGC GAGGGCGCGA GGGCAGGGGG 80         90                    101        110        119
CAACCGGACC CCGCCCCGCAC CC ATG GCG CCC GTC GCC GTC TGG GCC GCG CTG GCC
                          MET Ala Pro Val Ala Val Trp Ala Ala Leu Ala 128         137                146                155                164                173
GTC GGA CTG GAG CTC TGG  GCT GCG GCG GCG  CCC CAC GCC TTG  CCC GCC CAG GTG GCA TTT
Val Gly Leu Glu Leu Trp  Ala Ala Ala Ala  Pro His Ala Leu  Pro Ala Gln Val Ala Phe 182         191                200                209                218                227
ACA CCC TAC CCC CCS GAG  CCC CCC AGC CTC  ACA ICC CGG CTC  ABA BAA TAC TAT SAC
Thr Pro Tyr Ala Pro Glu  Pro Pro Ser Thr  Thr Cys Arg Leu  Arg Glu Tyr Tyr Asp 236         245                254                263                272                281
CAG ACA GCT CAG ATG TGC  AGC TGC AAG TCG  CCG GGC CAA CAT GCA AAA GTC
Gln Thr Ala Gln MET Cys  Ser Cys Lys Cys  Ser Pro Gly Gln His Ala Lys Val 290         299                308                317                326                335
TTC TGT ACC AAG ACC TCG  GAC GTG TGT GAC  TCC TGT GAG GAC TCC ACA TAC
Phe Cys Thr Lys Thr Ser  Asp Thr Val Cys  Asp Ser Cys Glu Asp Ser Thr Tyr
```

FIG. 39B

```
344   353           362   371           380   389
ACC CAG CTC TGG AAC TGG GTT CCC GAG TGC TTG AGC TGT GGC TCC CGC TGT AGC
Thr Gln Leu Trp Asn Trp Val Pro Glu Cys Leu Ser Cys Gly Ser Arg Cys Ser 398                 407   416           425   434           443
TCT GAC CAG GTG GAA ACT CAA GCC TGC ACT CGG GAA CAG AAC CGC ATC TGC ACC
Ser Asp Gln Val Glu Thr Gln Ala Cys Thr Arg Glu Gln Asn Arg Ile Cys Thr 452                 461   470           479   488           497
TGC AGG CCC GGC TGG TAC TGC GCG CTG AGC AAG CAG GAG TGC GGG CGG CTG TGC
Cys Arg Pro Gly Trp Tyr Cys Ala Leu Ser Lys Gln Glu Gly Cys Arg Leu Cys 506                 515   524           533   542           551
GCG CCG CTG CGC AAG TGC CGC CCG GGC TTC GGC GTG GCC AGA CCA ACT GAA
Ala Pro Leu Arg Lys Cys Arg Pro Gly Phe Gly Val Ala Arg Pro Thr Glu 560                 569   578           587   596           605
ACA TCA GAC GTG GTG TGC AAG CCC TGT GCC CCG GGG ACG TTC TCC AAC ACG ACT
Thr Ser Asp Val Val Cys Lys Pro Cys Ala Pro Gly Thr Phe Ser Asn Thr Thr
```

FIG. 39C

```
614      623       632       641       650       659
TCA TCC  ACG GAT  ATT TGC  CCC CAC  CAG ATC  TGT AAC  GTG GTG  GCC ATC  CCT
Ser Ser  Thr Asp  Ile Cys  Pro His  Gln Ile  Cys Asn  Val Val  Ala Ile  Pro 668      677       686       695       704       713
GGG AAT  GCA AGC  AGG GAT  GTC TGC  ACG TCC  ACG CCC  ACC CGG  AGT ATG
Gly Asn  Ala Ser  Arg Asp  Val Cys  Thr Ser  Thr Pro  Thr Arg  Ser MET 722      731       740       749       758       767
GCC CCA  GGG GCA  GTA CAC  CCC CAG  GTG TCC  ACA CGA  TCC CAA  CAC ACG
Ala Pro  Gly Ala  Val His  Pro Gln  Val Ser  Thr Arg  Ser Gln  His Thr 776      785       794       803       812       821
CAG CCA  ACT CCA  GAA CCC  AGC GCT  CCA AGC  ACC TCC  TTC CTG  CTC CCA  ATG
Gln Pro  Thr Pro  Glu Pro  Ser Ala  Pro Ser  Thr Ser  Phe Leu  Leu Pro  MET 830      839       848       857       866       875
GGC CCC  AGC CCC  CCA GCT  GGG AGC  ACT GGC  GAC TTC  GCT CTT  CCA GTT  GGA
Gly Pro  Ser Pro  Pro Ala  Gly Ser  Thr Gly  Asp Phe  Ala Leu  Pro Val  Gly
```

FIG. 39D

```
884       893       902       911       920       929
CTG ATT GTG GGT GTG ACA GCC TTG GGT CTA CTA ATA ATA GGA GTG AAC TGT
Leu Ile Val Gly Val Thr Ala Leu Gly Leu Leu Ile Ile Gly Val Asn Cys 938       947       956       965       974       983

GTC ATC ATG ACC CAG GTG AAA AAG AAG CCC TTG TGC CTG CAG AGA GAA GCC AAG
Val Ile MET Thr Gln Val Lys Lys Lys Pro Leu Cys Leu Gln Arg Glu Ala Lys 992       1001      1010      1019      1028      1037
GTG CCT CAC TTG CCT GCC GAT AAG GCC CGG GGT ACA CAG GGC CCC GAG CAG CAG
Val Pro His Leu Pro Ala Asp Lys Ala Arg Gly Thr Gln Gly Pro Glu Gln Gln 1046      1055      1064      1073      1082      1091
CAC CTG ATC ACA GCG CCG AGC AGC AGC TCC AGC AGC CTG GAG AGC TCG GCC
His Leu Ile Thr Ala Pro Ser Ser Ser Ser Ser Ser Ser Leu Glu Ser Ser Ala 1100      1109      1118      1127      1136      1145
AGT GCG TTG GAC AGA AGG GCG CCC ACT CGG AAC CAG CCA CAG GCA CCA GGC GTG
Ser Ala Leu Asp Arg Arg Ala Pro Thr Arg Asn Gln Pro Gln Ala Pro Gly Val
```

FIG. 39E

```
       1154         1163         1172         1181         1190         1199
       |GAG  GCC  AGT  GGG  GCC  GGG  GAG  GCC  CGG  GCC  AGC  ACC  GGG  AGC  TCA  GAT  TCT  TCC
        Glu  Ala  Ser  Gly  Ala  Gly  Glu  Ala  Arg  Ala  Ser  Thr  Gly  Ser  Ser  Asp  Ser  Ser 1208         1217         1226         1235         1244         1253
       |CCT  GGT  GGC  CAT  GGG  ACC  CAG  GTC  AAT  GTC  ACC  TGC  ATC  GTG  AAC  GTC  TGT  AGC
        Pro  Gly  Gly  His  Gly  Thr  Gln  Val  Asn  Val  Thr  Cys  Ile  Val  Asn  Val  Cys  Ser 1262         1271         1280         1289         1298         1307
       |AGC  TCT  GAC  CAC  AGC  TCA  CAG  TGC  TCC  CAA  GCC  AGC  TCC  ACA  ATG  GGA  GAC
        Ser  Ser  Asp  His  Ser  Ser  Gln  Cys  Ser  Ser  Gln  Ala  Ser  Ser  Thr  MET  Gly  Asp 1316         1325         1334         1343         1352         1361
       |ACA  GAT  TCC  AGC  CCC  TCG  GAG  TCC  CCG  AAG  GAC  GAG  CAG  GTC  CCC  TTC  TCC  AAG
        Thr  Asp  Ser  Ser  Pro  Ser  Glu  Ser  Pro  Lys  Asp  Glu  Gln  Val  Pro  Phe  Ser  Lys 1370         1379         1388         1397         1406         1415
       |GAG  GAA  TGT  GCC  TTT  CGG  TCA  CAG  CTG  GAG  ACG  CCA  GAG  ACC  CTG  GGG  AGC
        Glu  Glu  Cys  Ala  Phe  Arg  Ser  Gln  Leu  Glu  Thr  Pro  Glu  Thr  Leu  Gly  Ser
```

FIG. 39F

```
1424         1433         1442         1451         1460         1469
ACC GAA GAG AAG CCC CTG CCC CTT GGA GTG CCT GAT GCT GGG ATG AAG CCC AGT
Thr Glu Glu Lys Pro Leu Pro Leu Gly Val Pro Asp Ala Gly MET Lys Pro Ser 1478         1488         1498         1508         1518         1528         1538
  >
TAA CCAGGCCGGT GTGGGCTGTG TCGTAGCCAA GGTGGGCTGA GCCCTGGCAG GATGACCCTG 1548       1558       1568       1578       1588       1598       1608
CGAAGGGGCC CTGGTCCTTC CAGGCCCCCA CCACTAGGAC TCTGAGGCTC TTTCTGGGCC AAGTTCCTCT 1618       1628       1638       1648       1658       1668       1678
AGTGCCCTCC ACAGCCGCAG CCTCCCCTCTG ACCTGCAGGC CAAGAGCAGA GGCAGCGGGT TGTGAAAGC 1688       1698       1708       1718       1728       1738       1748
CTCTGCTGCC ATGGTGTGTC CCTCTCGGAA GGCTGGCTGG GCATGGACGT TCGGGGCATG CTGGGGCAAG 1758       1768       1778       1788       1798       1808       1818
TCCCTGACTC TCTGTGACCT GCCCCGCCCA GCTGCACCTG CCAGCCTGGC TTCTGGAGCC CTTGGGTTTT
```

FIG. 39G

```
     1828       1838       1848       1858       1868       1878       1888
TTGTTTGTTT GTTTGTTTGT TTGTTTGTTT CTCCCCCTGG GCTCTGCCCC AGCTCTGGCT TCCAGAAAAC 1898       1908       1918       1928       1938       1948       1958
CCCAGCATCC TTTTCTGCAG AGGGGCTTTC TGGAGAGGAG GGATGCTGCC TGAGTCACCC ATGAAGACAG 1968       1978       1988       1998       2008       2018       2028
GACAGTGCTT CAGCCTGAGG CTGAGACTGC GGGATGGTCC TGGGGCTCTG TGCAGGGAGG AGGTGGCAGC 2038       2048       2058       2068       2078       2088       2098
CCTGTAGGGA ACGGGGTCCT TCAAGTTAGC TCAGGAGGCT TGGAAAGCAT CACCTCAGGC CAGGTGCAGT 2108       2118       2128       2138       2148       2158       2168
CCCTCACGCC TATGATCCCA GCACTTTGGG AGGCTGAGGC GGGTGGATCA CCTGAGGTTA GGAGTTCGAG 2178       2188       2198       2208       2218       2228       2238
ACCAGCCTGG CCAACATGGT AAAACCCCAT CTCTACTAAA AATACAGAAA TTAGCCGGGC GTGGTGGCGG
```

FIG. 39H

```
         2248       2258       2268       2278       2288       2298       2308
GCACCTATAG TCCCAGCTAC TCAGAAGCCT GAGGCTGGGA AATCGTTTGA ACCCGGGAAG CGGAGGTTGC 2318       2328       2338       2348       2358       2368       2378
AGGGAGCCGA GATCACGCCA CTGCACTCCA GCCTGGGCGA CAGAGCGAGA GTCTGTCTCA AAAGAAAAAA

2388
AAAAAAAACC GAATTC
```

TNF - bp Δ51 C8 Fractions

C8 FRACTIONS

TNF - bp Δ53 C8 Profile

NUCLEIC ACIDS ENCODING TNF INHIBITOR AND METHOD OF PRODUCTION

CROSS-REFERENCE TO RELATED APPLICATION

This is a divisional of application Ser. No. 08/375,242, filed Jan. 19, 1995 and issued Nov. 7, 2000 as U.S. Pat. No. 6,143,866, which is a continuation-in-part of application Ser. No. 07/479,661 filed Feb. 7, 1990 now abandoned, which is in turn a continuation-in-part of applications Ser. Nos. 07/381,080 filed Jul. 18, 1989, and 07/450,329 filed Dec. 11, 1989 for "Tumor Necrosis Factor (TNF) Inhibitor and Method for Obtaining the Same", both abandoned.

BACKGROUND OF THE INVENTION

Tumor necrosis factors are a class of proteins produced by numerous cell-types, including monocytes and macrophages. At least two TNFs have been previously described, specifically TNF alpha and TNF beta (lymphotoxin).

These known TNFs have important physiological effects on a number of different target cells involved in the inflammatory response. The proteins cause both fibroblasts and synovial cells to secrete latent collagenase and prostaglandin E2, and cause osteoblastic cells to carry out bone resorption. These proteins increase the surface adhesive properties of endothelial cells for neutrophils. They also cause endothelial cells to secrete coagulant activity and reduce their ability to lyse clots. In addition they redirect the activity of adipocytes away from the storage of lipids by inhibiting expression of the enzyme lipoprotein lipase. TNFs cause hepatocytes to synthesize a class of proteins know as "acute phase reactants" and they act on the hypothalamus as pyrogens. Through these activities, it has been seen that TNFs play an important part in an organism's response to stress, to infection, and to injury. See, e.g., articles by P. J. Selby et al. in Lancet, Feb. 27, 1988, pg. 483; H. F. Starnes, Jr. et al. in *J. Clin. Invest.* 82: 1321 (1988); A. Oliff et al. in Cell 50:555 (1987); and A. Waage et al. in Lancet, Feb. 14, 1987, pg. 355.

However, despite their normally beneficial effects, circumstances have come to light in which the actions of TNFs are harmful. For example, TNF alpha injected into animals gives rise to the symptoms of septic shock; endogenous TNF levels have been observed to increase following injection of bacteria or bacterial cell walls. TNFs also cause bowel necrosis and acute lung injury, and they stimulate the catabolism of muscle protein. In addition, the ability of TNFs to increase the level of collagenase in an arthritic joint and to direct the chemotaxis and migration of leukocytes and lymphocytes may also be responsible for the degradation of cartilage and the proliferation of the synovial tissue in this disease. Therefore, TNFs may serve as mediators of both the acute and chronic stages of immunopathology in rheumatoid arthritis. TNFs may also be responsible for some disorders of blood clotting through altering endothelial cell function. Moreover, excessive TNF production has been demonstrated in patients with AIDS and may be responsible for some of the fever, acute phase response and cachexia seen with this disease and with leukemias.

In these and other circumstances in which TNF has a harmful effect, there is clearly a clinical use for an inhibitor of TNF action. Systemically administered, TNF inhibitors would be useful therapeutics against septic shock and cachexia. Locally applied, such TNF inhibitors would serve to prevent tissue destruction in an inflamed joint and other sites of inflammation. Indeed, such TNF inhibitors could be even more effective when administered in conjunction with interleukin-I (IL-1) inhibitors.

One possibility for therapeutic intervention against the action of TNF is at the level of the target cell's response to the protein. TNF appears to act on cells through a classical receptor-mediated pathway. Thus, any molecule which interferes with the ability of TNF to bind to its receptors either by blocking the receptor or by blocking the TNF would regulate TNF action. For these reasons, proteins and small molecules capable of inhibiting TNF in this manner have been sought by the present inventors.

SUMMARY OF THE INVENTION

As noted above, this invention relates to TNF inhibitors generally, and, more specifically, to a urine-derived TNF inhibitor. Additionally, the present invention relates to biologically-active analogs of this inhibitor.

An object of the present invention is to provide purified forms of TNF inhibitor which are active against TNF alpha. An additional object of the present invention is to provide these inhibitors in purified forms to enable the determination of their amino acid sequence. A further object is to provide the amino acid sequences of certain TNF inhibitors. In addition it is an object of this invention to provide a cellular source of the mRNA coding for TNF inhibitors and a cDNA library containing a cDNA for the inhibitors. Furthermore, it is an object of this invention to provide a genomic clone of DNA coding for the TNF inhibitors, and the coding sequences of that DNA.

The identification of biologically-active analogs of such TNF inhibitors with enhanced or equivalent properties is also one of the objects of the invention.

Additionally, it is an object of this invention to provide a recombinant-DNA system for the production of the TNF inhibitor described herein. A further object of the present invention includes providing purified forms of TNF inhibitor which would be valuable as pharmaceutical preparations exhibiting activity against TNF. Another object of the present invention includes providing purified combinations of TNF inhibitors and IL-1 inhibitors which are valuable as pharmaceutical preparations exhibiting activity against both IL-1 and TNF.

The inventors of the present invention have isolated at least two TNF inhibitor proteins with TNF-inhibiting properties. A 30kDa protein and a 40kDa protein have been obtained in their purified forms. The amino acid sequence of the 30kDa TNF inhibitor protein has been obtained. The amino acid sequence data of the 40kDa TNF inhibitor protein has also been obtained. Both the 30kDa TNF inhibitor and the 40kDa TNF inhibitor are novel, previously undescribed proteins.

A human genomic DNA clone which contains the gene for the 30kDa protein has been obtained. A cell source of this protein has been identified and a cDNA clone has been obtained and the nucleic acid sequence of the gene for the protein determined. In addition, the gene clone has been placed in a vector which has been found to express the protein in host cells. Also a process has been developed for purifying the protein in an active form.

A cell source has been identified which produces the 40kDa protein and a cDNA clone has been obtained and the nucleic acid sequence determined of the gene for the 40kDa protein. The full cDNA clones encoding for both the 30kDa TNF inhibitor precursor and the 40kDa TNF inhibitor precursor have been expressed in mammalian cells to yield an increase in TNF binding sites on the cell surface.

A gene coding for the mature form of the 30kDa protein has been expressed in E. Coli. Three seperate genes coding for all or portions of the mature 40kDa protein have also been expressed in E. Coli. The three 40kDa Inhibitor proteins expressed—mature 40kDa TNF inhibitor, 40kDa TNF inhibitor Δ51 and 40kDa TNF inhibitor Δ53—each exhibit TNF inhibiting activity. Mature 40kDa TNF inhibitor, as isolated from medium conditioned by human U937 cells, and 40kDa TNF inhibitor Δ51 and 40kDa TNF inhibitor Δ53, are collectively referred to as 40kDa TNF inhibitor.

The 30kDa TNF inhibitor has shown activity in inhibiting TNF alpha. The 40kDa TNF inhibitor has shown inhibitory action against both TNF alpha and TNF beta.

It will now be possible to perform the large scale production of these TNF inhibitors through recombinant DNA technology. These inhibitors should be suitable for use in pharmaceutical formulations useful in treating pathophysiological conditions mediated by TNF.

BRIEF DESCRIPTION OF THE DRAWINGS

FIG. 1 describes a cytotoxicity assay for TNF in the absence (-.-.) and in the presence (-x-x-) of TNF inhibitor (30kDa). Various concentrations of TNF were incubated with and without TNF inhibitor, and the cytotoxicity assay was performed as described in Example 1.

FIG. 2 describes a native gel shift assay in which “a” depicts TNF alone, and “b” depicts TNF+TNF inhibitor (30kDa).

FIG. 3 describes Con A-Peroxidase staining of TNF inhibitor (30kDa). About 200 ng of each protein were run on 14% SDS-PAGE, and transferred to nitrocellulose filter. Glycoproteins were identified using Con A-peroxidase staining. In this figure, “a” depicts a molecular weight marker, “b” depicts Ovalbuimin, “c” depicts bovine serum albumin, and “d” depicts TNF inhibitor.

FIG. 4 describes chemical deglycoslylation of TNF inhibitor (30kDa). About 200 ng of TNF inhibitor were chemically deglycosylated (lane C) as described in Example 1.

FIG. 5 describes N-glycanase treatment of TNF inhibitor (30kDa). Purified TNF inhibitor was iodinated by Bolton-Hunter reagent, and denatured-iodinated TNF inhibitor was treated with N-glycanase for 6 hours at 37° C. In this figure, “a” depicts native TNF inhibitor, and “b” depicts deglycosylated TNF inhibitor.

FIG. 6A describes an $OD_{280}$ profile of the DEAE Sepharose CL-6B chromatography of 20 1 urine.

FIG. 6B describes an autoradiograph of the corresponding native gel shift assay indicating a peak of TNF inhibitor at fraction 57–63, which is about 80 mM NaCl.

FIG. 7 describes an $OD_{280}$ profile of the 0.05 M Na Phosphate pH 2.5 elution from the TNF affinity column.

FIGS. 8A and 8C describe chromatographic profiles ($OD_{215}$ and $OD_{280}$) of the RP8 purification of the TNF inhibitor (30kDa) with the L929 bioassay of fractions from the RP8 column showing a peak of TNF inhibitor at fractions 28–31 which is about 18% acetonitrile and at fractions 35 and 36 which is about 21% acetonitrile.

FIG. 8B describes a silver stained 15% SDS-PAGE of the RP8 pool showing a single band at 30kDa.

FIG. 9A describes a peptide purification of Lys-C digestion of TNF inhibitor (30kDa).

FIGS. 9B-1 to 9B-3 describe a peptide purification of alkylated (*) Lys-C digests of TNF inhibitor (30kDa).

FIGS. 10A and 10B describe a peptide purification of two alkylated (*) Asp-N digests of TNF inhibitor (30kDa).

FIGS. 11A and 11B describe peptide purifications of an endopeptidase V8 digest of reduced carboxymethylated TNF inhibitor (30kDa).

Figure 12:
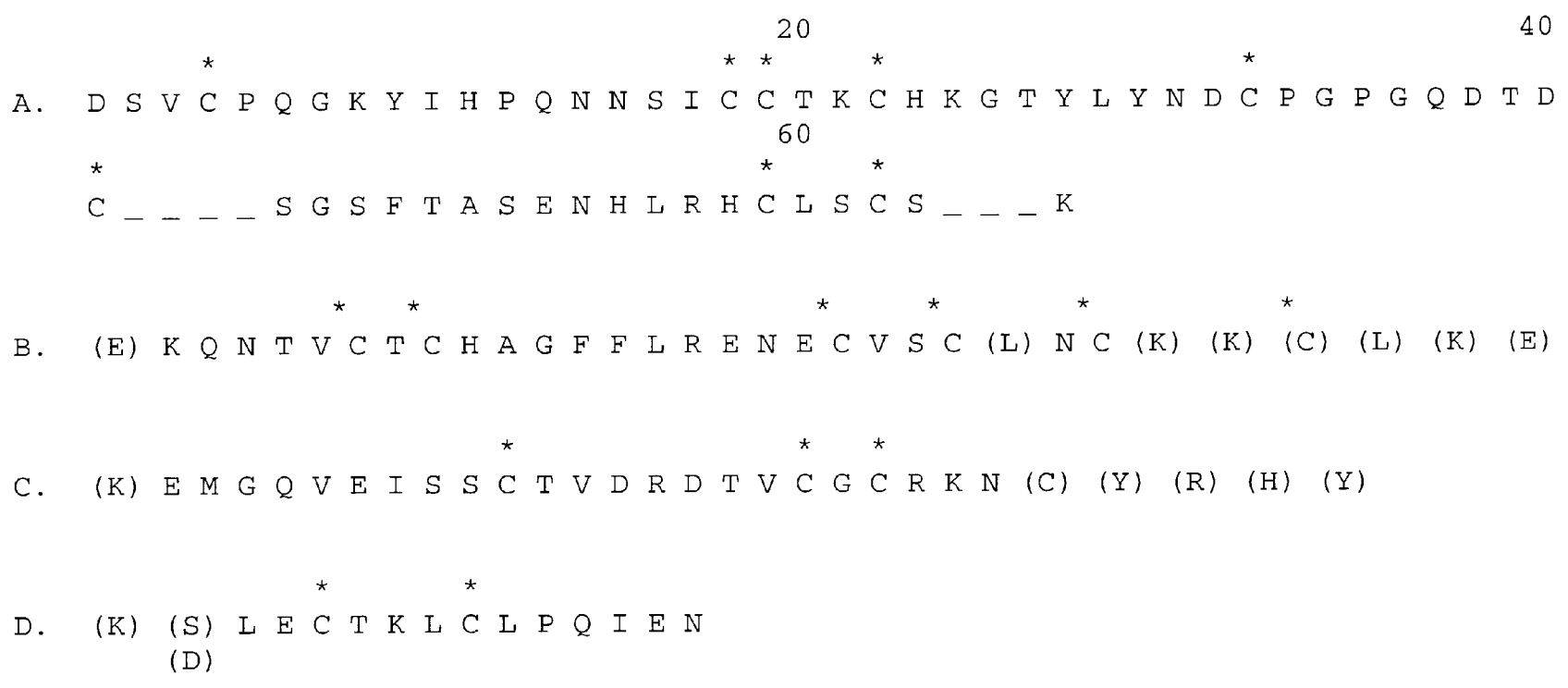

FIG. 12 describes amino acid sequences present in TNF inhibitor (30kDa). Blanks in the sequence indicate the residue has not been unambiguously identified by protein sequencing. C* indicates the identification of carboxymethylcysteine by the presence of $^3H$ in the residue.

FIGS. 13A to 13C describe the DNA sequence of a genomic clone encoding at least a portion of a TNF inhibitor (30kDa).

FIG. 14 describes at least 70% of the mature amino acid sequence of a preferred TNF inhibitor (30kDa).

FIG. 15 describes detection of TNF inhibitor in U937 supernatant by the gel shift assay.

FIG. 16 describes detection of TNF inhibitor in hplc fractions from U937 supernatant.

FIG. 17 describes the Northern blot according to Example 4.

FIG. 18 describes the deglycosylated TNF inhibitor (30kDa) binding to TNF. Glycosylated and deglycosylated TNF inhibitor were incubated with TNF affigel, and flow through materials and eluates of the gel were analysed on SDS-PAGE. In this figure, (11) indicates flow through of TNF-INH, reduced and oxidized, (21) indicates flow through of deglycosylated TNF-INH, reduced and oxidized, (51) indicates flow through of native TNF-INH, (12) indicates eluate of TNF-INH, reduced and oxidized, (22) indicates eluate of deglycoslylated TNF-INH, reduced and oxidized, and (52) indicates eluate of native TNF-INH.

FIG. 19 describes the complete amino acid sequence of the 30kDa TNF inhibitor.

FIGS. 20A and 20B describe the cDNA sequence encoding the amino acid sequence shown in FIG. 19.

FIGS. 21A to 21F describe the entire cDNA sequence for the precursor of the 30kDa TNF inhibitor.

FIG. 22 describes the DNA sequence near the start of the TNF inhibitor (30kDa) gene in plasmid pTNFIX-1.

FIG. 23 describes the plasmid pCMVXV beta TNFBP stop A.

FIG. 24 describes the plasmid pSVXVTNFBP stop A.

FIG. 25 describes a chromatographic profile $OD_{215}$ of the RP8 column of the 30kDa TNF inhibitor from *E. Coli*. The L929 bioassay results are also shown (-x-x).

FIG. 26 describes a silver stained 14% SDS-PAGE of the RP8 Fractions in FIG. 25.

FIG. 27 describes a chromatographic profile ($OD_{215}$) of the RP8 purification of the TNF inhibitors from U937 cells. The L929 bioassay results are also shown with a bar graph. Two distinctive TNF inhibitor peaks are seen.

FIG. 28 describes a silver stained 14% SDS-PAGE of the RP8 fractions. Fraction number 30 contains the 30kDa TNF inhibitor and fraction number 35 contains the 40kDa TNF inhibitor.

FIG. 29 describes a chromatographic profile ($OD_{215}$) of the purification of urinary 40kDa TNF inhibitor. The second TNF inhibitory peak from several RP8 chromatographies were combined and reanalyzed on an RP8 column. TNF-inhibitory activity is shown with a bar graph. The difference between the $OD_{215}$ peak and the activity peak reflects the dead volume between the detector and the fraction collector.

FIG. 30 describes a silver stained 14% SDS-PAGE of the RP8 fractions of urine. Fraction number 32 contains the 40kDa TNF inhibitor.

FIG. 31 describes the amino terminal sequences of U937 derived inhibitors (30kDa and 40kDa), and urine-derived 40kDa TNF inhibitor.

Figure 32:
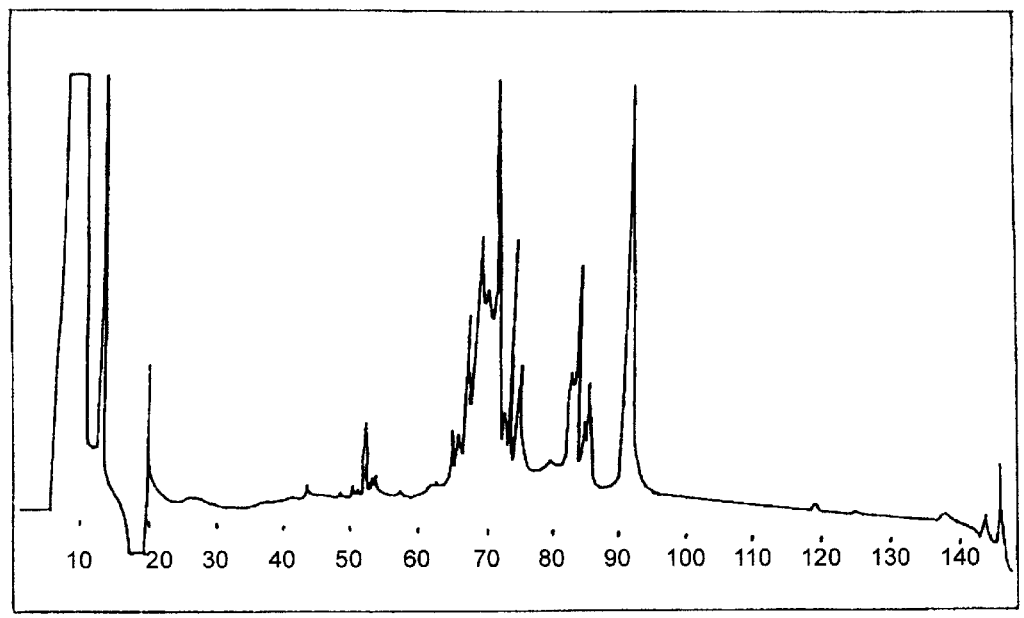

FIG. 32 describes a peptide purification of endopeptidase V8 digested 40kDa TNF inhibitor.

Figure 33:
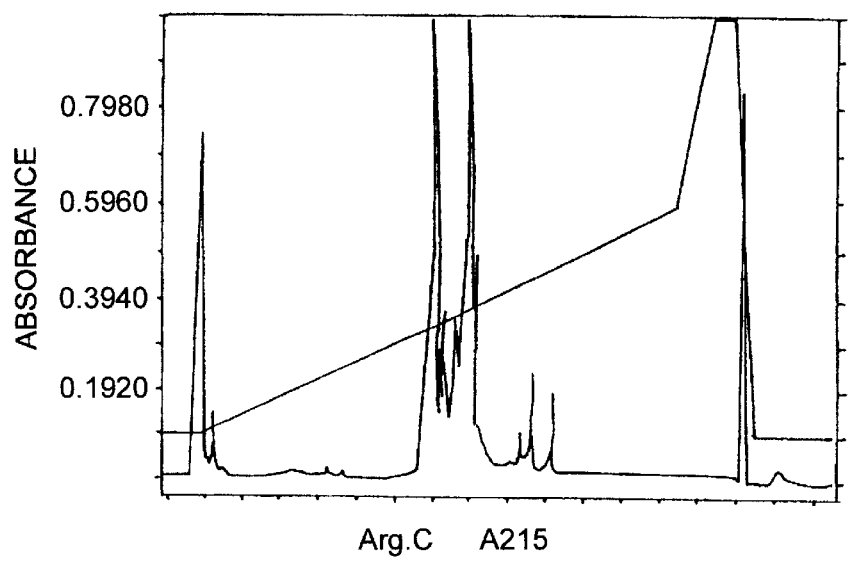

FIG. 33 describes a peptide purification endopeptidase Arg-C digested 40kDa TNF inhibitor.

Figure 34:
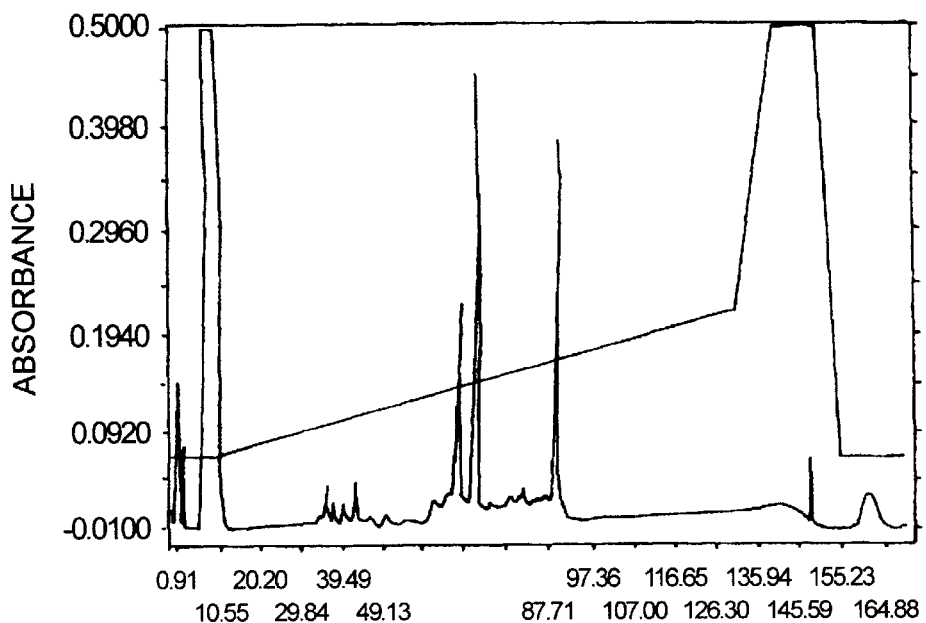

FIG. 34 describes a peptide purification of trypsin digested Arg-C16 peptide.

Figure 35:
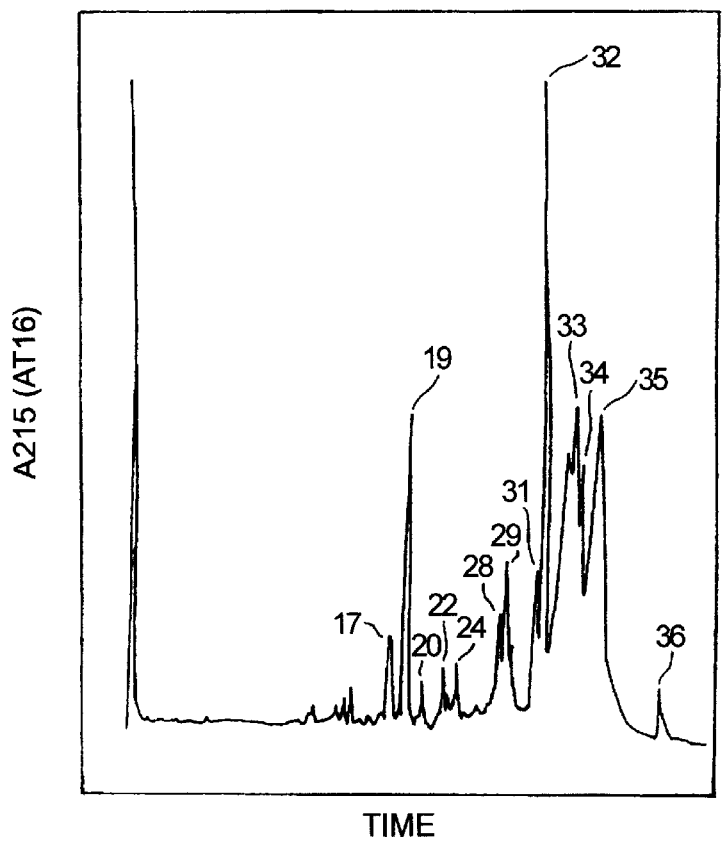

FIG. 35 describes a peptide purification of chymotrypsin digested Arg-C10 peptide.

FIG. 36 describes a primary structure of the 40kDa TNF inhibitor.

FIG. 37 describes a portion of the 40kDa TNF inhibitor cDNA sequence along with the predicted amino acid translation product.

FIG. 38 describes the complete amino acid sequence of the 40kDa TNF inhibitor.

FIGS. 39A to 39H describes the entire cDNA sequence for the precursor of the 40kDa TNF inhibitor, along with its deduced translation product.

Figure 40:
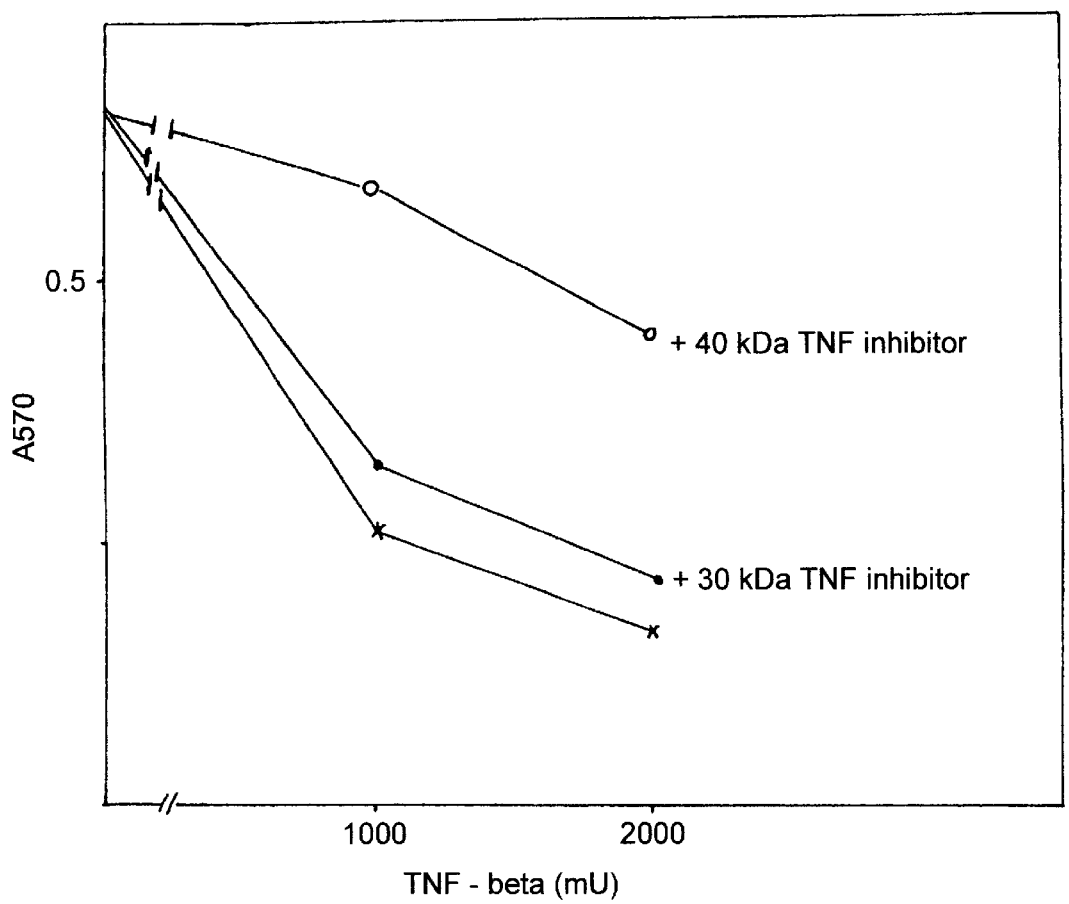

FIG. 40 describes a cytotoxicity assay for TNF beta (lymphotoxin) in the presence (o-o) of 40kDa TNF inhibitor, in the presence (o-o) of 30kDa TNF inhibitor and without any inhibitor (x-x).

Figure 41:
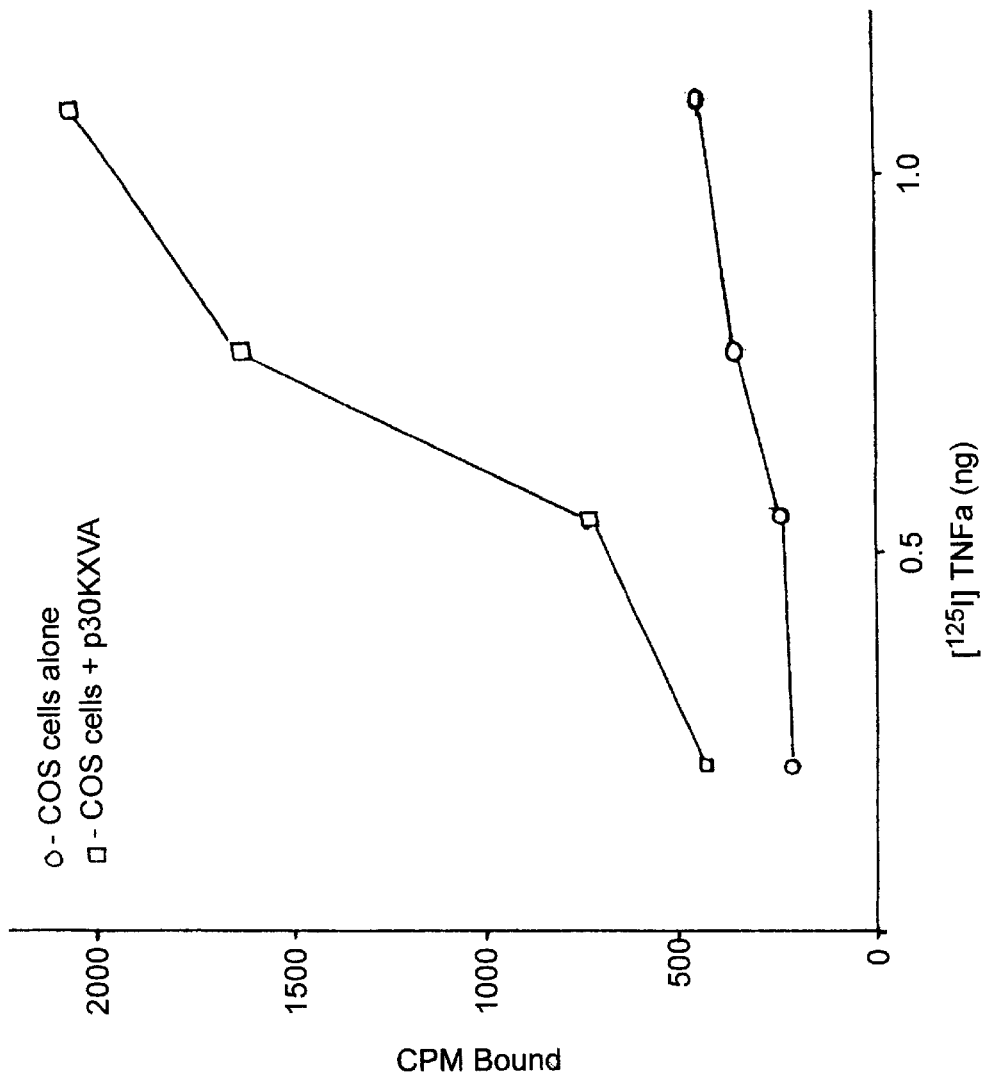

FIG. 41 describes the expression of the 30kDa TNF inhibitor cDNA sequence shown in FIG. 21 in COS7 cells. COS cells were transfected with plasmids using the lipofectin procedure of Felgner et al., 1987, Proc. Natl. Acad. Sci. USA 84:7413-17. $3.4 \times 10^5$ cells were incubated with the indicated amounts of [$^{125}$I] TNFa at a specific activity of $5.6 \times 10^4$ cpm/ng and the amount bound to the cells determined. Open symbols are the total cpm associated with cells after a 4 hour incubation at 4° C. Closed symbols represent bound [$^{125}$I] TNFa in the presence of 180 fold excess of cold unlabeled TNFa.

Figure 42:
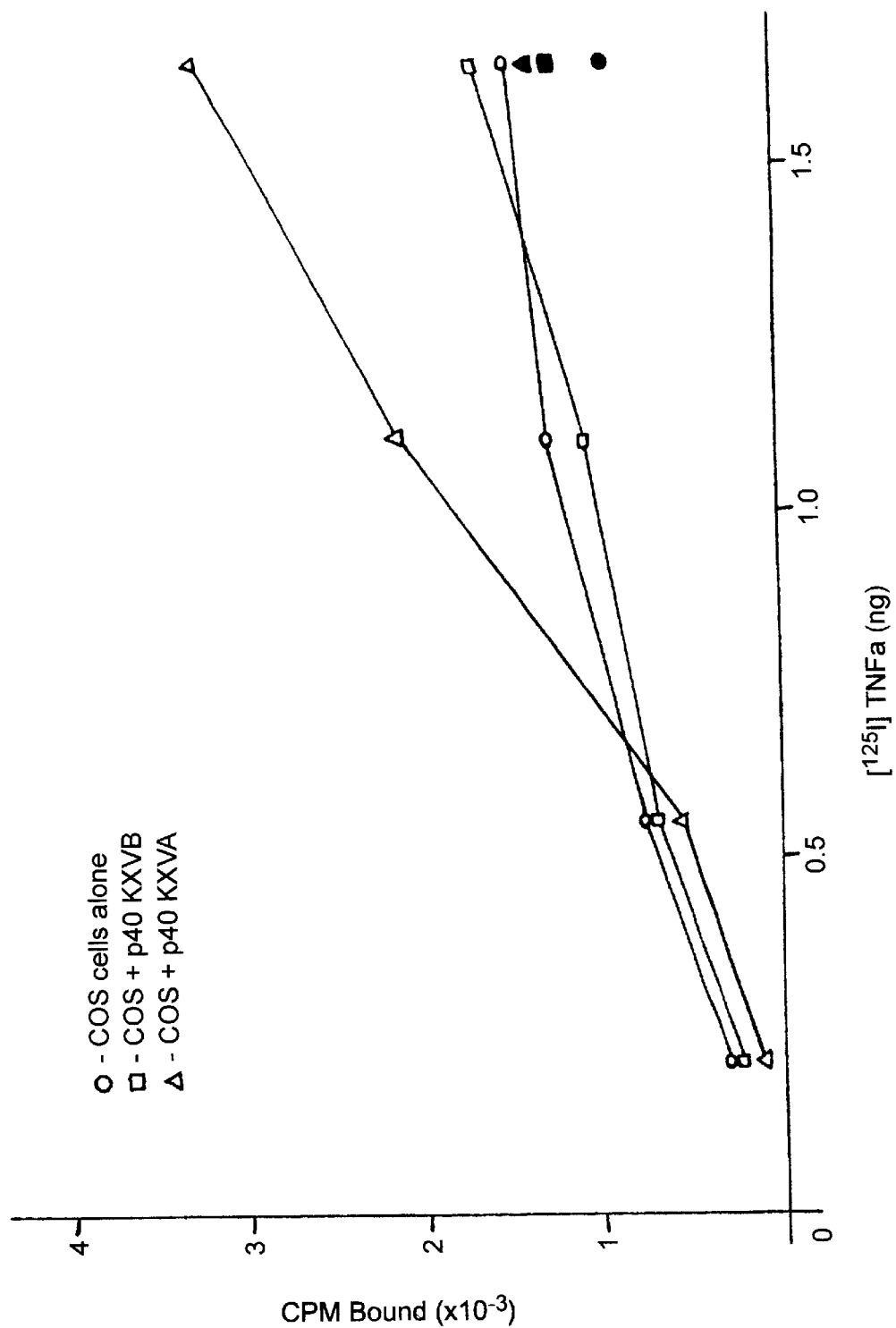

FIG. 42 describes the expression of the 40kDa TNF inhibitor cDNA sequence shown in FIG. 39 in COS7. Assay conditions were as described in FIG. 41. The darkened symbols represent the bound [$^{125}$I] TNFa in the presence of 180 fold excess of cold unlabeled TNFa.

Figure 43:
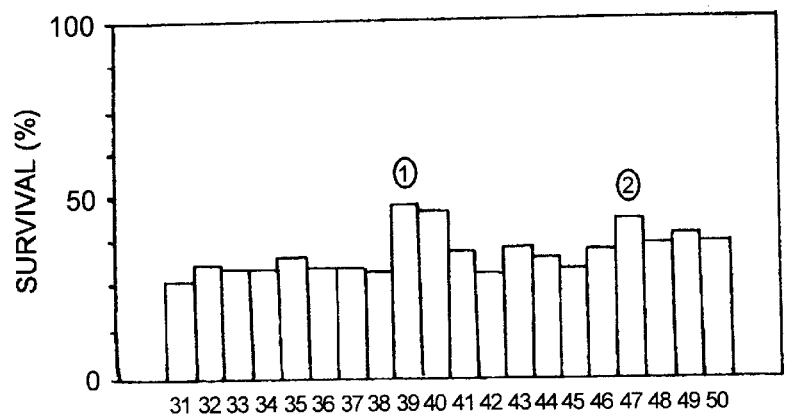

FIG. 43 describes the cytotoxicity assay of an HPLC RPC-8 fraction of the human monocytes which were treated with PMA and PHA for 24 hours.

Figure 44A:
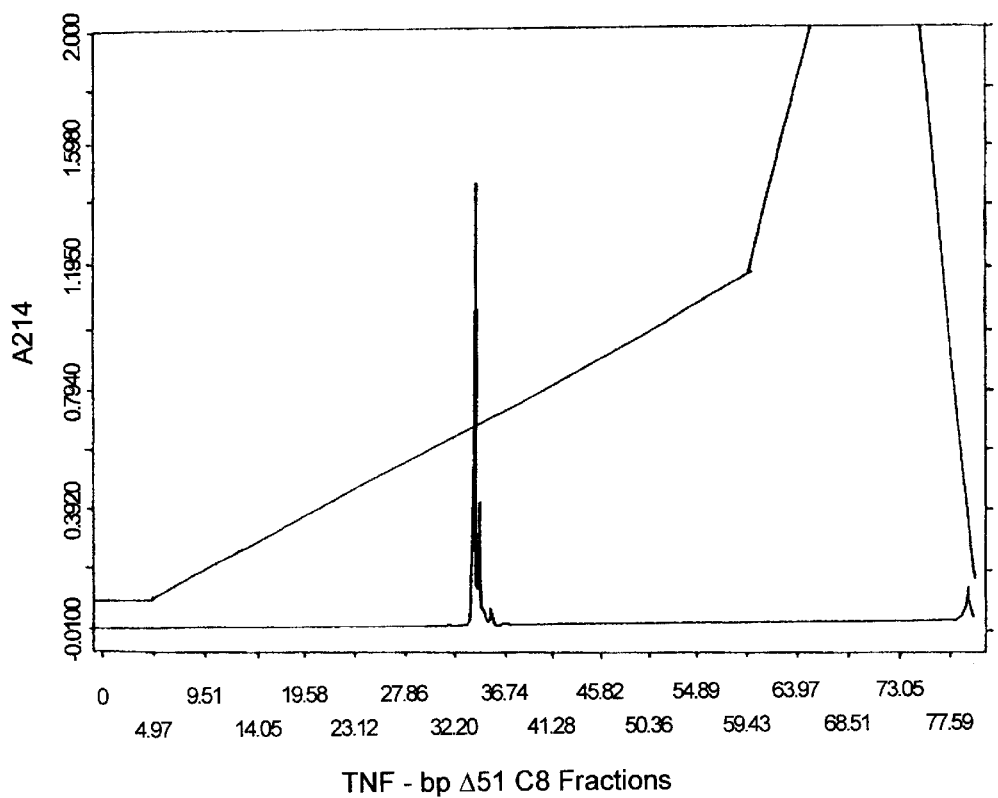
Figure 44B:
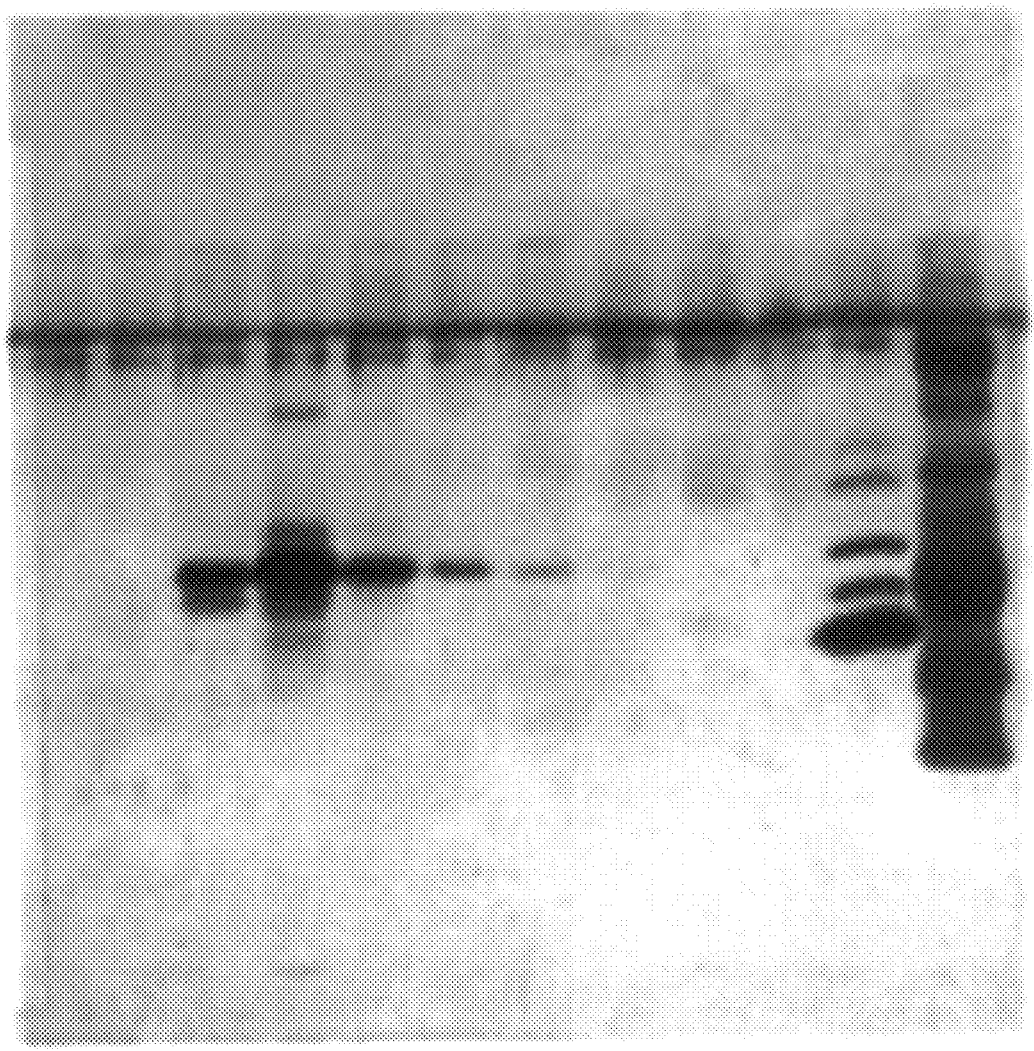
Figure 44C:
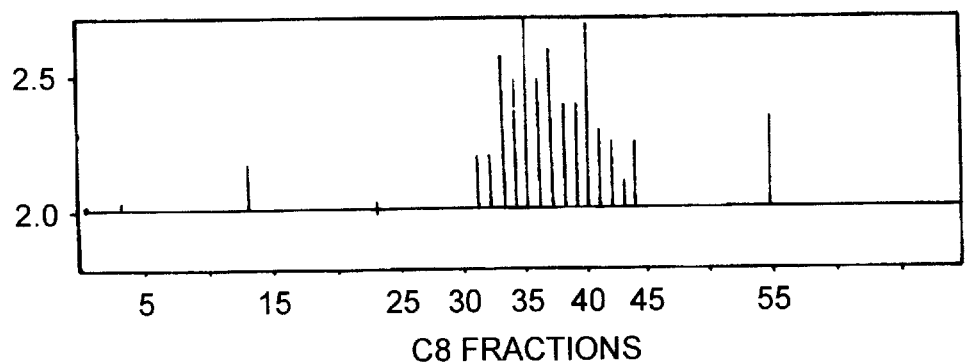

FIGS. 44A to 44C describe the RPC-8 chromatographic pattern of 40kDa TNF inhibitor Δ51A, SDS-polyacrylamide gel analysis of the fractions (B), and the cytotoxicity assay on L929 cells (C).

Figure 45A:
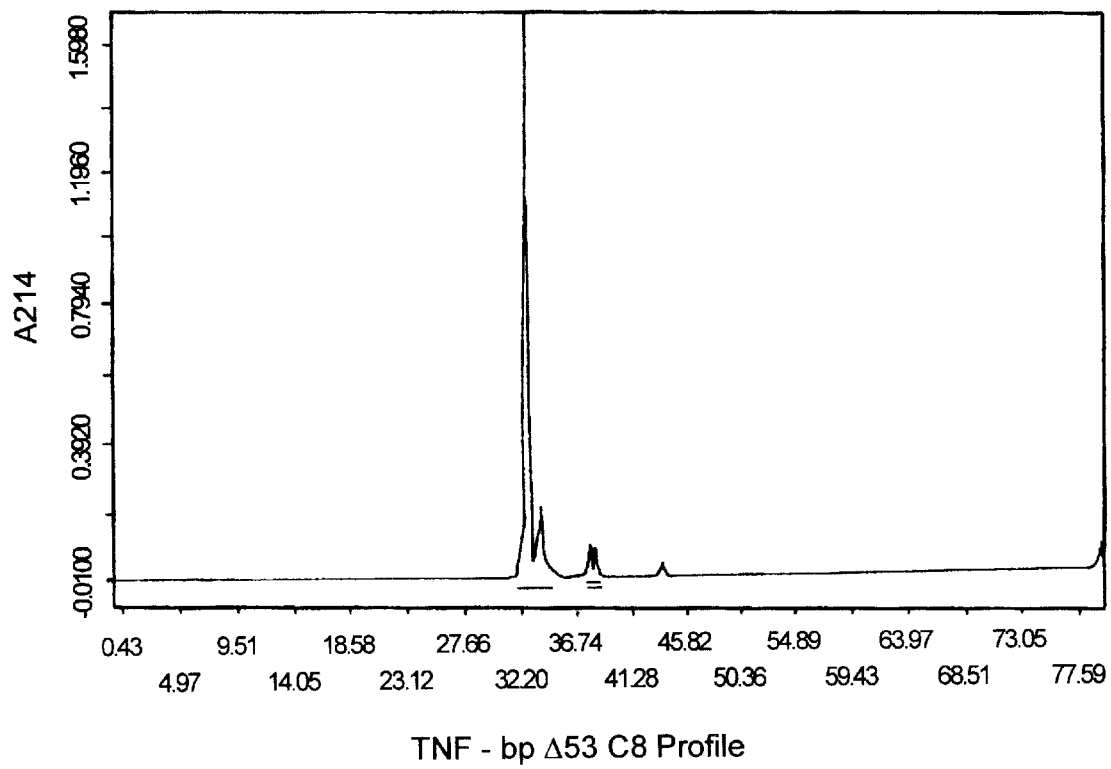
Figure 45B:
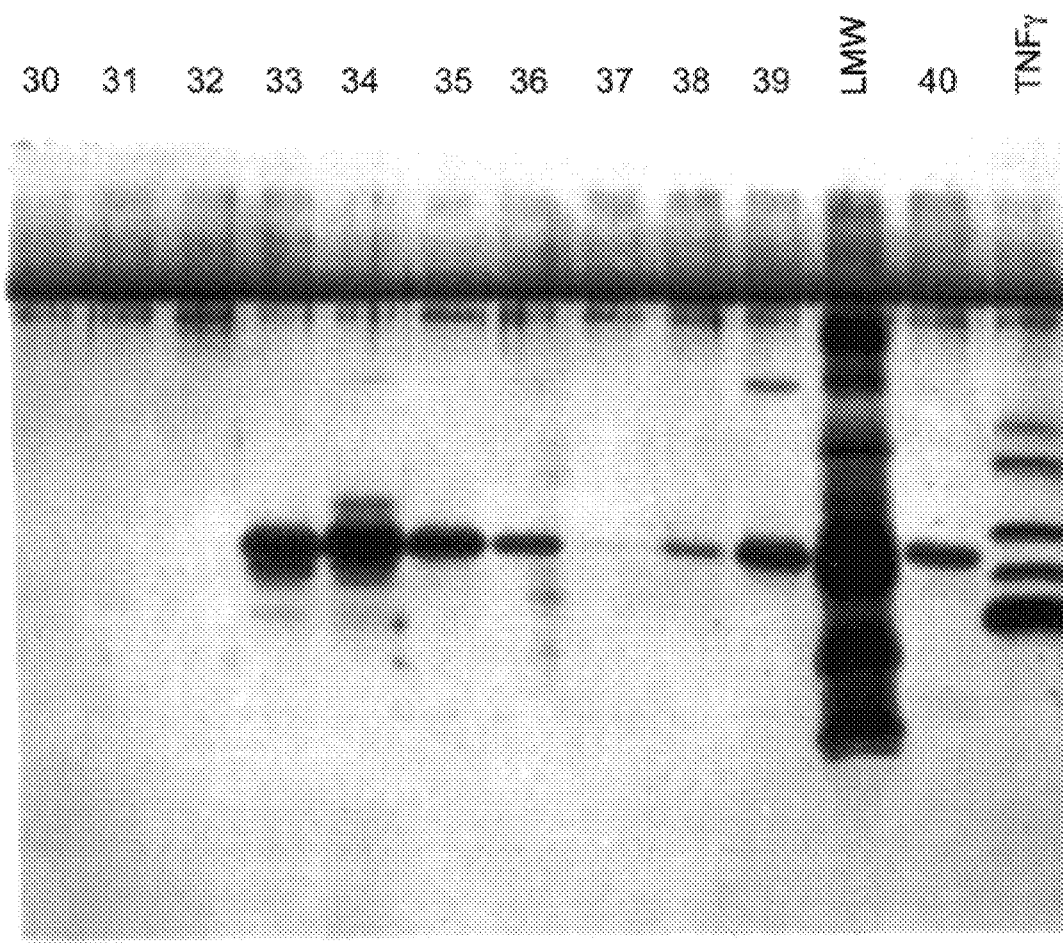
Figure 45C:
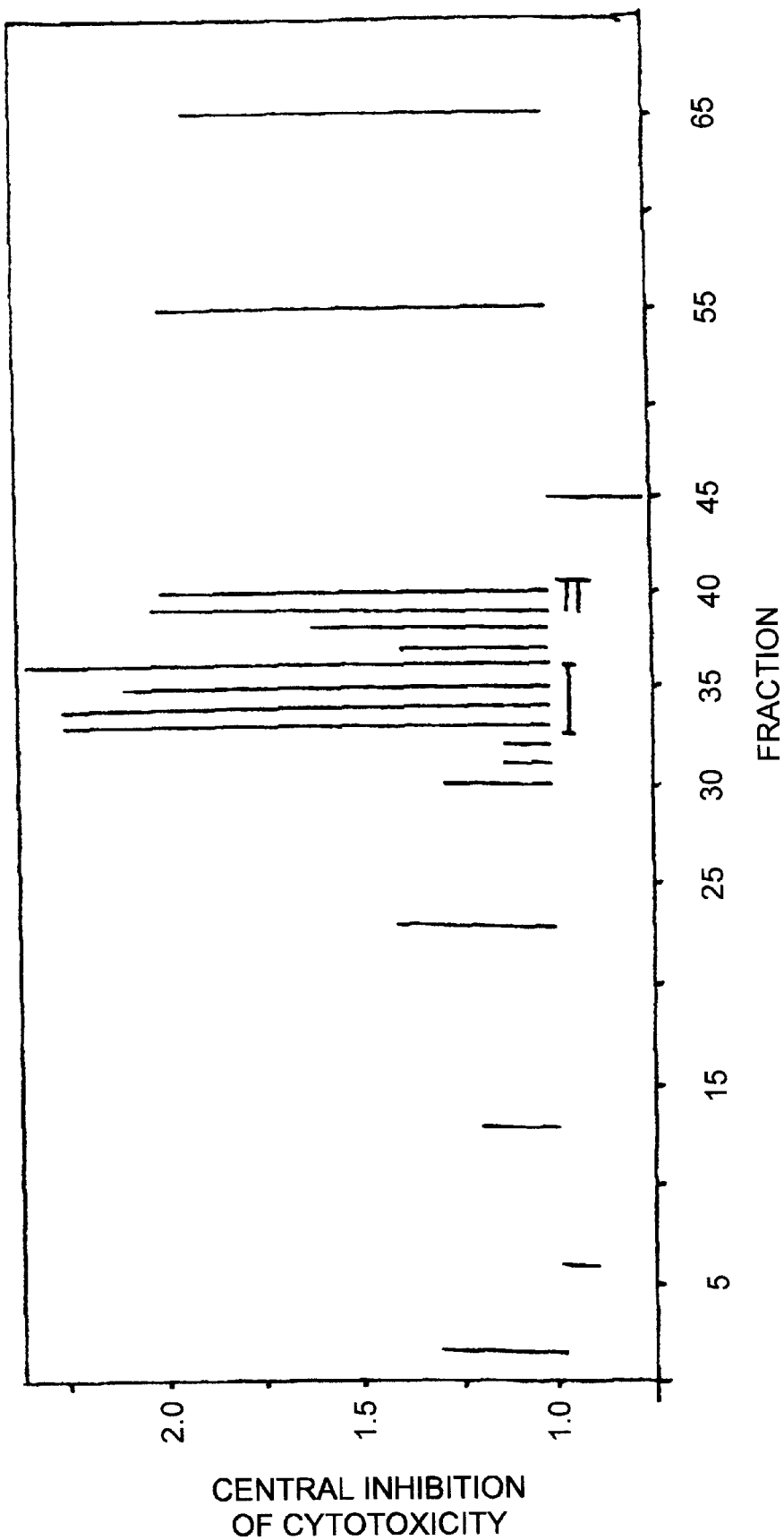

FIGS. 45A to 45C describe the RPC-8 chromatographic pattern of 40kDa TNF inhibitor Δ53 (A), SDS-polyacrylamide gel analysis of fractions (B), and the cytotoxicity assay on L929 cells (C).

DESCRIPTION OF THE PREFERRED EMBODIMENTS

Reference will now be made in detail to the presently preferred embodiments of the invention, which, together with the following examples, serve to explain the principals of the invention.

1. Inhibitor Isolated from Urine

As noted above, the present invention relates to TNF inhibitors which have been isolated in a purified form. In one embodiment of this invention, the TNF inhibitors are preferably derived from urine. In addition, the invention encompasses substantially purified TNF inhibitors of any origin which are biologically equivalent to the inhibitor isolated from urine. Throughout this specification, any reference to a TNF inhibitor or simply an inhibitor should be construed to refer to each of the inhibitors identified and described herein.

By "biologically equivalent" as used throughout the specification and claims, we mean compositions of the present invention which are capable of preventing TNF action in a similar fashion, but not necessarily to the same degree as the native TNF inhibitor isolated from urine. By "substantially homologous" as used throughout the ensuing specification and claims, is meant a degree of homology to the native TNF inhibitor isolated from urine in excess of that displayed by any previously reported TNF inhibitor. Preferably, the degree of homology is in excess of 70%, most preferably in excess of 80%, and even more preferably in excess of 90%, 95% or 99%. A particularly preferred group of TNF inhibitors are in excess of 95% homologous with the native inhibitor. The percentage of homology as described herein is calculated as the percentage of amino acid residues found in the smaller of the two sequences which align with identical amino acid residues in the sequence being compared when four gaps in a length of 100 amino acids may be introduced to assist in that alignment as set forth by Dayhoff, in *Atlas of Protein Sequence and Structure* Vol. 5, p. 124 (1972), National Biochemical Research Foundation, Washington, D.C., specifically incorporated herein by reference. Also included as substantially homologous are those TNF inhibitors which may be isolated by virtue of cross-reactivity with antibodies to the described inhibitor or whose genes may be isolated through hybridization with the gene or with segments of the described inhibitor.

The preferred TNF inhibitors of the present invention have been derived from urine and, for the first time, have been isolated in a purified form. For the purposes of the present application, "pure form" or "purified form," when used to refer to the TNF inhibitors disclosed herein, shall mean a preparation which is substantially free of other proteins which are not TNF inhibitor proteins, Preferably, the TNF inhibitors of the present invention are at least 50% percent pure, preferably 75% pure and more preferably 80%, 95% or 99% pure. In one embodiment of the present invention, the TNF inhibitor protein preparation is sufficiently pure to enable one of ordinary still in the art to determine its amino acid sequence without first performing further purification steps.

At least two TNF inhibitors have been isolated by the methods set forth in the examples. The two inhibitors are approximately 30kDa and approximately 40kDa molecules on SDS-PAGE. The 30kDa inhibitor eluates from a DEAE CL6B column at about 80 millimolar NaCl in Tris buffer, pH 7.5. The amino acid sequence of the 30kDa inhibitor is set forth in FIG. 19, and the amino acid sequence of the 40kDa inhibitor is set forth in FIG. 38. The 30kDa TNF inhibitor has been shown to inhibit the activity of TNF alpha, and has little effect on the activity of TNF beta. The 40kDa TNF inhibitor has been shown to exhibit a significant inhibiting effect against both TNF alpha and TNF beta (lymphotoxin).

2. Inhibitor Isolated from U937 Conditioned Medium

In an alternate embodiment of the present invention, TNF inhibitors are isolated from a medium conditioned by human U937 cells. Two TNF inhibitor proteins have been identified and isolated from this conditioned medium. The two TNF inhibitors are 30kDa and 40kDa proteins that are substantially homologous to the 30kDa and 40kDa TNF inhibitors isolated from urine, and are biologically equivalent to such proteins.

3. Structure of 30kDa TNF Inhibitor

The 30kDa TNF inhibitor isolated from urine is a glycoprotein, containing at least one carbohydrate moiety. In one embodiment of this invention, the natural 30kDa TNF inhibitor is deglycosylated. The deglycosylated TNF inhibitor, which retains its ability to bind to TNF, is within the scope of the present invention. Fully and partially deglycosylated 30kDa TNF inhibitor is encompassed by this invention. The deglycosylated 30kDa TNF inhibitor isolated from urine is about an 18kDa protein.

The gene sequence identified that encodes the 30kDa protein does not contain a termination codon as would be anticipated for the amino acid sequence of the 18kDa protein. The inventors theorize, but are in no way to be limited by this theory, that the proteins produced in vivo contain additional amino acid sequences. According to this theory, the protein encoded is a TNF receptor molecule. The inhibitor protein encoded by the cDNA has a hydrophobic sequence that would be compatible with the cell membrane-spanning region and a TNF binding portion that would extend extracellularly from the cell membrane. In accord with this hypothesis and as described in Example 19, the cDNA has been expressed in COS cells and leads to an increase in the number of TNF binding sites on the cell. The TNF inhibitors of the present invention, therefore, are the receptor fragments or portions of the receptor molecule. Such binding fragments have been identified with respect to other binding/inhibitory molecules (e.g., IL-2 inhibitor), and are referred to as soluble receptors.

This theory is consistent with the lack of a termination codon in the nucleotide sequence that would correspond to the terminus of the protein as anticipated by the known sequence of the isolated TNF inhibitor factor. It is also consistent with the fact that the nucleotide sequence beyond where the termination codon should be found, encodes a series of hydrophobic amino acids.

The present invention, therefore, encompasses not just the portion of the TNF inhibitors identified and described, but all proteins containing any portion of the amino acid sequence encoded by the cDNA sequences identified and described herein.

4. Structure of 40kDa TNF Inhibitor

The 40kDa TNF inhibitor isolated from medium conditioned by human U937 cells and identified in urine is a glycoprotein, containing at least one carbohydrate moiety. In one embodiment of this invention, the natural 40kDa TNF inhibitor is deglycosylated. The deglycosylated 40kDa TNF inhibitor, which retains its ability to bind to both TNF alpha and TNF beta (lymphotoxin) is within the scope of the present invention. Fully and partially deglycosylated 40kDa TNF inhibitor is encompassed by this invention. The inventors theorize that the 40kDa TNF inhibitor may also be a soluble receptor. The gene sequence identified that encodes the 40kDa protein does not contain a termination codon as would be anticipated for the amino acid sequence of the deglycosylated 40kDa TNF inhibitor. As described in Example 20, the cDNA has been expressed in COS cells and leads to an increase in the number of TNF binding sites on the cell.

The present invention encompasses the gene encoding the mature 40kDa protein isolated from medium conditioned by human U937 cells and identified in urine, and larger and smaller portions of such gene to the extent that the TNF inhibiting activity of the encoded protein is not affected. As can be seen by reference to FIG. 38, the mature 40kDa TNF inhibitor has a proline rich area near the anticipated c-terminus of the protein. 40kDa TNF inhibitors in which all or portions of the proline rich region are not included in the protein are active as TNF inhibitors, and are within the scope of the present invention. Two such shortened proteins are described in Examples 17 and 22 below, and are referred to as 40kDa TNF inhibitor a Δ51 and 40kDa TNF inhibitor Δ53. All portions of this application which refer generally to 40kDa TNF inhibitor shall encompass the mature 40kDa protein isolated from medium conditioned by human U937 cells and identified in urine, as well as 40kDa TNF inhibitor Δ51 and 40kDa TNF inhibitor Δ53.

It is generally believed that at least one TNF receptor is capable of binding both TNF alpha and TNF beta, while some TNF receptors are capable of only binding TNF alpha. This is consistent with the findings in the present invention wherein two TNF inhibitors have been identified which are both proposed to be active fragments of TNF receptor sites, and one is active against only TNF alpha and the other is active against both TNF alpha and TNF beta.

5. Recombinant Inhibitor (a) General

A recombinant DNA method for the manufacture of a TNF inhibitor is now disclosed. In one embodiment of the invention, the active site functions in a manner biologically equivalent to that of the TNF inhibitor isolated from urine. A natural or synthetic DNA sequence may be used to direct production of such TNF inhibitors. This method comprises:

(a) preparation of a DNA sequence capable of directing a host cell to produce a protein having TNF inhibitor activities or a precursor thereof;

(b) cloning the DNA sequence into a vector capable of being transferred into and replicated in a host cell, such vector containing operational elements needed to express the DNA sequence or a precursor thereof;

(c) transferring the vector containing the synthetic DNA sequence and operational elements into a host cell capable of expressing the DNA encoding TNF inhibitor or a precursor thereof;

(d) culturing the host cells under the conditions for amplification of the vector and expression of the inhibitor or a precursor thereof;

(e) harvesting the inhibitor or a precursor thereof; and (f) permitting the inhibitor to assume an active tertiary structure whereby it possesses or can be processed into a protein having TNF inhibitory activity.

In one embodiment of the present invention, the TNF inhibitor is produced by the host cell in the form of a precursor protein. This precursor protein is processed to a protein in one or more steps and allowed to fold correctly to an active TNF inhibitor using methods generally known to those of ordinary skill in the art.

(b) DNA Sequences

DNA sequences contemplated for use in this method are discussed in part in Examples 6, 14A, and 17. It is contemplated that these sequences include synthetic and natural DNA sequences and combinations thereof. The natural sequences further include cDNA or genomic DNA segments.

The means for synthetic creation of polynucleotide sequences encoding a protein identical to that encoded by the cDNA or genomic polynucleotide sequences are generally known to one of ordinary skill in the art, particularly in light of the teachings contained herein. As an example of the current state of the art relating to polynucleotide synthesis, one is directed to Matteucci, M. D., and Caruthers, M. H., in J. Am. Chem. Soc. 103:3185 (1981) and Beaucage, S. L. and Caruthers, M. H. in Tetrahedron Lett. 22:1859 (1981), and to the instructions supplied with an ABI oligonucleotide synthesizer, each of which is specifically incorporated herein by reference.

These synthetic sequences may be identical to the natural sequences described in more detail below or they may contain different nucleotides. In one embodiment, if the synthetic sequences contain nucleotides different from those found in the natural DNA sequences of this invention, it is contemplated that these different sequences will still encode a polypeptide which has the same primary structure as TNF inhibitor isolated from urine. In an alternate embodiment, the synthetic sequence containing different nucleotides will encode a polypeptide which has the same biological activity as the TNF inhibitor described herein.

Additionally, the DNA sequence may be a fragment of a natural sequence, i.e., a fragment of a polynucleotide which occurred in nature and which has been isolated and purified for the first time by the present inventors. In one embodiment, the DNA sequence is a restriction fragment isolated from a cDNA library.

In an alternative embodiment, the DNA sequence is isolated from a human genomic library. An example of such a library useful in this embodiment is set forth by Wyman, et al., (1985) Proc. Nat. Acad. Sci. USA, 82, 2880–2884.

In a preferred version of this embodiment, it is contemplated that the natural DNA sequence will be obtained by a method comprising:

(a) Preparation of a human cDNA library from cells, preferably U937 cells capable of generating a TNF inhibitor, in a vector and a cell capable of amplifying and expressing all or part of that cDNA;

(b) Probing the human DNA library with at least one probe capable of binding to the TNF inhibitor gene or its protein product;

(c) Identifying at least one clone containing the gene coding for the inhibitor by virtue of the ability of the clone to bind at least one probe for the gene or its protein product;

(d) Isolation of the gene or portion of the gene coding for the inhibitor from the clone or clones chosen; and (e) Linking the gene, or suitable fragments thereof, to operational elements necessary to maintain and express the gene in a host cell.

The natural DNA sequences useful in the foregoing process may also be identified and isolated through a method comprising:

(a) Preparation of a human genomic library, preferably propagated in a recBC,sbc host, preferably CES 200;

(b) Probing the human genomic library with at least one probe capable of binding a TNF inhibitor gene or its protein product;

(c) Identification of at least one clone containing the gene coding for the inhibitor by virtue of the ability of the clone to bind at least one probe for the gene or its protein product;

(d) Isolation of the gene coding for the inhibitor from the clone or clones identified; and (e) Linking the gene, or suitable fragments thereof, to operational elements to maintain and express the gene in a host cell.

A third potential method for identifying and isolating natural DNA sequences useful in the foregoing process includes the following steps:

(a) Preparation of mRNA from cells that produce the TNF inhibitor;

(b) Synthesizing cDNA (single- or double-stranded) from this mRNA;

(c) Amplifying the TNF inhibitor-specific DNA sequences present in this mixture of cDNA sequences using the polymerase chain reaction (PCR) procedure with primers such as those shown in Table 5;

(d) Identifying the PCR products that contain sequences present in the other oligonucleotide probes shown in Table 5 using Southern blotting analysis;

(e) Subcloning the DNA fragments so identified into M13 vectors that allow direct sequencing of the DNA sequences;

(f) Using these sequences to isolate a cDNA clone from a cDNA library; and (g) Linking the gene, or suitable fragments thereof, to operational elements necessary to maintain and express the gene in host cells.

In isolating a DNA sequence suitable for use in the above-method, it is preferred to identify the two restriction sites located within and closest to the end portions of the appropriate gene or sections of the gene that encode the native protein or fragments thereof. The DNA segment containing the appropriate gene or sections of the gene is then removed from the remainder of the genomic material using appropriate restriction endonucleases. After excision, the 3' and 5' ends of the DNA sequence and any intron exon junctions are reconstructed to provide appropriate DNA sequences capable of coding for the N- and C-termini and the body of the TNF inhibitor protein and capable of fusing the DNA sequence to its operational elements.

As described in Example 17 below, the DNA sequence utilized for the expression of 40kDa TNF inhibitor may be modified by the removal of either 153 or 159 base pairs from the gene that encodes for the mature 40kDa TNF inhibitor isolated from medium conditioned by human U937 cells and identified in urine. The Δ53 gene was prepared to remove the proline region from the C-terminus of the full gene, and the Δ51 gene was prepared to approximate the C-terminus of the gene encoding for 30kDa TNF inhibitor.

A DNA sequence, isolated according to these methods from a cDNA library and encoding at least a portion of the 30kDa TNF inhibitor described herein, has been deposited at the American Type Culture Collection, Rockville, Md., under Accession No 40645.

A DNA sequence, isolated according to these methods from a human genomic DNA library and encoding at least a portion of the 30kDa TNF inhibitor described herein, has been deposited at the American Type Culture Collection, Rockville, Md., under Accession No. 40620.

A DNA sequence, isolated according to these methods from a cDNA library and encoding at least a portion of the 40kDa TNF inhibitor described herein, has been deposited at the American Type Culture Collection, Rockville, Md. under Accession No. 68204.

6. Vectors (a) Microorganisms, Especially *E. coli*

The vectors contemplated for use in the present invention include any vectors into which a DNA sequence as discussed above can be inserted, along with any preferred or required operational elements, and which vector can then be subsequently transferred into a host cell and replicated in such cell. Preferred vectors are those whose restriction sites have been well documented and which contain the operational elements preferred or required for transcription of the DNA sequence. However, certain embodiments of the present invention are also envisioned which employ currently undiscovered vectors which would contain one or more of the cDNA sequences described herein. In particular, it is preferred that all of these vectors have some or all of the following characteristics: (1) possess a minimal number of host-organism sequences; (2) be stably maintained and propagated in the desired host; (3) be capable of being present in a high copy number in the desired host; (4) possess a regulatable promoter positioned so as to promote transcription of the gene of interest; (5) have at least one marker DNA sequence coding for a selectable trait present on a portion of the plasmid separate from that where the DNA sequence will be inserted; and (6) a DNA sequence capable of terminating transcription.

In variously preferred embodiments, these cloning vectors containing and capable of expressing the DNA sequences of the present invention contain various operational elements. These "operational elements," as discussed herein, include at least one promoter, at least one Shine-Dalgarno sequence and initiator codon, and at least one terminator codon. Preferably, these "operational elements" also include at least one operator, at least on leader sequence for proteins to be exported from intracellular space, at least one gene for a regulator protein, and any other DNA sequences necessary or preferred for appropriate transcription and subsequent translation of the vector DNA.

Certain of these operational elements may be present in each of the preferred vectors of the present invention. It is contemplated that any additional operational elements which may be required may be added to these vector using methods known to those of ordinary skill in the art, particularly in light of the teachings herein.

In practice, it is possible to construct each of these vectors in a way that allows them to be easily isolated, assembled and interchanged. This facilitates assembly of numerous functional genes from combinations of these elements and the coding region of the DNA sequences. Further, many of these elements will be applicable in more than one host. It is additionally contemplated that the vectors, in certain preferred embodiments, will contain DNA sequences capable of functioning as regulators ("operators"), and other DNA sequences capable of coding for regulator proteins.

(i) Regulators

These regulators, in one embodiment, will serve to prevent expression of the DNA sequence in the presence of certain environmental conditions and, in the presence of other environmental conditions, will allow. transcription and subsequent expression of the protein coded for by the DNA sequence. In particular, it is preferred that regulatory segments be inserted into the, vector such that expression of the DNA sequence will not occur, or will occur to a greatly reduced extent, in the absence of, for example, isopropylthio-beta-D-galactoside. In this situation, the transformed microorganisms containing the DNA sequence may be grown to a desired density prior to initiation of the expression of TNF inhibitor. In this embodiment, expression of the desired protein is induced by addition of a substance to the microbial environment capable of causing expression of the DNA sequence after the desired density has been achieved.

(ii) Promoters

The expression vectors must contain promoters which can be used by the host organism for expression of its own proteins. While the lactose promoter system is commonly used, other microbial promoters have been isolated and characterized, enabling one skilled in the art to use them for expression of the recombinant TNF inhibitor.

(iii) Transcription Terminator

The transcription terminators contemplated herein serve to stabilize the vector. In particular, those sequences as described by Rosenberg, M. and Court, D., in Ann. Rev. Genet. 13:319–353 (1979), specifically incorporated herein by reference, are contemplated for use in the present invention.

(iv) Non-Translated Sequence

It is noted that, in the preferred embodiment, it may also be desirable to reconstruct the 3' or 5' end of the coding region to allow incorporation of 3' or 5' non-translated sequences into the gene transcript. Included among these non-translated sequences are those which stabilize the mRNA as they are identified by Schrneissner, U., McKenney, K., Rosenberg, M and Court, D. in J. Mol. Biol. 176:39–53 (1984), specifically incorporated herein by reference.

(v) Ribosome Binding Sites

The microbial expression of foreign proteins requires certain operational elements which include, but are not limited to, ribosome binding sites. A ribosome binding site is a sequence which a ribosome recognizes and binds to in the initiation of protein synthesis as set forth in Gold, L., et al., Ann. Rev. Microbio. 35:557–580; or Marquis, D. M., et al., Gene 42:175–183 (1986), both of which are specifically incorporated herein by reference. A preferred ribosome binding site is GAGGCGCAAAAA(ATG).

(vi) Leader Sequence and Translational Coupler

Additionally, it is preferred that DNA coding for an appropriate secretory leader (signal) sequence be present at the 5' end of the DNA sequence as set forth by Watson, M. E. in Nucleic Acids Res. 12:5145–5163, specifically incorporated herein by reference, if the protein is to be excreted from the cytoplasm. The DNA for the leader sequence must be in a position which allows the production of a fusion protein in which the leader sequence is immediately adjacent to and covalently joined to the inhibitor, i.e., there must be no transcription or translation termination signals between the two DNA coding sequences. The presence of the leader sequence is desired in part for one or more of the following reasons. First, the presence of the leader sequence may facilitate host processing of the TNF inhibitor. In particular, the leader sequence may direct cleavage of the initial translation product by a leader peptidase to remove the leader sequence and leave a polypeptide with the amino acid sequence which has potential protein activity. Second, the presence of the leader sequence may facilitate purification of the TNF inhibitor, through directing the protein out of the cell cytoplasm. In some species of host microorganisms, the presence of an appropriate leader sequence will allow transport of the completed protein into the periplasmic space, as in the case of some E. coli. In the case of ceratin E. coli, Saccharomyces and strains of Bacillus and Pseudomonas, the appropriate leader sequence will allow transport of the protein through the cell membrane and into the extracellular medium. In this situation, the protein may be purified from extracellular protein. Thirdly, in the case of some of the proteins prepared by the present invention, the presence of the leader sequence may be necessary to locate the completed protein in an environment where it may fold to assume its active structure, which structure possesses the appropriate protein activity.

In one preferred embodiment of the present invention, an additional DNA sequence is located immediately preceding the DNA sequence which codes for the TNF inhibitor. The additional DNA sequence is capable of functioning as a translational coupler, i.e., it is a DNA sequence that encodes an RNA which serves to position ribosomes immediately adjacent to the ribosome binding site of the inhibitor RNA with which it is contiguous. In one embodiment of the present invention, the translational coupler may be derived using the DNA sequence TAACGAGGCGCAAAAAAT-GAAAAAGACAGCTATCGCGATCTTGGAG-GATGATTAAATG and methods currently known to those of ordinary skill in the art related to translational couplers.

(vii) Translation Terminator

The translation terminators contemplated herein serve to stop the translation of mRNA. They may be either natural, as described by Kohli, J., Mol. Gen. Genet. 182:430–439; or synthesized, as described by Pettersson, R. F. Gene 24:15–27 (1983), both of which references are specifically incorporated herein by reference.

(viii) Selectable Marker

Additionally, it is preferred that the cloning vector contain a selectable marker, such as a drug resistance marker or other marker which causes expression of a selectable trait by the host microorganism. In one embodiment of the present invention, the gene for ampicillin resistance is included in the vector while, in other plasmids, the gene for tetracycline resistance or the gene for chloramphenicol resistance is included.

Such a drug resistance or other selectable marker is intended in part to facilitate in the selection of transformants. Additionally, the presence of such a selectable marker in the cloning vector may be of use in keeping contaminating microorganisms from multiplying in the culture medium. In this embodiment, a pure culture of the transformed host microorganisms would be obtained by culturing the microorganisms under conditions which require the induced phenotype for survival.

The operational elements as discussed herein are routinely selected by those or ordinary skill in the art in light of prior literature and the teachings contained herein. General examples of these operational elements are set forth in B. Lewin, Genes, Wiley & Sons, New York (1983), which is specifically incorporated herein by reference. Various examples of suitable operational elements may be found on the vectors discussed above and may be elucidated through review of the publications discussing the basic characteristics of the aforementioned vectors.

Upon synthesis and isolation of all necessary and desired component parts of the above-discussed vector, the vector is assembled by methods generally known to those of ordinary skill in the art. Assembly of such vectors is believed to be within the duties and tasks performed by those with ordinary skill in the art and, as such, is capable of being performed without undue experimentation. For example, similar DNA sequences have been ligated into appropriate cloning vectors, as set forth by Maniatis et al. in Molecular Cloning, Cold Spring Harbor Laboratories (1984), which is specifically incorporated herein by reference.

In construction of the cloning vectors of the present invention, it should additionally be noted that multiple copies of the DNA sequence and its attendant operational elements may be inserted into each vector. In such an embodiment, the host organism would produce greater amounts per vector of the desired TNF inhibitor. The number of multiple copies of the DNA sequence which may be inserted into the vector is limited only by the ability of the resultant vector, due to its size, to be transferred into and replicated and transcribed in an appropriate host cell.

(b) Other Microorganisms

Vectors suitable for use in microorganisms other than E. coli are also contemplated for this invention. Such vectors are described in Table 1. In addition, certain preferred vectors are discussed below.

TABLE 1

| HOSTS | REGULATED PROMOTERS | INDUCER | TRANSCRIPTION TERMINATOR | MRNA STABILIZATION | TRANSCRIPTIONAL START SITE & LEADER PEPTIDE | RS MARKER | BINDING SITE |
|---|---|---|---|---|---|---|---|
| E. coli | Lac[1], Tac[2] Lambda pL Trp[5] | IPTG increased temperature IAA addition or tryptophan depletion | rrnB[6] rrnC[7] | ompA[8] lambda int[9] trp[10] | bla[11] ompA[12] phoS | ampicillin[14] tetracycline[14,15] chlor-amphenical[16] | |
| Bacillus | *alpha amylase[17] *subtilisin[18] *p-43[19] spac-1[26] | IPTG | E. coli rrn rrn BT.T[20] | | B. amy neutral protease[21] B. amy alpha-amylase[22] B. subt. subtilisin[23] phospholipase C[28] exotoxin A[28] | Kan$^r$ [24] Cam$^r$ [25] | B. amy neural protease B. amy alpha-amylase[22] |
| Pseudo-monas | Trp[27] (E. coli) Lac (E. coli) Tac (E. coli) | IAA addition, or tryptophan depletion IPTG | | | phospholipase C[28] exotoxin A[28] | sulfonamide[30] streptomycin[30] | Trp (E. coli) |
| Yeast | Gal 1[31], 10[32] | Glucose depletion and | Cyc1 Una | | Invertase[36] Acid phosphatase[36] | Ura 3[37] Leu 2[38] | |

TABLE 1-continued

| REGULATED HOSTS | PROMOTERS | INDUCER | TRANSCRIPTION TERMINATOR | MRNA STABILIZATION | TRANSCRIPTIONAL START SITE & LEADER PEPTIDE | MARKER | RS BINDING SITE |
|---|---|---|---|---|---|---|---|
| | Adb $1^{33}$, $11^{34}$ Pho 5 | galactose Glucose depletion Phosphate depletion | Alpha Factor Sac 2 | | Alpha factor | His 3 Tap 1 | |

*non-regulated

1. Backman, K., Ptashne, M. and Gilbert, W. Proc. Natl. Acad. Sci. USA 73, 4174–4178 (1976).
2. de Boer, H. A., Comstock, L. J., and Vasser, M. Proc. Natl. Acad. Sci. USA 80, 21–25 (1983).
3. Shimatake, H. and Rosenberg, M. Nature 292, 128–132 (1981).
4. Derom, C., Gheysen, D. and Fiers, W. Gene 17, 45–54 (1982).
5. Hallewell, R. A. and Emtage, S. Gene 9, 27–47 (1980).
6. Brosius, J., Dull, T. J., Sleeter, D. D. and Noller, H. F. J. Mol. Biol. 148 107–127 (1981).
7. Normanly, J., Ogden, R. C., Horvath, S. J. and Abelson, J. Nature 321, 213–219 (1986).
8. Belasco, J. G., Nilsson, G., von Gabain, A. and Cohen, S. N. Cell 46, 245–251 (1986).
9. Schmeissner, U., McKenney, K., Rosenberg M. and Court, D. J. Mol. Biol. 176, 39–53 (1984).
10. Mott, J. E., Galloway, J. L. and Platt, T. EMBO J. 4, 1887–1891 (1985).
11. Koshland, D. And Botstein, D. Cell 20, 749–760 (1980).
12. Movva, N. R., Kakamura, K. and Inouye, M. J. Mol. Biol. 143, 317–328 (1980).
13. Surin, B. P., Jans, D. A., Fimmel, A. L., Shaw, D. C., Cox, G. B. and Rosenberg, H. J. Bacteriol. 157, 772–778 (1984).
14. Sutcliffe, J. G. Proc. Natl. Acad. Sci. USA 75, 3737–3741 (1978).
15. Peden, K. W. C. Gene 22, 277–280 (1983).
16. Alton, N. K. and Vapnek, D. Nature 282, 864–869 (1979).
17. Yang, M., Galizzi, A., and Henner, D. Nuc. Acids Res. 11(2), 237–248 (1983).
18. Wong, S.-L., Price C. W., Goldfarb, D. S., and Doi, R. H. Proc. Natl. Acad. Sci. USA 81, 1184–1188 (1984).
19. Wang, P.-Z. and Doi, R. H. J. Biol. Chem. 251, 8619–8625, (1984).
20. Lin, C.-K., Quinn, L. A., Rodriguez, R. L. J. Cell Biochem. Suppl. (9B), p. 198 (1985).
21. Vasantha, N., Thompson, L. D., Rhodes, C., Banner, C., Nagle, J., and Filpula, D. J. Bact. 159(3), 811–819 (1984).
22. Plava, I., Sarvas, M., Lehtovaara, P., Sibazkov, M., and Kaariainen, L. Proc. Natl. Acad. Sci. USA 79, 5582–5586 (1982).
23. Wong. S.-L., Pricee, C. W., Goldfarb, D. S., and Doi, R. H. Proc. Natl. Acad. Sci. USA 81, 1184–1188 (1984).
24. Sullivan, M. A., Yasbin, R. E., Young, F. E. Gene 29, 21–46 (1984).
25. Vasantha, N., Thompson, L. D., Rhodes, C., Banner, C. Nagle, J., and Filula, D. J. Bact. 159(3), 811–819 (1984).
26. Yansura, D. G. and Henner, D. J. PNAS 81, 439–443 (1984).
27. Gray, G. L., McKeown, K. A., Jones, A. J. S., Seeburg, P. H. and Heyneker, H. L. Biotechnology, 161–165 (1984).
28. Lory, S., and Tai, P. C. Gene 22, 95–101 (1983).
29. Liu, P. V. J. Infect. Dis. 130 (suppl), 594–599 (1974).
30. Wood, D. G., Hollinger, M. F., and Tindol, M. B. J. Bact. 145, 1448–1451 (1981).
31. St. John, T. P. and Davis, R. W. J. Mol. Biol. 152, 285–315 (1981).
32. Hopper, J. E., and Rowe, L. B. J. Biol. Chem. 253, 7566–7569 (1978).
33. Denis, C. L., Ferguson, J. and Young, E. T. J. Biol. Chem. 258, 1165–1171 (1983).
34. Lutsdorf, L. and Megnet, R. Archs. Biochem. Biophys. 126, 933–944 (1968).
35. Meyhack, B., Bajwa, N., Rudolph, H. and Hinnen, A. EMBO. J. 6, 675–680 (1982).
36. Watson, M. E. Nucleic Acid Research 12, 5145–5164 (1984).
37. Gerband, C. and Guerineau, M. Curr. Genet. 1, 219–228 (1980).
38. Hinnen, A., Hicks, J. B. and Fink, G. R. Proc. Natl. Acad. Sci. USA 75, 1929–1933 (1978).
39. Jabbar, M. A., Sivasubramanian, N. and Nayak, D. P. Proc. Natl. Acad. Sci. USA 82, 2019–2023 (1985).

(i)Pseudomonas Vectors

Several vector plasmids which autonomously replicate in a broad range of Gram negative bacteria are preferred for use as cloning vehicles in hosts of the genus Pseudomonas. Certain of these are described by Tait, R. C., Close, T. J., Lundquist, R. C., Hagiya, M., Rodriguez, R. L., and Kado, C. I. in Biotechnology, May, 1983, pp. 269–275; Panopoulos, N.J. in *Genetic Engineering in the Plant Sciences*, Praeger Publishers, New York, N.Y., pp. 163–185 (1981); and Sakagucki, K. in Current Topics in Microbiology and Immunology 96:31–45 (1982), each of which is specifically incorporated herein by reference.

One particularly preferred construction would employ the plasmid RSF1010 and derivatives thereof as described by Bagdasarian, M., Bagdasarian, M. M., Coleman, S., and Timmis, K. N. in *Plasmids of Medical, Environmental and Commercial Importance*, Timmis, K. N. and Puhler, A. eds., Elsevier/North Holland Biomedical Press (1979), specifically incorporated herein by reference. The advantages of RSF1010 are that it is a relatively small, high copy number plasmid which is readily transformed into and stably maintained in both *E. coli* and Pseudomonas species. In this system, it would be preferred to use the Tac expression system as described for Escherichia, since it appears that the *E. coli* trp promoter is readily recognized by Pseudomonas RNA polymerase as set forth by Sakagucki, K. in Current Topics in Microbiology and Immunology 96:31–45 (1982) and Gray, G. L., McKeown, K. A., Jones A. J. S., Seeburg, P. H., and Heyneker, H. L. in Biotechnology, Febuary 1984, pp. 161–165, both of which are specifically incorporated herein by reference. Transcriptional activity may be further maximized by requiring the exchange of the promoter with, e.g., an *E. coli* or *P. aeruginosa* trp promoter. Additionally, the lacI gene of *E. coli* would also be included in the plasmid to effect regulation.

Translation may be coupled to translation initiation for any of the Pseudomonas proteins, as well as to initiation sites for any of the highly expressed proteins of the type chosen to cause intracellular expression of the inhibitor.

In those cases where restriction minus strains of a host Pseudomonas species are not available, transformation efficiency with plasmid constructs isolated from *E. coli* are poor. Therefore, passage of the Pseudomonas cloning vector through an r– m+ strain of another species prior to transformation of the desired host, as set forth in Bagdasarian, M., et al., *Plasmids of Medical, Environmental and Commercial Importance*, pp. 411–422, Timmis and Puhler eds., Elsevier/North Holland Biomedical Press (1979), specifically incorporated herein by reference, is desired.

(ii) Bacillus Vectors

Furthermore, a preferred expression system in hosts of the genus Bacillus involves using plasmid pUB110 as the cloning vehicle. As in other host vector systems, it is possible in Bacillus to express the TNF inhibitor of the present invention as either an intracellular or a secreted protein. The present embodiments include both systems. Shuttle vectors that replicate in both Bacillus and *E. coli* are available for constructing and testing various genes as described by Dubnau, D., Gryczan, T., Contente, S., and Shivakumar, A. G. in Genetic Engineering, Vol. 2, Setlow and Hollander eds., Plenum Press, New York, N.Y., pp. 115–131 (1980), specifically incorporated herein by reference. For the expression and secretion of the TNF inhibitor from *B. subtilis*, the signal sequence of alpha-amylase is preferably coupled to the coding region for the protein. For synthesis of intracellular inhibitor, the portable DNA sequence will be translationally coupled to the ribosome binding site of the alpha-amylase leader sequence.

Transcription of either of these constructs is preferably directed by the alpha-amylase promoter or a derivative thereof. This derivative contains the RNA polymerase recognition sequence of the native alpha-amylase promoter but incorporates the lac operator region as well. Similar hybrid promoters constructed from the penicillinase gene promoter and the lac operator have been shown to function in Bacillus hosts in a regulatable fashion as set forth by Yansura, D. G. and Henner in *Genetics and Biotechnology of Bacilii*, Ganesan, A. T. and Hoch, J. A., eds., Academic Press, pp. 249–263 (1984), specifically incorporated by reference. The laci gene of *E. coli* would also be included in the plasmid to effect regulation.

(iii) Clostridium Vectors

One preferred construction for expression in Clostridium is in plasmid pJU12, described by Squires, C. H. et al., in J. Bacteriol. 159:465–471 (1984) and specifically incorporated herein by reference, transformed into *C. perfringens* by the method of Heefner, D. L. et al., as described in J. Bacteriol. 159:460–464 (1984), specifically incorporated herein by reference. Transcription is directed by the promoter of the tetracycline resistance gene. Translation is coupled to the Shine-Dalgarno sequences of this same tet gene in a manner strictly analogous to the procedures outlined above for vectors suitable for use in other hosts.

(iv) Yeast Vectors

Maintenance of foreign DNA introduced into yeast can be effected in several ways as described by Botstein, D. and Davis, R. W., in *The Molecular Biology of the Yeast Saccharomyces*, Cold Spring Harbor Laboratory, Strathern, Jones and Broach, eds., pp. 607–636 (1982), specifically incorporated herein by reference. One preferred expression system for use with host organisms of the genus Saccharomyces harbors the TNF inhibitor gene on the 2 micron plasmid. The advantages of the 2 micron circle include relatively high copy number and stability when introduced into cir' strains. These vectors preferably incorporate the replication origin and at least one antibiotic resistance marker from pBR322 to allow replication and selection in *E. coli*. In addition, the plasmid will preferably have the two micron sequence and the yeast LEU2 gene to serve the same purposes in LEU2 defective mutants of yeast.

If it is contemplated that the recombinant TNF inhibitors will ultimately be expressed in yeast, it is preferred that the cloning vector first be transferred into *Escherichia coli*, where the vector would be allowed to replicate and from which the vector would be obtained and purified after amplification. The vector would then be transferred into the yeast for ultimate expression of the TNF inhibitor.

(c) Mammalian Cells

The cDNA for the TNF inhibitor will serve as the gene for expression of the inhibitor in mammalian cells. It should have a sequence that will be efficient at binding ribosomes such as that described by Kozak, in Nucleic Acids Research 15:8125–8132 (1987), specifically incorporated herein by reference, and should have coding capacity for a leader sequence (see section 3(a)(vi)) to direct the mature protein out of the cell in a processed form. The DNA restriction fragment carrying the complete cDNA sequence can be inserted into an expression vector which has a transcriptional promoter and a transcriptional enhancer as described by Guarente, L. in Cell 52:303–305 (1988) and Kadonaga, J. T. et al., in Cell 51:1079–1090 (1987), both of which are specifically incorporated herein by reference. The promoter may be regulatable as in the plasmid pMSG (Pharmacia Cat. No. 27450601) if constitutive expression of the inhibitor is harmful to cell growth. The vector should have a complete polyadenylation signal as described by Ausubel, F. M. et al. in Current Protocols in Molecular Biology, Wiley (1987), specifically incorporated herein by reference, so that the mRNA transcribed from this vector is processed properly. Finally, the vector will have the replication origin and at least one antibiotic resistance marker from pBR322 to allow replication and selection in *E. coli*.

In order to select a stable cell line that produces the TNF inhibitor, the expression vector can carry the gene for a selectable marker such as a drug resistance marker or carry a complementary gene for a deficient cell line, such as a dihydrofolate reductase (dhfr) gene for transforming a dhfr cell line as described by Ausubel et al., supra. Alternatively, a separate plasmid carrying the selectable marker can be cotransformed along with the expression vector.

7. Host Cells/Transformation

The vector thus obtained is transferred into an appropriate host cell. These host cells may be microorganisms or mammalian cells.

(a) Microorganisms

It is believed that any microorganism having the ability to take up exogenous DNA and express those genes and attendant operational elements may be chosen. After a host organism has been chosen, the vector is transferred into the host organism using methods generally known to those of ordinary skill in the art. Examples of such methods may be found in Advanced Bacterial Genetics by R. W. Davis et al., Cold spring Harbor Press, Cold Spring Harbor, N.Y., (1980), which is specifically incorporated herein by reference. It is preferred, intone embodiment, that the transformation occur at low temperatures, as temperature regulation is contemplated as a means of regulating gene expression through the use of operational elements as set forth above. In another embodiment, if osmolar regulators have been inserted into the vector, regulation of the salt concentrations during the transformation would be required to insure appropriate control of the foreign genes.

It is preferred that the host microorganism be a facultative anaerobe or an aerobe. Particular hosts which may be preferable for use in this method include yeasts and bacteria. Specific yeasts include those of the genus Saccharomyces, and especially *Saccharomyces cerevisiae*. Specific bacteria include those of the genera Bacillus, Escherichia, and Pseudomonas, especially *Bacillus subtilis* and *Escherichia coli*. Additional host cells are listed in Table I, supra.

(b) Mammalian Cells

The vector can be introduced into mammalian cells in culture by several techniques such as calcium phosphate: DNA coprecipitation, electroporation, or protoplast fusion. The preferred method is coprecipitation with calcium phosphate as described by Ausubel et al., sudra.

Many stable cell types exist that are transformable and capable of transcribing and translating the cDNA sequence, processing the precursor TNF inhibitor and secreting the mature protein. However, cell types may be variable with regard to glycosylation of secreted proteins and post-translational modification of amino acid residues, if any. Thus, the ideal cell types are those that produce a recombinant TNF inhibitor identical to the natural molecule.

8. Culturing Engineered Cells

The host cells are cultured under conditions appropriate for the expression of the TNF inhibitor. These conditions are generally specific for the host cell, and are readily determined by one of ordinary skill in the art in light of the published literature regarding the growth conditions for such cells and the teachings contained herein. For example, Bergey's Manual of Determinative Bacteriology, 8th Ed., Williams & Wilkins Company, Baltimore, Md., which is specifically incorporated herein by reference, contains information on conditions for culturing bacteria. Similar information on culturing yeast and mammalian cells may be obtained from Pollack, R. Mammalian Cell Culture, Cold Spring Harbor Laboratories (1975), specifically incorporated herein by reference.

Any conditions necessary for the regulation of the expression of the DNA sequence, dependent upon any operational elements inserted into or present in the vector, would be in effect at the transformation and culturing stages. In one embodiment, cells are grown to a high density in the presence of appropriate regulatory conditions which inhibit the expression of the DNA sequence. When optimal cell density is approached, the environmental conditions are altered to those appropriate for expression of the DNA sequence. It is thus contemplated that the production of the TNF inhibitor will occur in a time span subsequent to the growth of the host cells to near optimal density, and that the resultant TNF inhibitor will be harvested at some time after the regulatory conditions necessary for its expression were induced.

9. Purification (a) TNF Inhibitor Produced From Microorganisms.

In a preferred embodiment of the present invention, the recombinant TNF inhibitor is purified subsequent to harvesting and prior to assumption of its active structure. This embodiment is preferred as the inventors believe that recovery of a high yield of re-folded protein is facilitated if the protein is first purified. However, in one preferred, alternate embodiment, the TNF inhibitor may be allowed to refold to assume its active structure prior to purification. In yet another preferred, alternate embodiment, the TNF inhibitor is present in its re-folded, active state upon recovery from the culturing medium.

In certain circumstances, the TNF inhibitor will assume its proper, active structure upon expression in the host microorganism and transport of the protein through the cell wall or membrane or into the periplasmic space. This will generally occur if DNA coding for an appropriate leader sequence has been linked to the DNA coding for the recombinant protein. If the TNF inhibitor does not assume its proper, active structure, any disulfide bonds which have formed and/or any noncovalent interactions which have occurred will first be disrupted by denaturing and reducing agents, for example, guanidinium chloride and beta-mercaptoethanol, before the TNF inhibitor is allowed to assume its active structure following dilution and oxidation of these agents under controlled conditions.

For purifications prior to and after refolding, some combinations of the following steps is preferably used; anion exchange chromatography (monoQ or DEAE-Sepharose), gel filtration chromatography (superose), chromatofocusing (MonoP), and hydrophobic interaction chromatography (octyl or phenyl sepharose). Of particular value will be affinity chromatography using TNF (described in Example 1).

(b) TNF Inhibitor Produced from Mammalian Cells.

TNF inhibitor produced from mammalian cells will be purified from conditioned medium by steps that will include ion exchange chromatography and affinity chromatography using TNF as described in Example 1. It will be apparent to those skilled in the art that various modifications and variations can be made in the processes and products of the present invention. Thus, it is intended that the present invention cover the modifications and variations of this invention provided they come within the scope of the appended claims and their equivalents.

As indicated previously, the TNF inhibitors of the present invention are contemplated for use as therapeutic agents and thus are to be formulated in pharmaceutically acceptable carriers. In one embodiment of the present invention, the TNF inhibitors may be chemically modified to improve the pharmokinetic properties of the molecules. An example would be the attachment of the TNF inhibitors to a high molecular weight polymeric material such as polyethylene glycol. In addition, interleukin-1 inhibitors may be administered in conjunction with the TNF inhibitors. This combination therapeutic will be especially useful in treatment of inflammatory and degenerative diseases.

The following examples illustrate various presently preferred embodiments of the invention claimed herein. All papers and references cited in the Examples that follow are specifically incorporated herein by reference.

Example 1

Protein Preparation

A. Materials

The gene for TNF alpha (TNFa) was purchased from British Biotechnology, Limited, Oxford, England. DEAE-Sepharose CL-6B resin and Mono-Q HR5/5, HR10/10 FPLC columns were purchased from Pharmacia, Inc., Piscataway, N.J. Affigel-15 resin, and BioRad protein assay kit were purchased from BioRad, Richmond, Calif., Tween 20, ammonium bicarbonate, sodium phosphate, PMSF, sodium bicarbonate, dithiothreitol crystal violet and actinomycin D were purchased from Sigma Chemical Company, St. Louis, Mo. Endoproteinase Lys-C, Endoproteinase Asp-N and TRIS were purchased from Boehringer Mannheim Biochemicals, Indianapolis, Ind. Hexafluoroacetone was purchased from ICN Biomedicals, Costa Mesa, Calif. Cyanogen bromide, trifluoroacetic acid, and guanidine hydrochloride were purchased from Pierce Chemicals, Rockford, Ill. Acetonitrile and HPLC water were purchased from J. T. Baker Chemical Company, Phillipsburg, N.J. Urea was purchased from Bethesda Research Laboratories, Gaithersburg, Md. [$^3$H]-Iodoacetic acid was purchased from New England Nuclear, Boston, Mass. [$^{125}$I]-TNFa was purchased from Amersham, Arlington Heights, Ill. Recombinant human TNFa was purchased from Amgen, Thousand Oaks, Calif. C8-reverse phase columns (25 cm×4.6 mm) were obtained from Synchrom, Inc., Lafayette, Ind. A C8-microbore reverse phase column (7 micron, 22 cm×2.1 mm) was obtained from Applied Biosystems, Foster City, Calif. Corning 96-well microtiter plates were purchased from VWR Scientific, Batavia, Ill. McCoys 5A media and fetal bovine serum were purchased from Gibco, Grand Island, N.Y. RPM-1 1640 media and L-glutamine were purchased from Mediatech, Herndon, Va. Trypsin was purchased from K. C. Biologicals, St. Lenexa, Kans. ME180, U937 and L929 cell lines were obtained from Amerlcan Type Culture Collection, Rockville, Md.

B. Assays for the TNF Inhibitor

Two types of assays were used to identify the TNF inhibitor. One of them is a cytotoxicity assay. The other is a gel shift assay.

1. Cytotoxicity Assay

The cytotoxicity assay was performed with actinomycin D-treated ME180 cells and L929 cells as described by Ostrove and Gifford (Proc. Soc. Exp. Biol. Med. 160, 354–358 (1979)) and Aggarwal and Essalu (J. Biol. Chem. 262, 10000–10007 (1987)). L929 cells (CCLI: American Type Culture Collection) cells were maintained in McCoy's 5A medium containing 10% fetal bovine serum. Confluent cultures were treated briefly with 0.25% trypsin in physiological solution containing 5mM EDTA and resuspended in a fresh medium. Approximately 2×10$^4$ trypsinized cells per well were plated in 96-Well plates (Corning) and incubated for 24 hours at 37° C. Then actinomycin D was added to a final concentration of 0.25 ug per ml. After two hours, samples containing TNF and TNF inhibitor were added to the wells and incubation was continued overnight at the same temperature. After microscopic evaluation, the medium was decanted, and the wells were rinsed with PBS. The wells were then filled with a solution of 0.1% crystal violet, 10% formaldehyde and 10 mM potassium phosphate, pH 6.0 for 5 min, washed thoroughly with water and dried. The dye was extracted with 0.1M sodium citrate in 50% ethanol, pH 4.2. The absorbance of the dye in viable cells was determined at 570 nm using a Kinetic microplate reader (Molecular Devices Corp. Calif.). An example of this assay is shown in FIG. 1. In the presence of TNF inhibitor, the cytotoxic effect of TNF was reduced.

2. Gel Shift Assay

Figure 2:
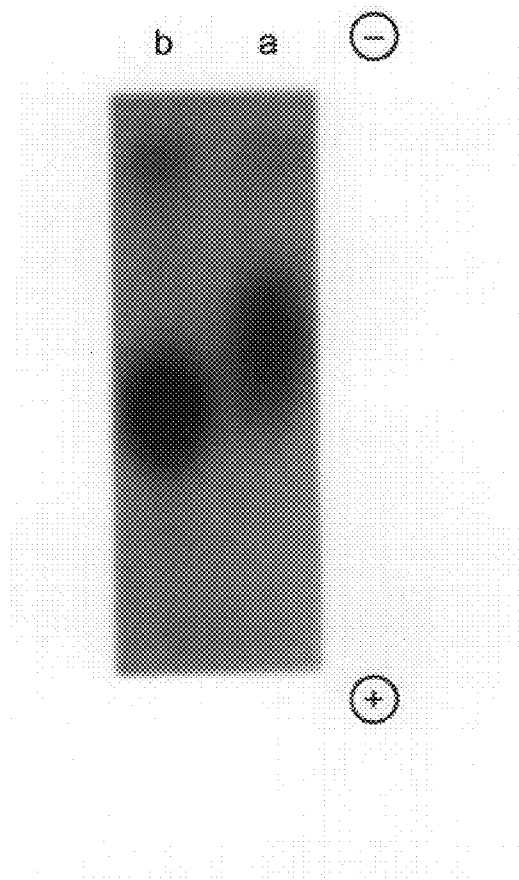

The gel shift assay involves the use of a native polyacrylamide gel electrophoresis system. This native 4% gel electrophoresis was performed according to Hedrick and Smith (Arch. Biochem. and Biophysics 126, 155–164 (1968)). The iodinated TNF (Amersham) was mixed with the TNF inhibitor from Example 1.C. after C8 chromatography and incubated for 30 min. to 2 hours. This mixture, along with the iodinated TNF alone, were loaded onto the 4% native gel and electrophoresed. After the gel was fixed with 10% acetic acid and washed, a film was placed for radioautography. As shown in FIG. 2, the complex of TNF and TNF inhibitor migrates differently from the TNF by itself. This gel shift assay was used to determine which fractions contain TNF inhibitor in the eluates of DEAE CL6B column chromatography.

C. Purification of the 30kDa TNF Inhibitor

Twenty liters of urine from a patient diagnosed with renal dysfunction was concentrated to 200 ml with an Amicon YM5 membrane. The concentrate was then dialyzed at 4° C. against 0.025 M Tris-HCl, pH 7.5, and subsequently centrifuged in a JA14 rotor at 10,000 rpm for 30 minutes. The supernatant was then loaded onto a 40×4.5 cm DEAE Sepharose CL-6B column equilibrated with 0.025 M Tris-HCl, pH 7.5 and extensively rinsed with equilibration buffer until the OD$_{280}$ of the effluent returned to baseline. Chromatography was accomplished using a linear gradient from 0–0.05 M sodium chloride in 0.025M Tris-HCl pH 7.5 and monitored by OD$_{280}$. Column fractions were collected, and assayed for TNF inhibitor activity using the native gel assay. The TNF inhibitor eluted elutes in a rather sharp peak at 80 mM NaCl.

Figure 6A:
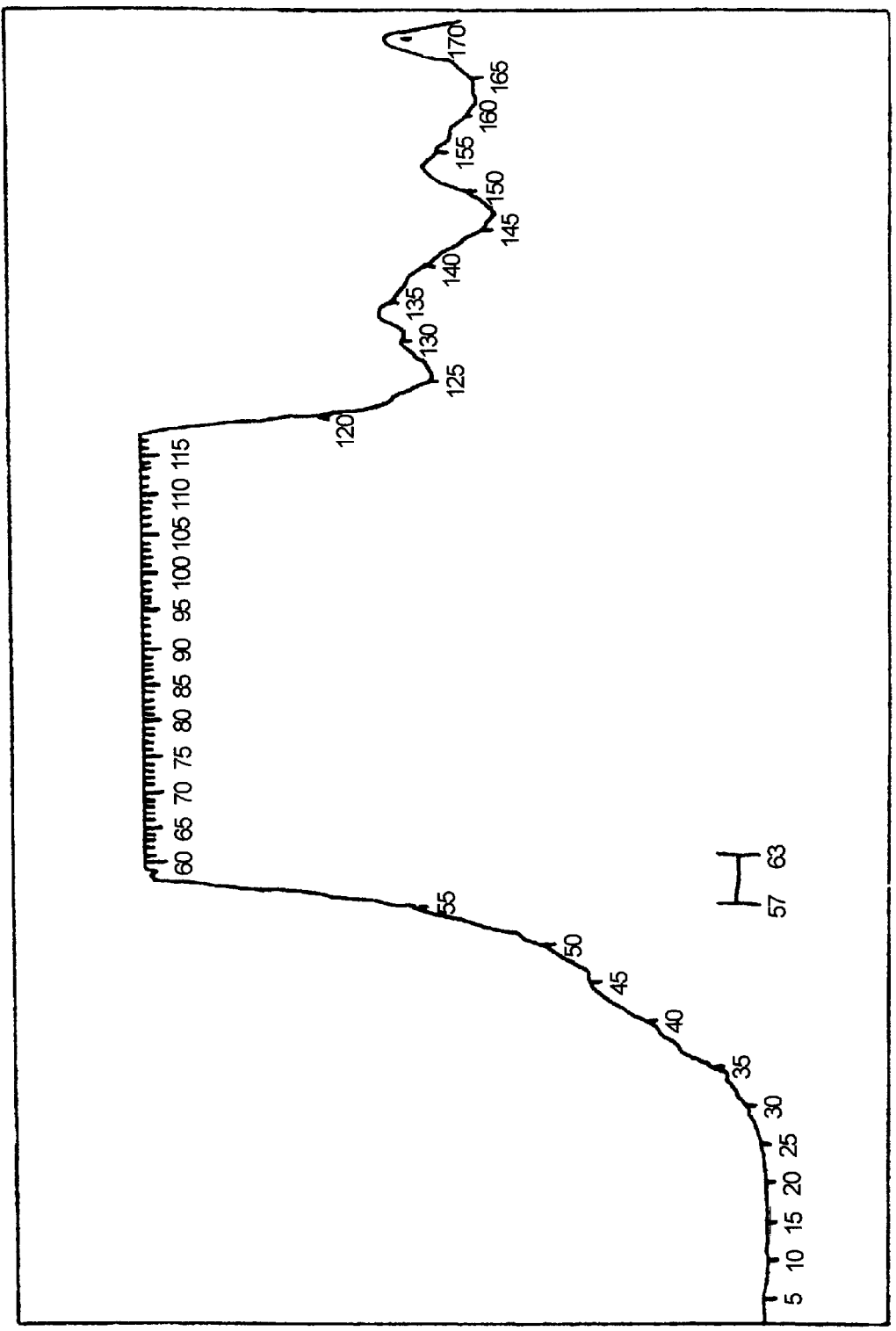
Figure 6B:
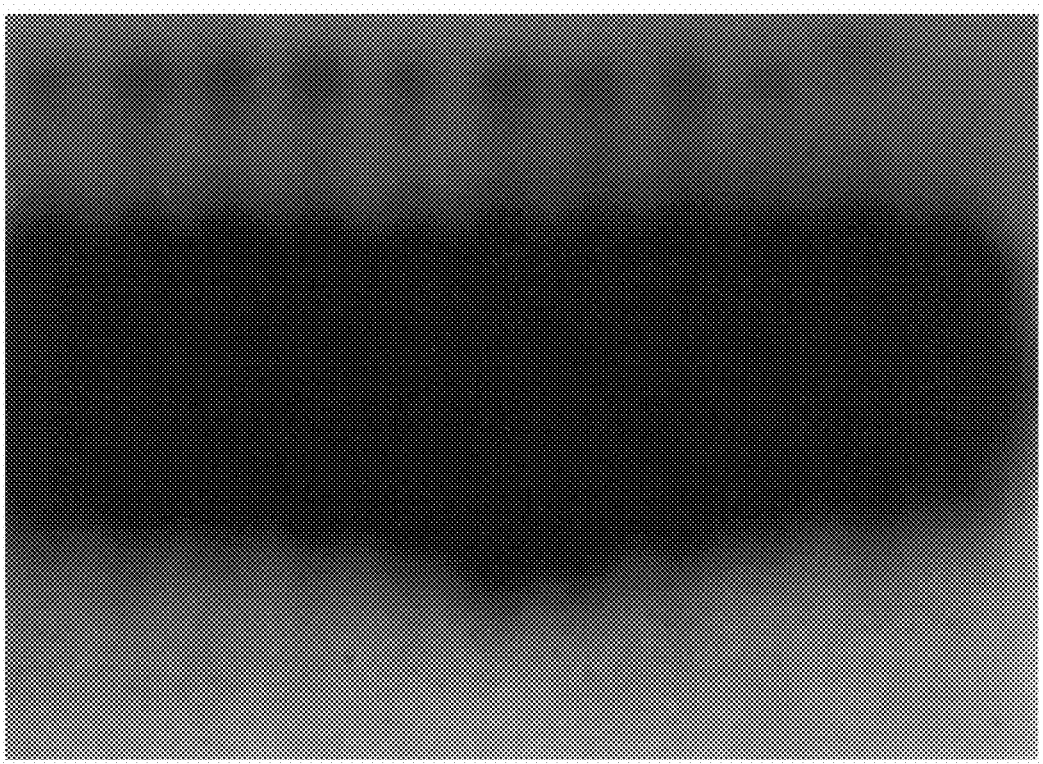

FIG. 6A shows the OD$_{280}$ profile of the DEAE Sepharose CL-6B chromatography of 20 1 urine. FIG. 6B shows the autoradiograph of the corresponding native gel assay indicating a peak of the TNF inhibitor at fractions 57–63, which is about 80 mM NaCl.

The TNF inhibitor was further purified using a TNF affinity column. Recombinant TNF was expressed in BL21/DE3 at about 10–20% total cell protein. The cell pellet was French-pressed at 20,000 psi and the soluble material dialyzed at 40° C. against 0.025 M Tris-HCl pH 8.0. The dialyzed lysate was 0.2 micron-filtered and loaded onto a Mono-Q FPLC column equilibrated with 0.025 M Tris-HCl ph 8.0. A linear gradient from 0 to 0.5 M NaCl in 0.025 M Tris-HCl pH 8.0 was run and monitored by OD$_{280}$. One ml fractions were collected and analyzed for purity by SDS-PAGE. The subsequent TNFa pool was about 90% pure based on Coomassie-stained SDS-PAGE and was fully active based on a Bradford protein assay, using lysozyme as a standard, and an ME180 bioassay, using Amgen's TNFa as a standard (Bradford, M. Annal. Biochem. 72, 248–254 (1976)).

TNFa was concentrated in an Amicon Centriprep-10 to about 25 mg/ml, dialyzed against 100 mM NaHCO$_3$, pH 8.5, and coupled to Affigel-15 resin at 25 mg TNF/ml resin. A coupling efficiency of greater than 80% yielded a high capacity resin which was used to further purify the TNF inhibitor.

Figure 7:
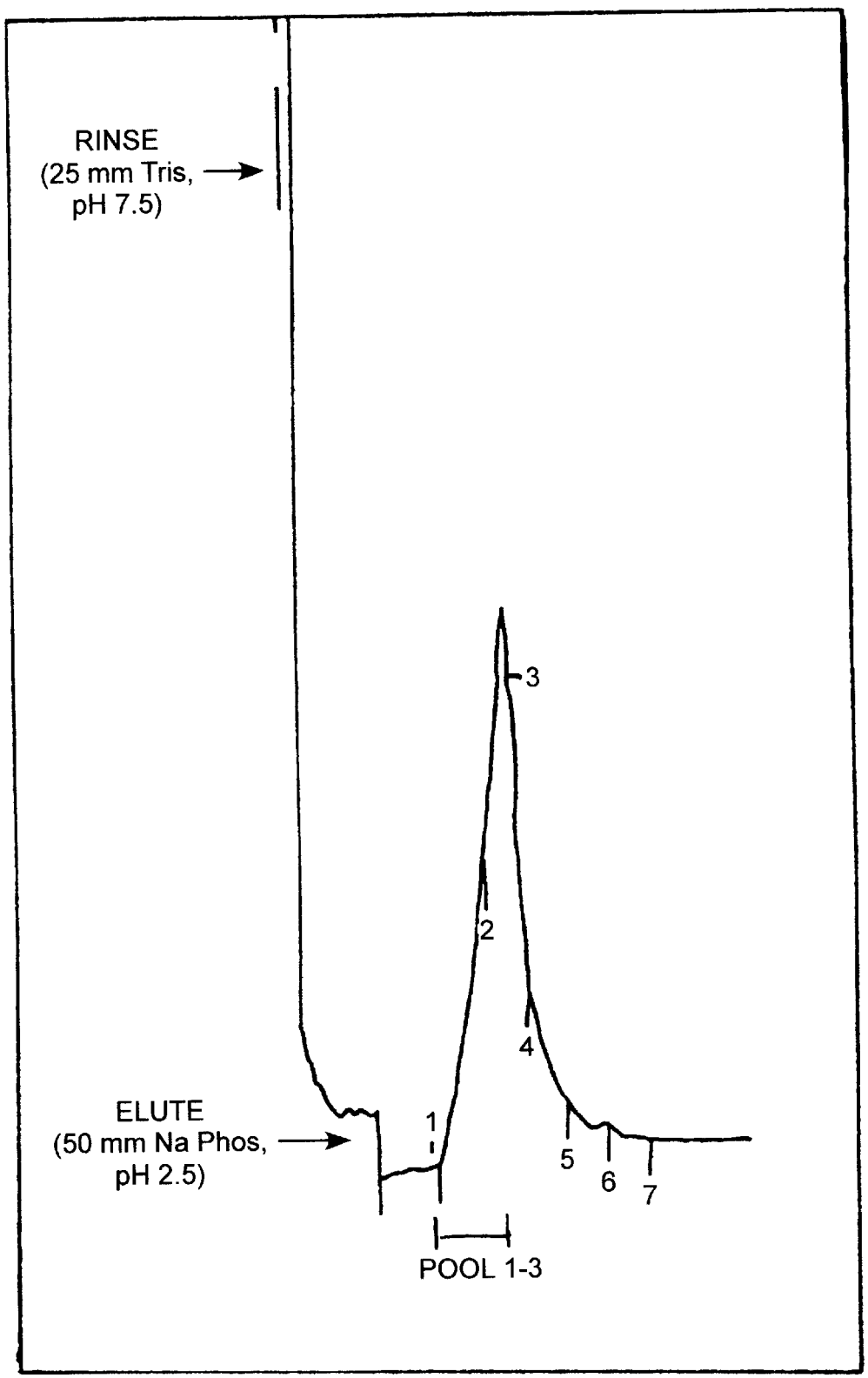

PMSF, at a final concentration of 1–4 mM, was added to the DEAE CL-6B pool and applied to a 4×1 cm TNF affinity column equilibrated at 4° C. with 0.025 M Tris-HCl pH 7.5 at a flow rate of 0.1 ml/min. The column was then rinsed with 0.025 M Tris-HCl pH 7.5 until the OD$_{280}$ of the effluent returned to baseline. The column was subsequently eluted with 0.05 M NaPhos, pH 2.5 and monitored by OD$_{280}$. FIG. 7 shows the OD$_{280}$ profile of the 0.05 M NaPhos pH 2.5 elution from the TNF affinity column.

The TNF inhibitor was purified to homogeneity by reverse phase HPLC on a Syncropak RP-8 (C8) column. The OD$_{280}$ peak from the TNF affinity column was pooled and immediately loaded onto a RP-8 column, equilibrated with 0.1% TFA/$H_2O$, a linear 1%/min gradient of 0.1% TFA/ acetonitrile was run, from 0–50%, and monitored by $OD_{215}$ and $OD_{280}$. Fractions were collected and assayed from bioactivity using L929 cells and the native gel assay described in Example 1.B. Both of these assays indicate bioactivity at fractions 28–32 which corresponds to a peak of $OD_{215}$ and OD280 eluting at 18% acetonitrile.

Figure 8A:
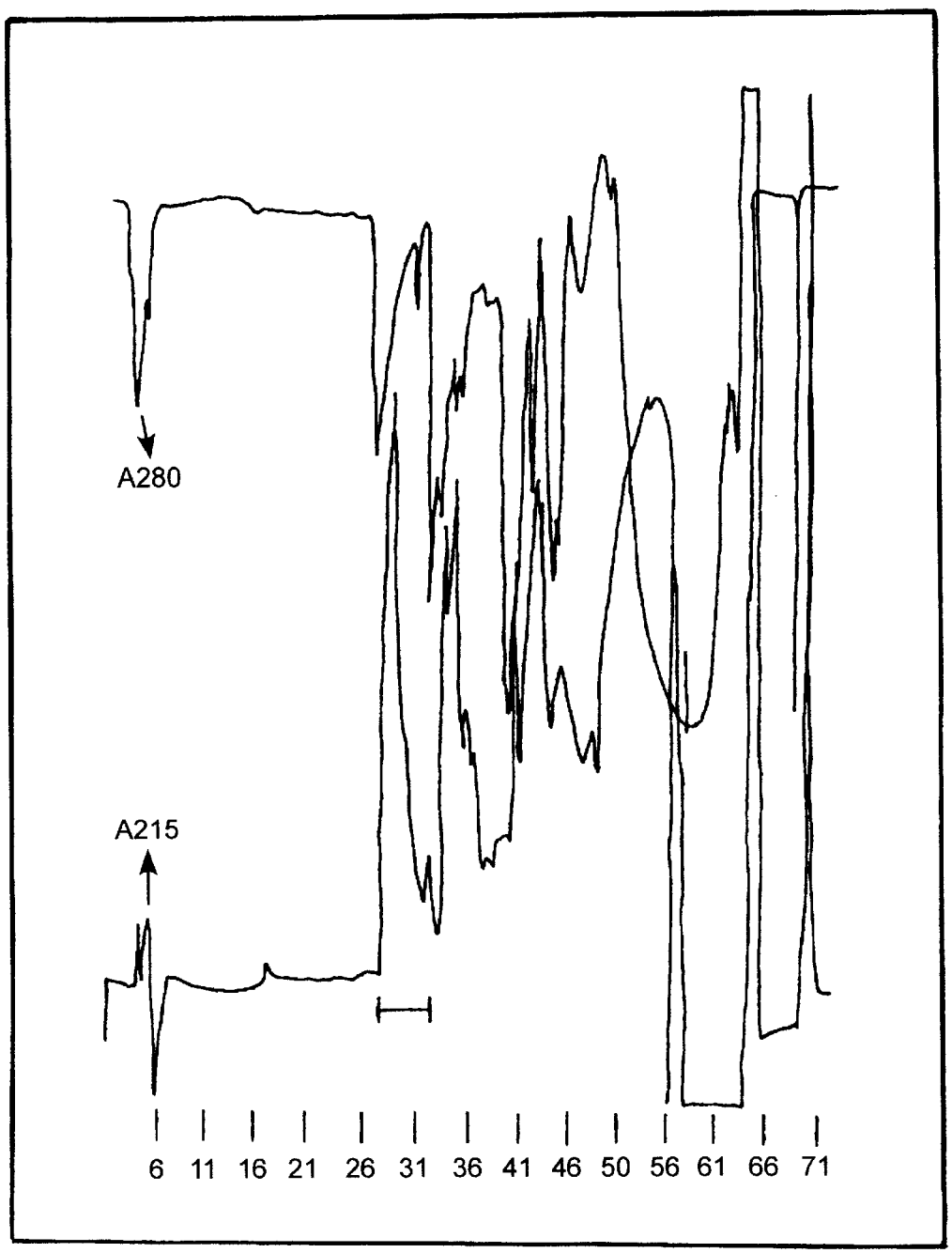
Figure 8B:
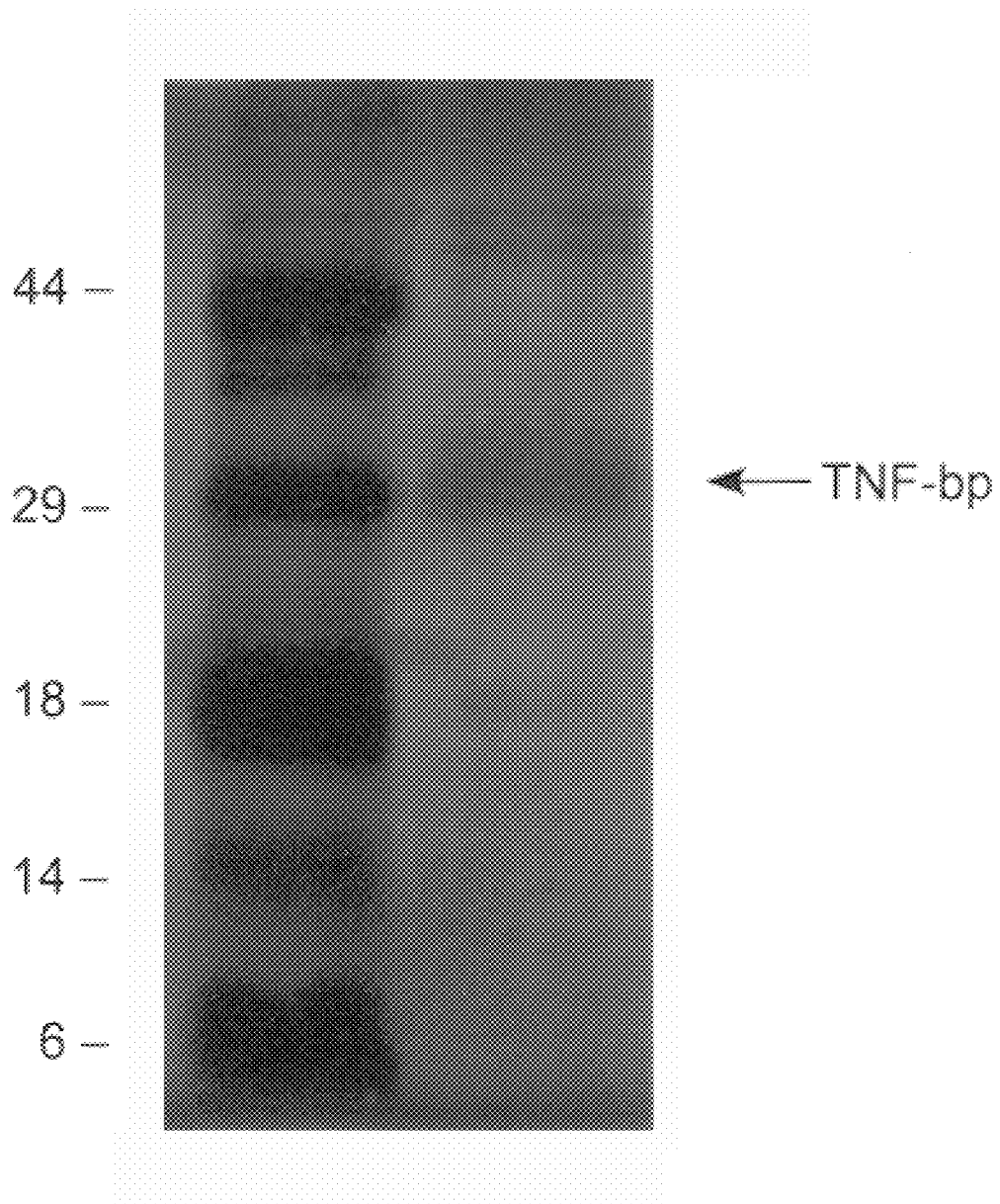

FIG. 8A and 8C show the chromatographic profile of the TNF affinity pool on a Syncropak RP-8 column with the corresponding bioactivity from the L929 cytotoxicity assay. FIG. 8B shows a silver stained 15% reducing SDS-PAGE of the RP-8 pool indicating a single band at 30kDa.

Figure 3:
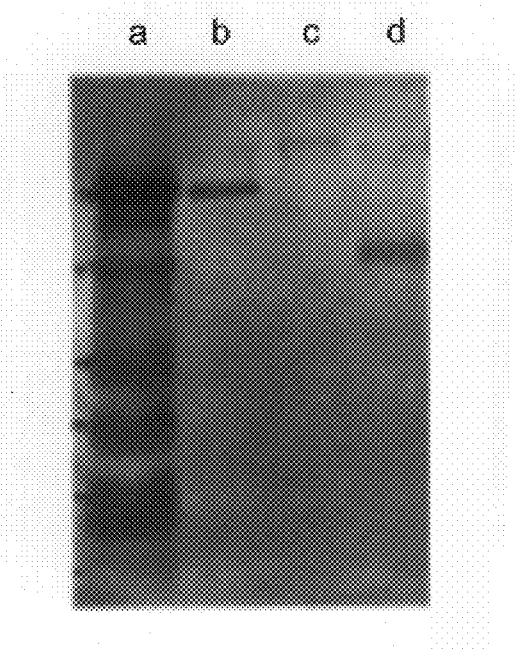

D. Characterization of the Protein Component of 30kDa TNF Inhibitor 30kDa TNF inhibitor is a glycoprotein as was detected using Concanavalin A-Peroxidase after the protein was transferred onto the nitrocellulose filter. This method is a modification of Wood and Sarinana (Analytical Biochem. 69, 320–322 (1975)) who identified glycoproteins on an acrylamide gel directly. The peroxidase staining of glycoprotein was performed by using peroxidase conjugated Con A or non-conjugated Con A. When non-conjugated Con A was used, the nitrocellulose filter was incubated for one hour in a solution containing Con A (0.5 mg/ml, Miles Laboratory) in phosphate buffer, pH 7.2 (PBS); then washed 3×5 min. in PBS. The washed filter was incubated in horseradish peroxidase (0.1 mg/ml, Sigma Chemical) for one hour. After 3×15 min. wash PBS the filter was immersed in a solution containing 3 mg/ml 4-chloro-1-naphthol (Sigma Chemical) and 12.5 ul/ml of hydrogen peroxide until the color was developed. Glycoprotein was seen as a purple color. A photograph was made as soon as the filter was developed as shown in FIG. 3.

Figure 4:
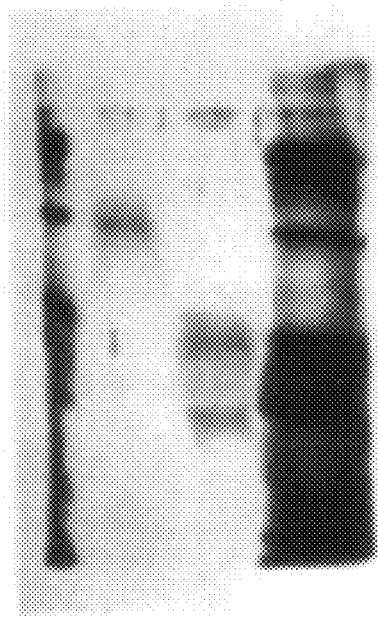

Chemical deglycosylation of TNF inhibitor was carried out by the method of Edge, Faltynek, Hof, Reichert and Weber (Analytical Biochem. 118, 131–137 (1981)). A mixture of 0.25 ml anisole (Eastman Kodak) and 0.5 ml of trifluoromethanesulfonic acid (Eastman Kodak) was cooled to 4° C., then 1–200 ng of dry TNF inhibitor were dissolved in 3 ul of this mixture. The tube was flashed with nitrogen, then incubated for 30 min. at room temperature. This deglycosylated protein was analyzed on SDS-PAGE (FIG. 4). The molecular weight of chemical treated TNF inhibitor is about 18,000 dalton. A band at 14,000 was seen also, but this may be a proteolytic fragment of deglycosylated TNF inhibitor.

Figure 5:
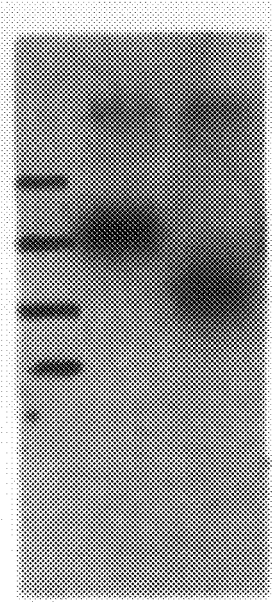

The enzymatic deglycosylation using N-glycanase was performed following the manufacturer's protocol (Genzyme Corp.) except TNF inhibitor was incubated with N-glycanase for 5 to 6 hours instead of overnight. The molecular weight of the deglycosylated form of denatured TNF inhibitor is shown to be about 20,000 dalton (FIG. 5). When the inhibitor is not denatured prior to deglycosylation, the molecular weight of the deglycosylated protein is about 26,000 dalton.

E. Deglycosylated 30kDa TNF-inhibitor binds to TNF.

Radiolabeled TNF inhibitor (30kDa) was treated with TFMSA (trifluoromethanesulfonic acid) in order to remove carbohydrates, and the TFMSA was separated from the protein by HPLC. The protein fraction was mixed with TNF-aff igel for one hour at 4° C., and all unbound material was removed by centrifugation. The TNF-affigel was washed extensively with 50 mM NaPO4, pH 2.5. Radioactivity in each fraction was counted and also analyzed on a SDS-PAGE. Non-specific binding of TNF inhibitor was measured using anhydrochymotrypsin affigel. The results are shown in Table 2. These results indicate that deglycosylated TNF inhibitor (30kDa) binds to TNF.

TABLE 2

| Sample | Type of Affinity | Count (CPM) Flow Through | Eluate |
| --- | --- | --- | --- |
| Native TNF-INH | TNF | 49401 (55.0%) | 40014 (45.0%) |
| Native TNF-INH | Anhy CT | 80000 (98.0%) | 1789 (2.0%) |
| TFMSA-Treated TNF-INH | TNF | 13369 (73.0%) | 4908 (27.0%) |
| TFMSA-Treated TNF-INH | Anhy CT | 15682 (94.0%) | 926 (6.0%) |

In another experiment, radiolabeled TNF inhibitor (30kDa) was reduced, then deglycosylated with N-glycanase. After deglycosylation, the material was incubated with 13 mM oxidized glutathione (GSSG) for 10 minutes at room temperature, and diluted 5 fold with 50 mM Tris. Cysteine was then added to a final concentration of 5 mM. The material was incubated at 40° C. for 16 hours then mixed with a TNF-affigel for one hour at 40° C. Unbound material was removed, and the gel was washed extensively with 50 mM Tris-HCl, pH 7.5. The bound material was eluted with 50 mM $NaPO_4$, pH 2.5. Radioactivity in each fraction was analyzed, and a SDS-PAGE was performed for each fraction. As seen in Table 3 and FIG. 18, the deglycosylated and reoxidized TNF inhibitor also binds to TNF.

TABLE 3

| Sample | Type of Affinity | Count (CPM) Flow Through | Eluate |
| --- | --- | --- | --- |
| Native TNF-INH | TNF | 18281 (60.0%) | 12603 (40.0%) |
| Native TNF-INH (reduced/reoxidized) | TNF | 28589 (94.0%) | 1964 (6.0%) |
| TFMSA-Treated (reduced/reoxidized) | Anhy CT | 31371 (98.70) | 421 (1.3%) |
| Deglycosylated TNF-INH (reduced/reoxidized) | TNF | 25066 (85.0%) | 4305 (15.0%) |
| Deglycosylated TNF-INH (reduced/reoxidized) | Anhy CT | 29619 (98.4%) | 495 (1.6%) |

Example 2

Sequencing of 30kDa TNF Inhibitor

N-terminal sequences were determined using Applied Biosystems Protein Sequencers, models 470 and 477. Prior to sequencing, peptides generated from a variety of proteolytic enzymes were purified on an Applied Biosystems C8-microbore HPLC column (22 cm×2.1 mM).

A. Amino Terminal Sequencing

Approximately 250 pmoles of reverse phase (RP-8) purified TNF inhibitor were applied directly to a polybrene filter and subjected to automated Edman degradation. The resulting sequence information yielded the first 30 amino acids of the molecule.

B. Endoproteinase Lys-C Digestion of Native Protein

Figure 9A:
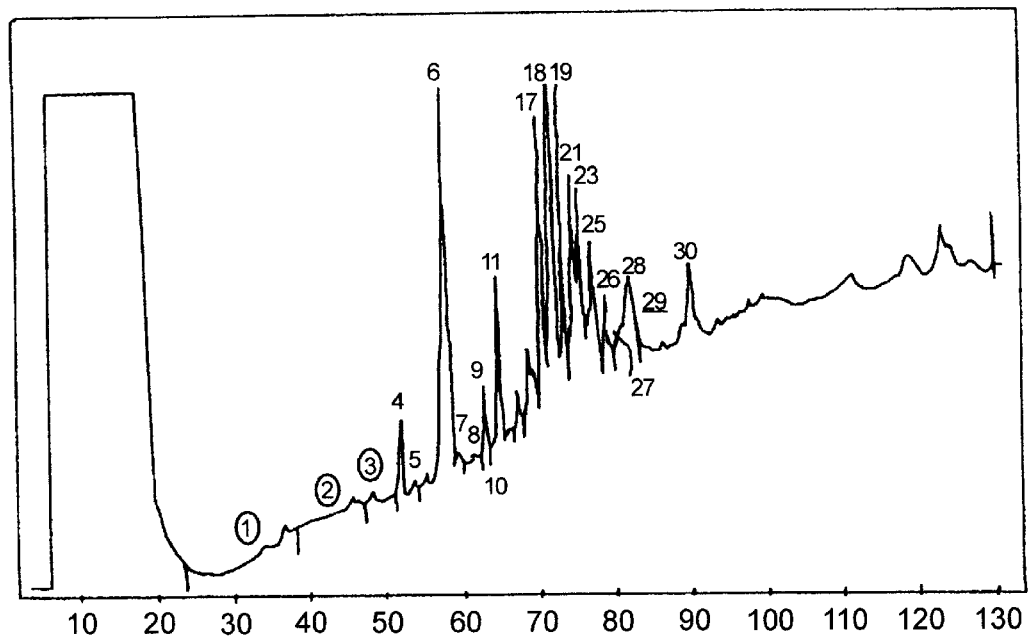
Figures 1, 9B:
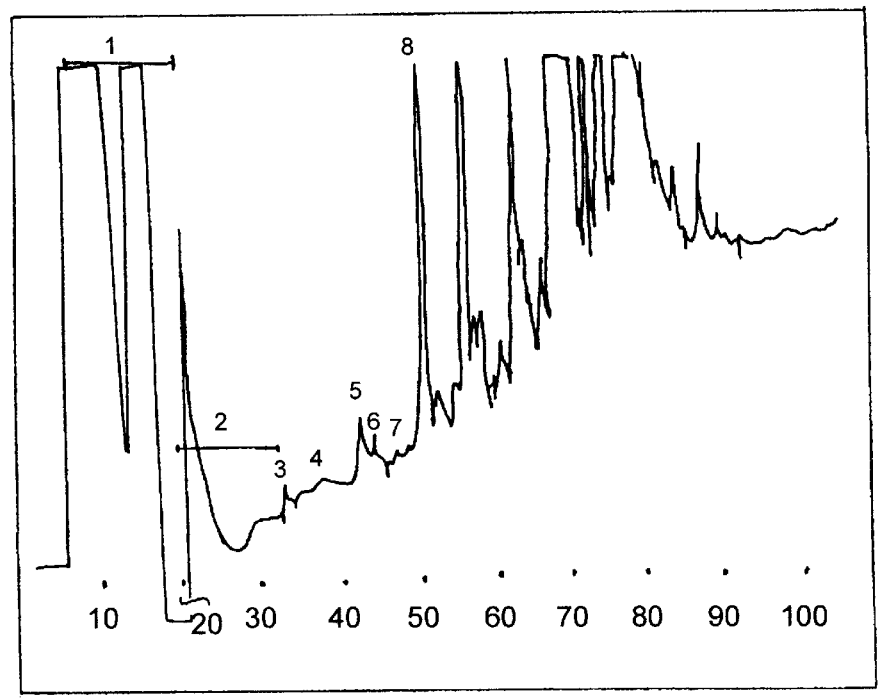
Figures 2, 9B:
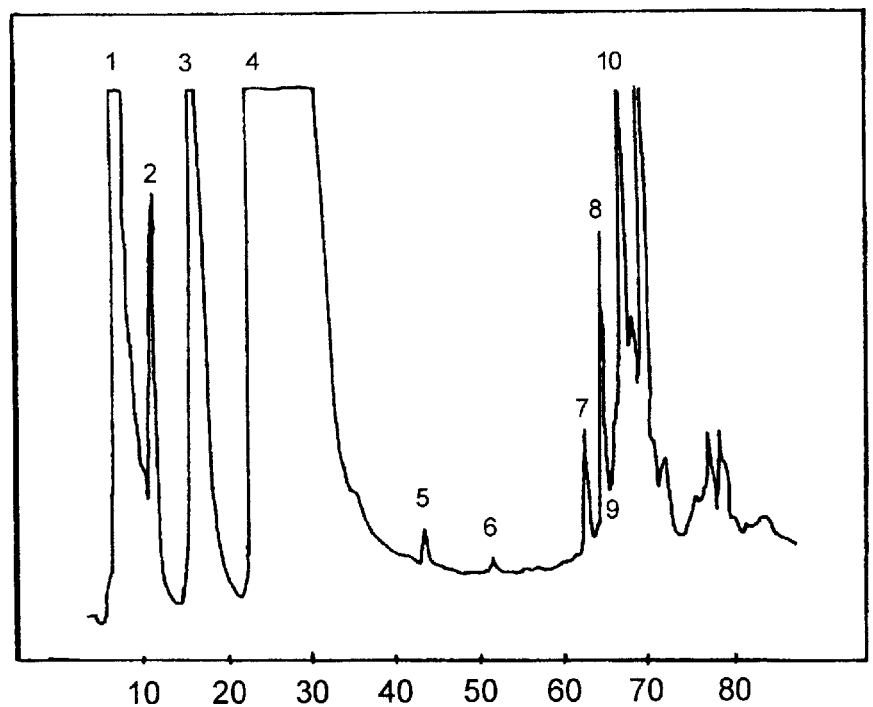
Figures 3, 9B:
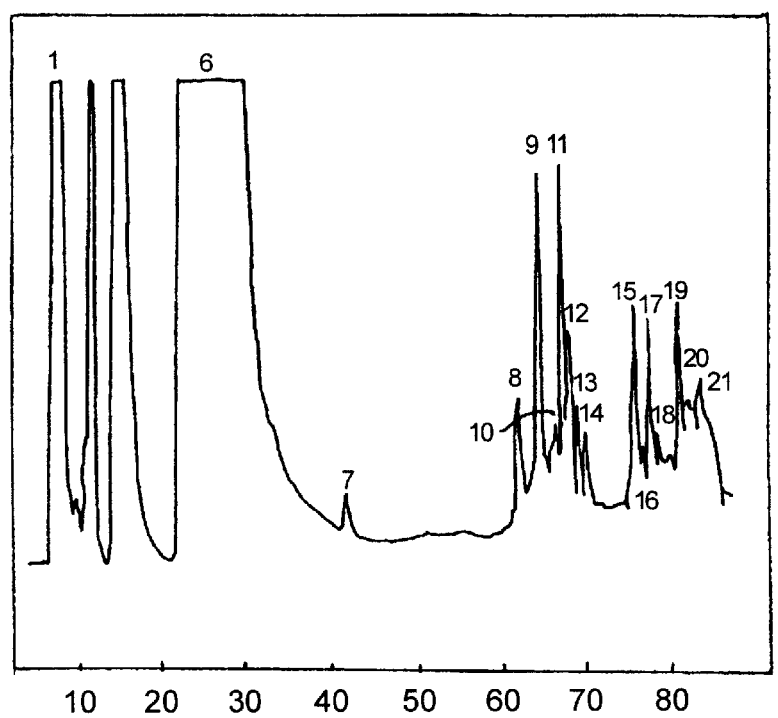

Approximately 250 pmoles (5 ug) of reverse-phase purified TNF inhibitor was digested with 1 ug of endoproteinase Lys-C. The 12 hour digestion at 25° C. was carried out in the presence of 1M urea, 0.01% Tween 20, and 150 mM $NH_2HCO_3$, pH 8.0. Prior to peptide purification the digest was reduced by incubation for 1 hour following addition of 50-fold molar excess of dithiothreitol, or reduced and alkylated by a further one hour incubation at 37° C. using a two-fold molar excess of [$^3$H]-iodoacetic acid over dithiothreitol. FIG. 9A shows the reverse phase HPLC pattern of this digestion. FIG. 9B shows the reverse phase HPLC pattern of this digest followed by alkylation.

C. Endogroteinase Asp-N Digestion of Native Protein

Approximately 250 pmol (5 ug) of reverse phase purified TNF inhibitor was digested with 0.5–2.5 ug endoproteinase Asp-N. The 12–18 hour digest at 37° C. was carried out in the presence of 1M guanidine-HCl, 0.01% Tween 20 and 150 mM NaPhos, pH 8.0.

Figure 10A:
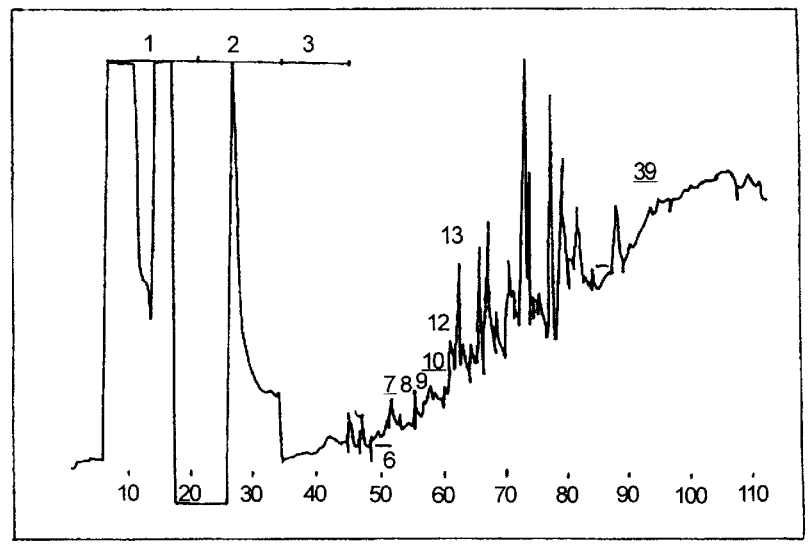
Figure 10B:
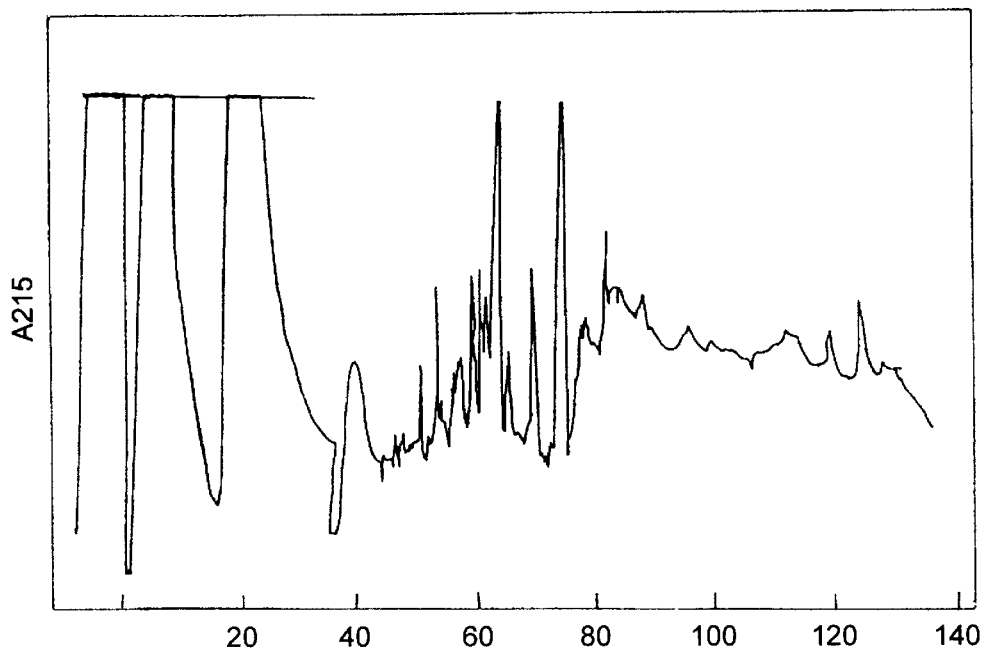

Prior to peptide purification the digest was reduced and alkylated as in Example 2.B. FIG. 10 shows the reverse phase HPLC pattern of two such digests.

D. Reduction Carboxymethylation of Protein

The reverse-phase HPLC purified TNF inhibitor was reduced and carboxymethylated with [$^3$H] Iodoacetic acid as described by Glazer, et al., in Chemical Modifications of Proteins, pp. 103–104 (1975), except two successive rounds of reduction followed by alkylation were used. The protein was re-purified by reverse-phase HPLC prior to proteolytic digestion.

E. Endoproteinase VB Digestion of Reduction Carboxymethylation of Protein

Figure 11A:
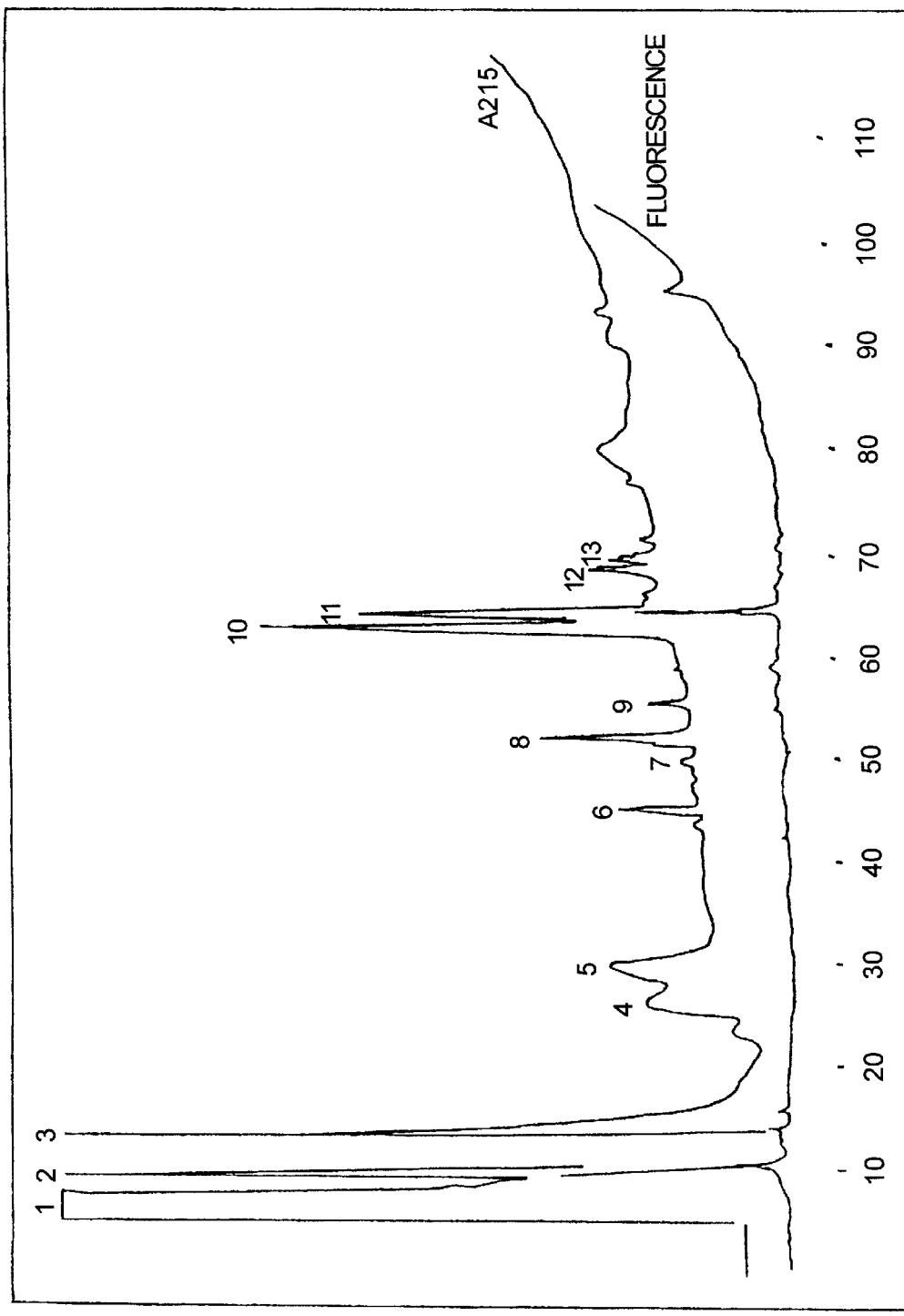
Figure 11B:
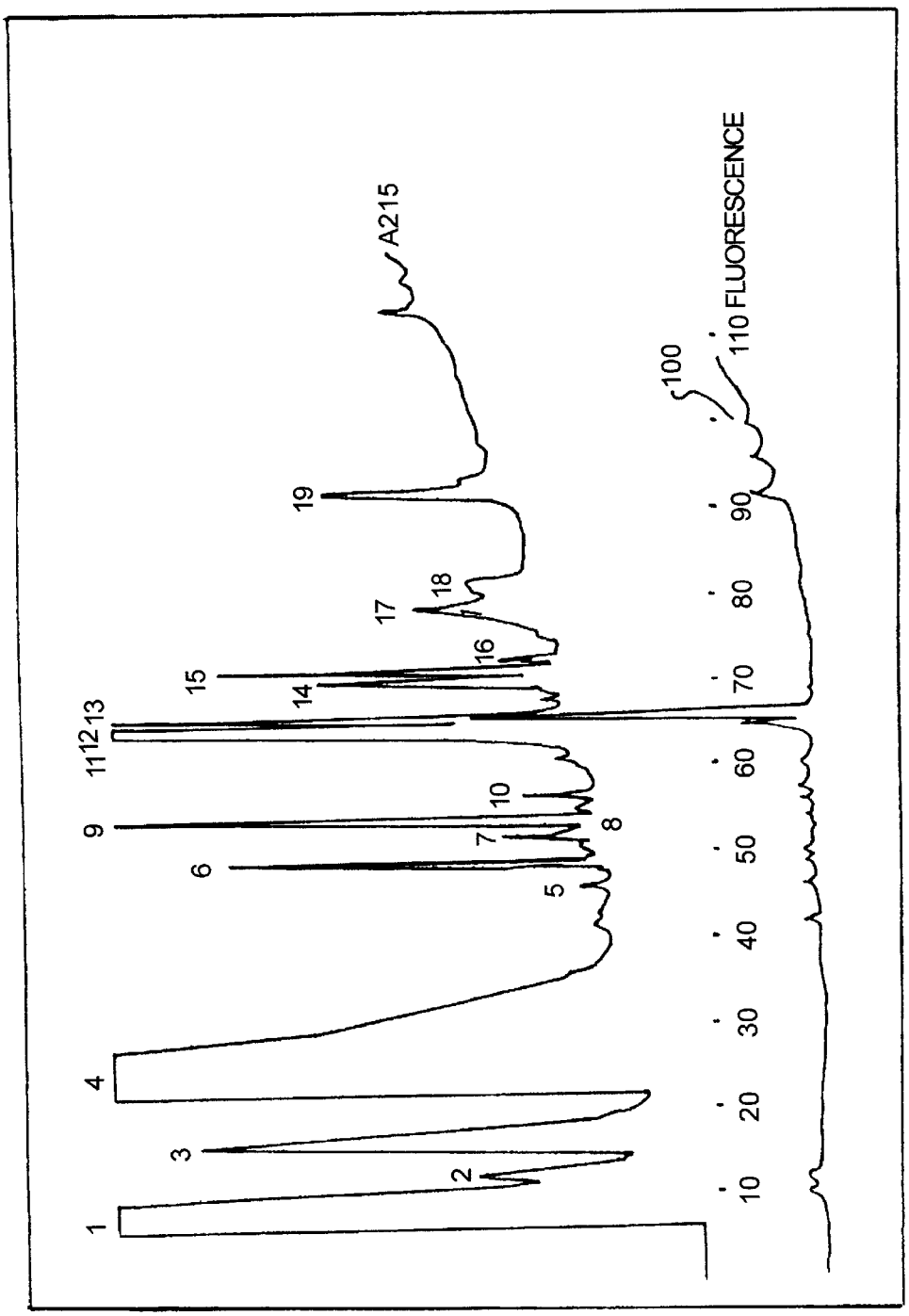

An analytical digest was performed by dissolving 55 pmoles (about 1 ug) of reduced carboxymethylated TNF inhibitor in 150 mM NaHCO$_3$ pH 8.0, and digesting it with 0,2 ug V8 protease for 18 hours at 25° C. Reverse-phase HPLC (FIG. 11A) revealed three sequenceable peptides and indicated a larger scale digest was in order. Approximately 220 pmoles (4.5 ug) of reduced carboxymethylated TNF inhibitor was digested with 1 ug V8 protease for 5 hours at 25° C., when an additional 0.5 ug V8 protease was added and the digestions continued for 16 hours. FIG. 11B shows the reverse-phase HPLC of the large scale V8 digest.

F. Complete Primary Structure of 30kDa TNF Inhibitor Based on Peptides Sequences and cDNA Sequence.

Various peptide fragments were aligned according to the cDNA sequence obtained in Example 4. This is shown in FIG. 19. Residues which are not identified by protein sequencing are residue numbers 14, 42, 43, 44, 96, 97, 105, 107, 108, and 110 through 119. The sequence of Gln-Ile-Glu-Asn is apparently the carboxyl terminus of the 30kDa TNF inhibitor.

Example 3

30kDa TNF Inhibitor is Produced by U937 Cells Stimulated with PMA and PHA

The monocyte-like cell line U937 was grown at 37° C. in RPMI medium containing 10% fetal calf serum to a cell density of 1×10$^6$ cells/ml. The cells were then removed by centrifugation and resuspended on 5 different 100 cm$^2$ petri plates at 2×10$^6$ cells/ml in RPMI without serum containing 10 ng/ml of PMA (phorbol 12-myristate 13-acetate) and 5 ug/ml PHA-P (phytohemagglutinin-P). The conditioned medium from one plate was harvested after only 10 minutes of incubation and used as a zero time control. The medium from the remaining plates was successively removed at 24 hours, 48 hours, 72 hours and 96 hours after plating. The protein contained in these samples was concentrated into approximately 400 ul each by Centriprep-10 (Amicon Corp.) treatment. Each 400 ul sample was then mixed with an equal volume of an Affigel-15 (Biorad Corp.) preparation containing approximately 10 mg/ml of purified human recombinant TNFa that had been prepared in our laboratory. This TNFa, prior to being bound to the Affigel-15 resin, had been shown to be bioactive by its toxicity to murein L929 cells.

Figure 15:
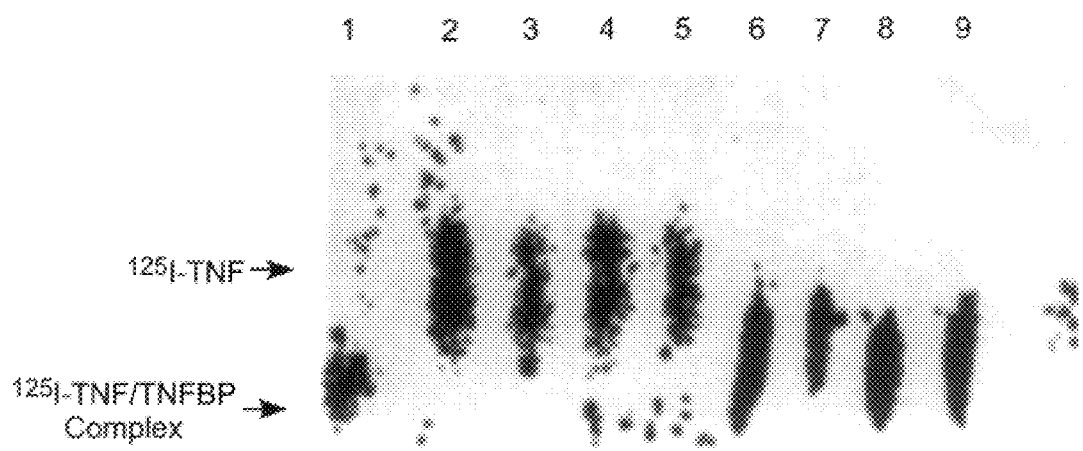

The conditioned medium was incubated at room temperature batchwise with the TNFa affinity resin for 2 hours. The unbound fraction was removed after centrifugation of the resin and the resin was subsequently washed with 1 ml (500ul, 2×) of PBS (phosphate buffered saline, pH 7.5) containing 0.1% gelatin. Bound material was eluted with a 25 mM solution of monobasic sodium phosphate, pH 2.5 (400 ul, 2×). 40 ul of each of the unbound, washed, and eluted fractions were dried, resuspended in 10 ul of 25 mM Tris pH 7.5, mixed with 2 ul (100 pci) of $^{125}$I-TNFa (400–800 ci/mmole, Amersham) and incubated for 30 minutes at room temperature. These mixtures were then mixed with 5 ul of 40% sucrose and 1 ml of 0.1% bromophenol blue and applied to a 4% native acrylamide gel as described in Example 1.B. The conditioned medium from all samples except the zero control contained TNFa binding activity by this assay as shown in FIG. 15.

Figure 16:
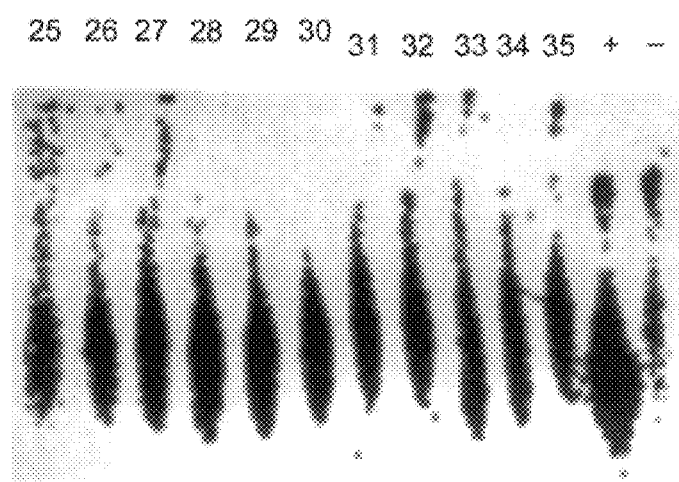

The remaining 300 ul from each sample (1st low pH elution) were applied to a C8 HPLC column and eluted with a linear gradient of acetonitrile over 60 minutes (1%/minute, 1 ml/minute flow rate, 1 ml fractions were collected). Each fraction as dried and resuspended in 50 ul of PBS+0.1% gelatin. 10 ul of each of these samples was mixed with $^{125}$I-TNFa as above and analyzed by native polyacrylamide gel. TNFa binding activities are detected in fractions corresponding to 33% and 36% acetonitrile as shown in FIG. 16.

Example 4

Analysis of Messenger RNA from PMA/PHA Treated U937 Cells

Figures 17, 18:
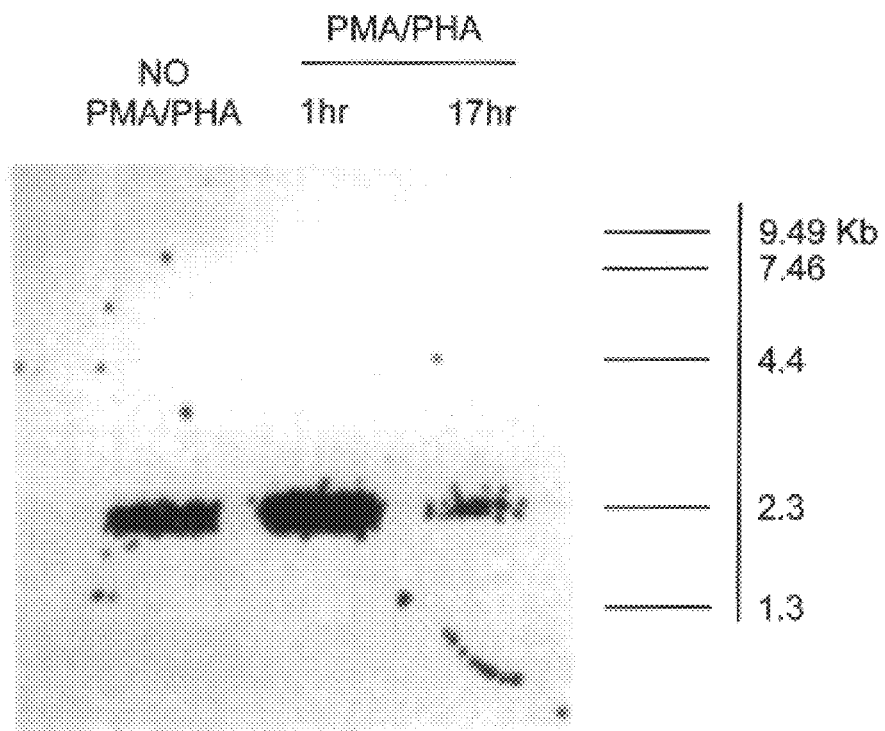

U937 cells were grown as described in Example 3 to a density of 1×10$^6$ cells/ml and then resuspended in serum-free medium at 2×10$^6$ cells/ml without or with PMA (10 ng/ml) and PHA (5 ug/ml). Samples were taken at 1 hour+/− PMA/PHA and 17 hours+PMA/PHA only. Total RNA was prepared from the cells by the guanidinium thiocyanate-phenol-chloroform method of Chomczynski and Sacci (Analytical Biochemistry 162:156–159, (1987)). Poly A$^+$ RNA was prepared from total RNA by annealing to oligo dT cellulose (Bethesda Research Labs). Eight micrograms of each poly A$^+$RNA was then applied to a 6.6 formaldehyde, 1.2% agarose gel. The RNA within the gel was then blotted to a zeta probe membrane (BioRad). The membrane was treated as described in Example 5 for screening of a human genomic DNA library with oligonucleotide probes. 1×10$^6$ cpm/ml of a labelled single stranded DNA probe (polynucleotide kinase) was added. The sequence of this probe is:

5' TTGTGGCACTTGGTACAGCAAAT 3' and it corresponds to bases 410–433 of the sequence set forth in FIG. 13. Following overnight hybridization at 65° C., the membrane was washed once at room temperature in 6×SSC 0.1% SDS and once at 65° C. in the same solution and then exposed to x-ray film for 72 hours. The autoradiogram shown in FIG. 17 shows that PMA/PHA treatment of U937 cells in serum-free medium for 1 hour clearly stimulates the expression of the 30kDa TNFa inhibitor messenger RNA and that by 17 hours of treatment this message is virtually absent from the cells. The molecular size of the 30kDa TNFa inhibitor messenger RNA based on this experiment is approximately 2.4 kilobases.

Example 5

Preparation of a Human Genomic DNA Library for 30kDa TNF Inhibitor

Human genomic DNA was partially digested with Sau3AI and size selected. DNA with an average size of 15 KB was ligated into the BamHI site of bacteriophage lambda Charon 30. (Rimm, D. L., Horness, D., Kucera, J., and Blattner, F. R. Gene 12:301–309 (1980)). Phage were propagated and amplified on E. coli CES 200.

A. Probes

The four degenerate oligonucleotide hybridization probes listed in Table 4, were synthesized on an Applied Biosystems DNA synthesizer. Each probe mixture consisted of all possible DNA sequences coding for the given peptide sequence.

TABLE 4

| Peptide Name | Peptide Sequence | Probe Name | Probe Sequence |
|---|---|---|---|
| LysC 18 | KEMGQVE | TNFBP-P20 | 5'TCNACTCTGNCCCATTCTCTCTT 3' |
| LysC 11 | QGKYIHP | TNFBP-P2' | 5'CAAGGGNAAAGTATCACATCC 3' |
| LysC 11 | YNDCPG | TNFBP-P3' | 5'TATCAATCGATCTGTCCCNGG 3' |
| LysC 11 | YIHPQNN | TNFBP-P4 | 5'TTAGTTTCTGNGGAGTCAGT 3' |
| | | | N = G, A, T, or C. |

Oligonucleotides were labeled with [gamma $_{32}$P]ATP (Amersham Inc., Arlington Heights, Ill.) and T4 polynucleotide kinase (Boehringer Mannheim, Indianapolis, Ind.) to a specific activity of 6–9×10$^6$ c.p.m./picomole according to manufacturer's. instructions.

B. Methodoloay:

8.4×10$^5$ lambda phage containing human genomic DNA were plated and transferred to duplicate nitrocellulose filters. These filters were hybridized with 1 pMol/ml of probe TNFBP-P2' for 16 hours in a solution containing 1.0 M NaCl, 0.1 M sodium citrate, 2× Denhardts solution (Denhardt, D. T. Biochem. Biophys. Res. Commun. 23:641–646 (1966)), 0.1% SDS, 0.05% sodium pyrophosphate and 150 ug/ml yeast tRNA at a temperature of 52° C. This temperature is 2° C. below the calculated Tm for the most AT-rich member of the oligonucleotide pool. (Suggs, S. V. in Developmental Biology Using Purified Genes, (Brown, D. D., and Fox, C. F., eds.) Academic Press, New York, pp. 683–693 (1981)). After hybridization, the filters were washed for 45 minutes at ambient temperature with three changes of 1 M NaCl, 0.1 M sodium citrate and 0.5% SDS. A stringent wash of eight minutes was done at the calculated Tm (i.e., 2° C. above hybridization temp) for the most AT-rich member to the pool. Filters were then dried and autoradiographed for 40 hours with one intensifying screen at −70° C.

Eleven positive hybridizing plaques were detected and these were isolated and amplified. The ability of these clones to hybridize to TNFBP-P20, TNFBP-P3' and TNFBP-P4 was tested using similar methodology. One clone (TNFBP-8) hybridized to all four oligonucleotides. This clone was plaque purified and amplified. DNA was prepared from this clone using Lambda-Sorb (Promega Corporation, Madison, Wis.) and a method described by the manufacturer.

One microgram of this DNA was then digested with Sau3AI and the fragments subcloned into BamHI digested M13 sequencing vector mp 18 (Yanish-Perron, C., Viera, J., and Messing, J. Gene 33:103–119 (1985)). M13 clones were then transferred to duplicate nitrocellulose filters and hybridized to the oligonucleotide probes in Table 4 using conditions previously described. Positive subclones were purified and sequenced (Sanger, F., and Coulson, A. R. J. Mol. Biol. 94:441–448 (1975)) using a modified T4 DNA polymerase (Sequenase, US Biochemical Corp., Cleveland, Ohio) as described by the manufacturer, and using as primers either the degenerate probes used to identify the clone or sequence obtained using those probes. Among the sequences obtained are those of Subclones TNFBP-M13-Sau3A-P2'-2 and TNFBP-M13-Sau3A-P4 Primers P3, P3', P2', P2 and P4. The sequence data is set forth in FIG. 13. The sequence contains DNA coding for at least 48 amino acids of 30kDa TNF inhibitor peptides other than those specified by the probes and therefore confirms that the clone TNFBP8 codes for TNF inhibitor. The sequence also shows that the gene for TNF inhibitor includes at least one intron (GTAGGGGCAA . . . CCCCATTCACAG). Finally, this sequence shows that 30kDa TNF inhibitor is synthesized as a precursor protein and that a proteolytic cleavage at the Arg-Asp sequence is required to generate the mature, active protein.

Example 6

Preparation and Screening of a cDNA Library of mRNA from U937 Cells Stimulated with PMA/PHA.

The experiment described in Example 4 shows that U937 cells treated with PMA/PHA for 1 hour should contain a pool of messenger RNA enriched for the TNF inhibitor (30kDa). Accordingly, a cDNA library was prepared from polyA$^+$ RNA obtained from U937 cells treated with PMA/PHA as described in Example 4. Double stranded, blunt ended cDNA was obtained from approximately 5 ug of poly A$^+$ RNA essentially as described by Gubler, U., and Hoffman, B. J., (1983 Gene, 25:263) using lot tested reagents (Amhersham, Arlington Heights, Ill.) according to procedures recommended by the manufacturer. Approximately 1 ug of double stranded cDNA obtained was treated with the enzyme EcoRI methylase and EcoRI linkers having the sequence: d(pCCGGAATTCGG) (New England Biolabs, Beverly, Mass.), were attached via T4 DNA ligase followed by digestion with endonuclease EcoRI. This DNA was then ligated into a lambda-bacteriophage cloning vector gt10 (Young, R. A., and Davis, R. W. (1983) Proc Natl Acad Sci USA, 80:1194–1198) that had been digested with EcoRI and the product packaged into infective lambda-bacteriophage particles using lambda-DNA packaging extracts (Gigapack II Gold) obtained from Stratagene (La Jolla, Calif.) according to their protocol. This lambda-lysate (cDNA library) was then used to infect E. coli strain C600 hflA and it was shown that the library contained approximately 2.5×10$^6$ recombinant members.

Approximately 4×10$^5$ members of this library were plated on E. coli strain C600 hflA (5×10$^4$ p.f.u./plate). Duplicate lifts to nitrocellulose were made and the filters were treated as described in Example 5 for screening of the human genomic library. The DNA on the filters was then hybridized to the same $^{32}$P labelled probe as described in Example 4 except that the temperature of incubation was 42° C. From 4×10$^5$ recombinant phage plated, 3 duplicate plaques hybridized to this probe. These were further reisolated and probed as above and with an additional synthetic probe having the sequence:

5' CCCCGGGCCTGGACAGTCATTGTA 3'

This probe corresponds to bases 671–694 of the human genomic TNF inhibitor clone shown in FIG. 13. Both probes hybridized to all three plaques identified with the first.

After plaque purification DNA was prepared from these three clones and subcloned into the EcoRI site of M13 vectors MP18 and MP19 as described in Example 5. Each of these cDNAs consists of two EcoRI fragments one of approximately 800 bp common to all three clones and another 1300 bp, 1100 bp or 1000 bp depending on the clone. The likely origin of the unique EcoRI fragments in each clone is incomplete elongation by the enzyme reverse transcriptase during 1st strand synthesis of the cDNA. Therefore, those EcoRI fragments likely represent the 5' end of the TNF inhibitor mRNA and the 800 bp fragment the 3' end. This is confirmed by the DNA sequence obtained for these fragments as described below.

From the EcoRI subclones of the cDNA described above the entire sequence of the 2100 bp cDNA was obtained. The dideoxy nucleotide chain termination method of sequencing was used (Sanger, F. and Coulson, A. R. (1975) *J. Mol. Biol.* 94:441–448). The modified T7 DNA polymerase, Sequenase (U.S. Biochemical, Cleveland, Ohio.) was used as the elongation enzyme as described by the supplier. Sequencing primers were synthetic oligonucleotides prepared from the human genomic sequence of the TNF inhibitor as shown in FIG. 13 or sequences obtained using those primers. FIG. 20 shows the translated sequence derived from one of the cDNA clones. This sequence corresponds to that obtained by protein sequence data as described in FIG. 19. The entire sequence of the human 30kDa TNF inhibitor cDNA from clone lambda-gt10-7ctnfbp is shown in FIG. 21.

Example 7

Expression of the 30kDa TNF Inhibitor cDNA in *Escherichia coli*

The portion of the TNF inhibitor (30kDa) cDNA gene coding for the soluble TNFa binding activity has been prepared for expression in *E. coli* as described below.

Because the protein coding sequence defining the C-terminal portion of the urine derived TNF inhibitor (sequence QIEN, base 771 FIG. 20) is not followed by a termination codon in the cDNA sequence, one was added by oligonucleotide directed in vitro mutagenesis (Biorad, Richmond, Calif.). An M13MP19 clone of the 1300 bp EcoRI fragment from the clone lambda-gt107ctnfbp, was hybridized with the synthetic oligonucleotide:

5'    CTACCCCAGATTGAGAATTAAGCT-
TAAGGGCACTGAGGAC 3'

After 2nd strand synthesis and transfection into an appropriate host, mutant clones were identified by hybridization to the above described mutagenic oligonucleotide. The molecular identity of the clones so identified was confirmed by DNA sequencing as described (Example 5). Next, a 468 bp fragment defined by StyI (position 303) and HindIII defining the C-terminus of the protein was removed from the Rf form as a mutagenized clone and inserted into *E. coli* expression plasmid containing the tacd promoter (DeBoer, H. A., et al., (1983) Proc. Natl. Acad. Sci. USA 80:21–25). This construction was accomplished by use of the synthetic, double strand adapter sequence:

5'  GATCCGATCTTGGAGGATGATTAAATG-
GACAGCGTTTGCCCC 3' GCTAGAACCTCCTAC-
TAATTTACCTGTCGCAAACGGGGGTTC

This adapter translationally couples the TNF inhibitor gene (truncated form as described above) to the first 12 codons of the bacteriophage T7 gene 10. The DNA sequence of this construct from the point of translation initiation at gene 10 through the adapter sequence is shown in FIG. 22. A methionine codon (ATG) is necessarily added to the TNF inhibitor gene sequence for expression in *E. coli*. This plasmid is called pTNFiX-1.

The predicted molecular weight of this protein is approximately 17,600kDa a molecular weight that is very close to the deglycosylated native TNF inhibitor (30kDa).

Example 8

Purification of Active TNF Inhibitor (30kDa) from *Escherichia coli*

Figure 25:
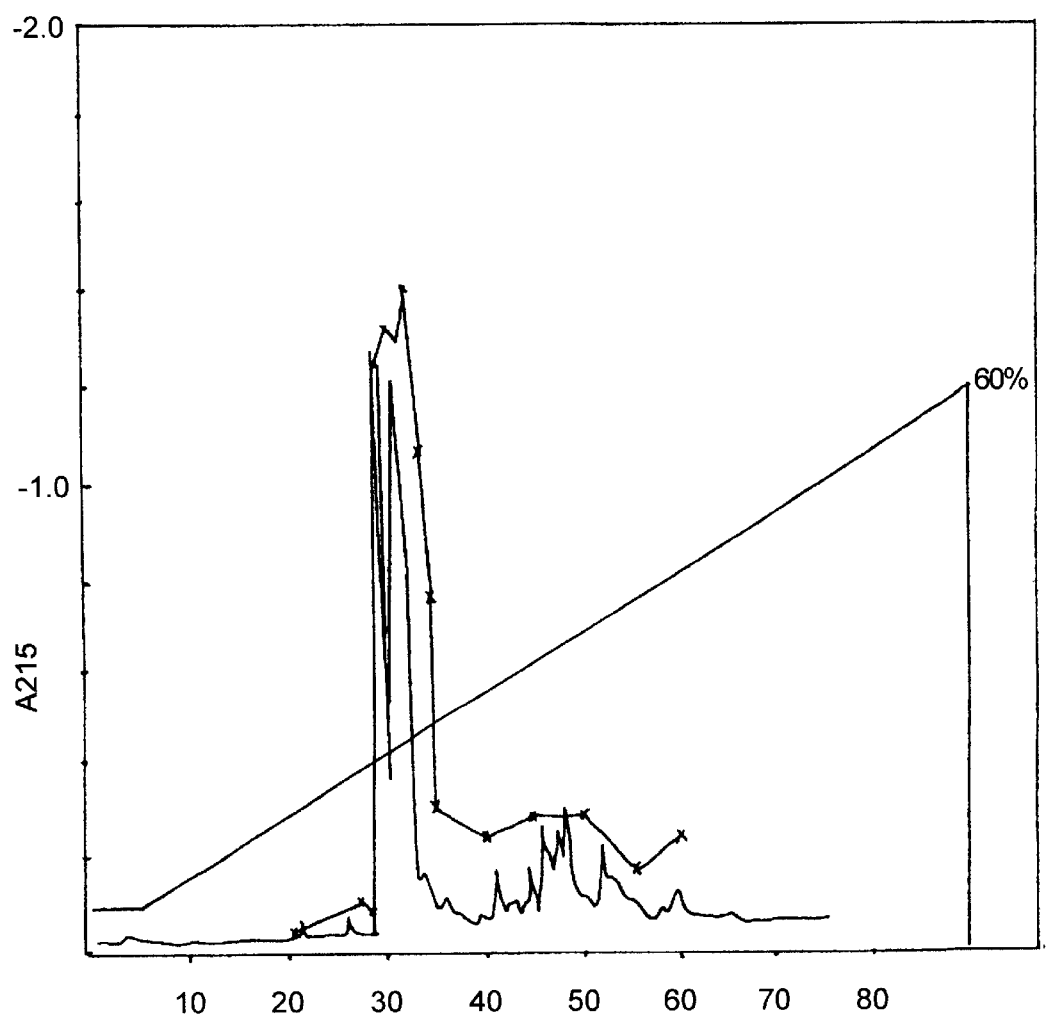
Figure 26:
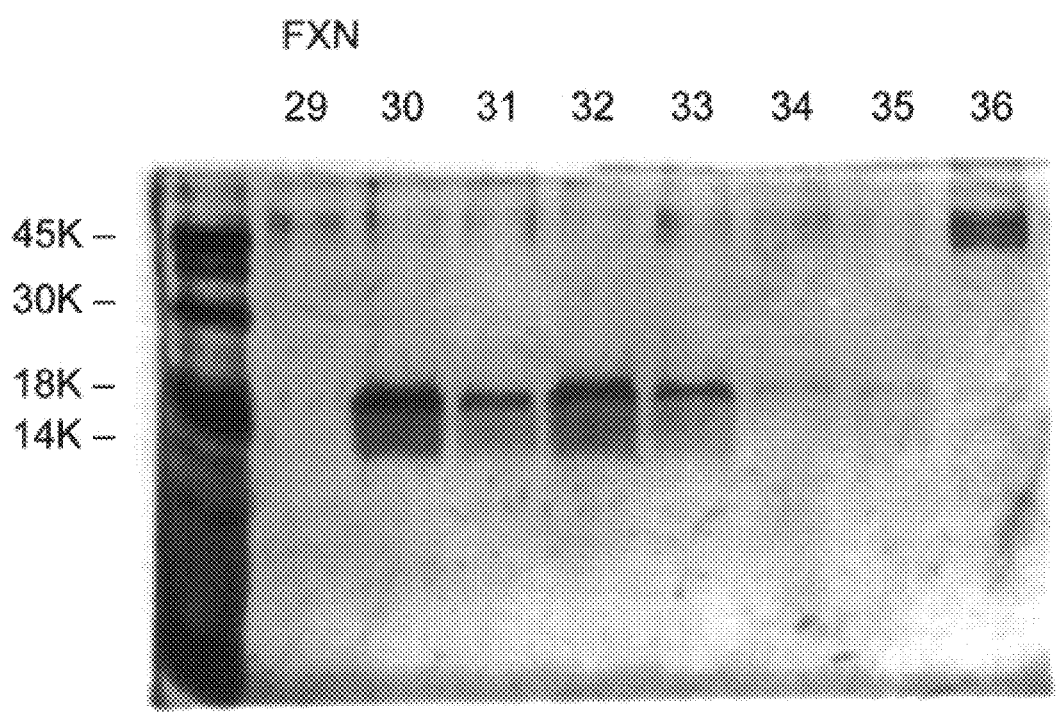

Cells from one liter of *E. coli* culture (PTNFIX-1JM1071on-) grown under induced condition for 2 hours were resuspended in 10 ml of 50 mM Tris-HCl, pH 7.5 containing 2mM EDTA (TE buffer) and French pressed at 20,000 psi. at 4° C. The material was centrifuged at 20,000 g for 10 min. The resulting pellet was washed once with TE-buffer. The washed pellet was resuspended in 2 ml of 6M Guanidine-HCl and incubated at room temperature for 10 min. After the incubation, 80 ul of 500 mM DTT was added and the mixture was incubated at room temperature for another 30 min. The material which remained insoluble after this treatment was removed by centrifugation at 20,000 g for 15 min. 120 ul of 500 mM oxidized glutathione was added to the supernatant, and the mixture was incubated at room temperature for 10 min. This material was then diluted in 20 ml of 0.6% Tris base solution, and 220 ul of 500 mM cysteine was added. The incubation was continued for another 16 hours at 4° C. After 16 hours of incubation, some insoluble residue was observed. This insoluble material was removed by centrifugation at 20,000 g for 20 min. The resulting supernatant was dialyzed against 50 mM Tris-HCl pH 7.5 for 16 hours at 4° C., then centrifuged at 20,000 g for 10 min. PMSF at a final concentration of 4 mM was added to this supernatant and this material was loaded onto a TNF-affinity column (0.7×2 cm) at a flow rate of 0.1 ml per min. This column was extensively washed with 50 mM Tris-HCl pH 7.5, and bound proteins were eluted with 50mM NaPO$_4$-HCl pH 2.5. The pH 2.5 eluate was loaded onto an RP8 column which was previously equilibrated with 0.1% TFA/H20. TNF inhibitor was eluted with a linear gradient of 0.1% TFA/acetonitrile at 1%/min. (FIG. 25). Fractions were analyzed on SDS-PAGE (FIG. 26), and cytotoxicity assay was performed (FIG. 25) to localize the TNF inhibitor. The *E. coli*-produced TNF inhibitor (30kDa) migrates to about 20kDa, since it is not glycosylated. Fractions number 30 through 35 contain TNF inhibitor. The amino terminal sequence of this material shows that the *E. coli* produced TNF inhibitor has the following sequence:

Met-Asp-Ser-Val-()-Pro-Gln-Gly-Lys-Tyr-Ile-His-Pro-Gln-Asn-Asn-Ser-

By using this procedure, about 40 ug of TNF inhibitor (30kDa) was obtained from one liter of the culture. The yield was about 2 to 3%. The yield can be increased to over 50% by purifying the TNF inhibitor before refolding.

Example 9

Expression of Genes Encoding 30kDa TNF Inhibitor in Animal Cells

Animal-cell expression of TNF inhibitor requires the following steps:

a. Construction of an expression vector.

b. Choice of host cell lines.

c. Introduction of the expression vector in host cells.

d. Manipulation of recombinant host cells to increase expression levels of TNF-BP.

1. TNF inhibitor expression vectors designed for use in animal cells can be of several types including strong constitutive expression constructs, inducible gene constructs, as well as those designed for expression in particular cell types. In all cases, promoters and other gene regulatory regions such as enhancers (inducible or not) and polyadenylation signals are placed in the appropriate location in relation to the cDNA sequences in plasmid-based-vectors. Two examples of such constructs follow.

A construct using a strong constitutive promoter region can be made using the cytomegalovirus (CMV) immediate early gene control signals. This plasmid can be constructed using standard molecular biological techniques (Maniatis, et al., *Molecular Cloning, a Laboratory Manual*. Cold Spring Harbor Laboratory, 1982) and resulting in the plasmid shown in FIG. 23.(pCMVXV beta TNFBPstopA) The SV40 origin of replication is included in this plasmid to facilitate its use in COS cells for transient expression assays. This particular construct contains the CMV immediate early promoter and enhancer as described by Boshart, et al., (Cell 41:521–530, 1985) followed by the rabbit B-globin second intron (see van Ooyen et al., *Science* 206:337–344, 1979) which is flanked by BamHI and EcoRI restriction sites. This intron is included because expression levels have been shown to be increased when introns are included in the transcribed regions of some expression vectors (Buckman and Berg, *Mol. Cell. Biol.* 8:4395–4405, 1988). The polyadenylation signal is provided by simian virus 40 (SV40) sequences (map coordinates 2589–2452; see Reddy, et al., *Science* 200:494–502, 1978). The 30kDa TNF inhibitor cDNA sequences have been modified as follows: the extensive region located 3' of the C-terminus of the purified TNF inhibitor from human urine has been deleted and a stop codon has been engineered into the position just following the C-terminal asparagine. The unmodified 30kDa TNF inhibitor cDNA sequences in an analogous vector have been inserted into COS cells and been shown to increase the TNF binding activity of such cells.

Figure 24:
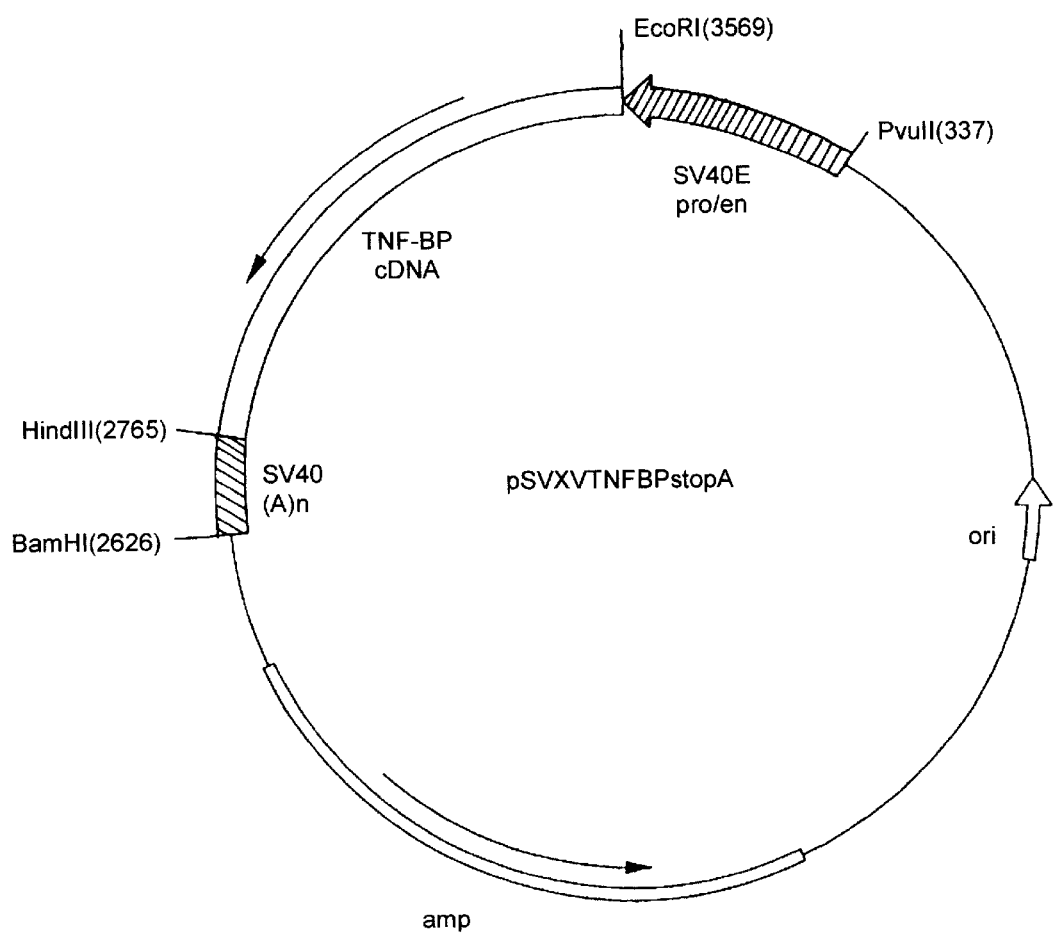

The second construct (see FIG. 24) (pSVXVTNFBP stop A) uses the strong constitutive promoter region from the SV40 early gene in an arrangement such as that found in the plasmid pSV2CAT (Gorman, et al., *Mol. Cell. Biol.* 2:1044–1051, 1982). This plasmid should be manipulated in such a way as to substitute the TNF inhibitor cDNA for the chloramphenicol acetyltransferase coding sequences using standard molecular biological techniques. Once again, the TNF inhibitor cDNA has been modified as described above for the CMV promoter construct. The SV40 early promoter region includes sequences from the HindIII site to the BamHI site (map coordinates 5090–188; see Reddy et al., *Science* 200:494–502, 1978) and the SV40 polyadenylation signal is as described above for the CMV construct.

2. Two animal cell lines have been used to express TNF inhibitor using the vectors described above to produce active protein. Cell lines that have been characterized for their ability to promote expression of this foreign gene include the monkey kidney cell, COS-7, and Chinese hamster ovary (CHO) dihydrofolate reductase deficient (dhrf-) cells.

3. To establish a continuous CHO-derived cell line that secretes 30kDa TNF inhibitor into cell culture medium, a TNF inhibitor expression plasmid has been introduced into these dhfr- cells along with a plasmid that directs the synthesis of dihydrofolate reductase using the calcium phosphate-DNA precipitation technique described by Graham and van der Eb (*Virology* 52:456–467, 1973). The cells that have taken up DNA and express DHFR were selected as described by Ringold, et al., (*J. Mol. Appl. Genet.* 1:165–175, 1981).

4. Cells that express the TNF inhibitor gene constructs can be manipulated to increase the levels of production of TNF inhibitor. Cells containing TNF inhibitor expression vectors along with a dhfr expression vector should be taken through the gene amplification protocol described by Ringold, et al., (*J. Mol. Appl. Genet.* 1:165–175, 1981) using methotrexate, a competitive antagonist of dhfr. Gene amplification leads to more copies of the dhfr and TNF inhibitor genes present in the cells and, concomitantly, increased levels of TNF inhibitor mRNA which, in turn, leads to more TNF inhibitor protein being produced by the cells.

Example 10

Isolation of Two Types of TNF-Inhibitors from U937 Condition Medium and the Existence of the Second TNF Inhibitor in Human Urine The human U937 cells were grown at a density of $1\times10^5$ cells per ml in 150 cm$^2$ flasks using RPMI1640 medium containing 200 units/ml penicillin, 200 units/ml of streptomycin, 10% fetal calf serum. After 3 days of incubation at 37° C., the cells were harvested by centrifugation at 1500 G for 7 minutes. The cells were resuspended at a density of $2\times10^6$/ml in RMPI1640 medium without serum. The cells were grown in the presence of 5 ug/ml PHA-P (Phytohemagglutinin) and 10 ng/ml PMA (Phobol is 12-myristate 13-acetate) for 24 hours.

Figure 27:
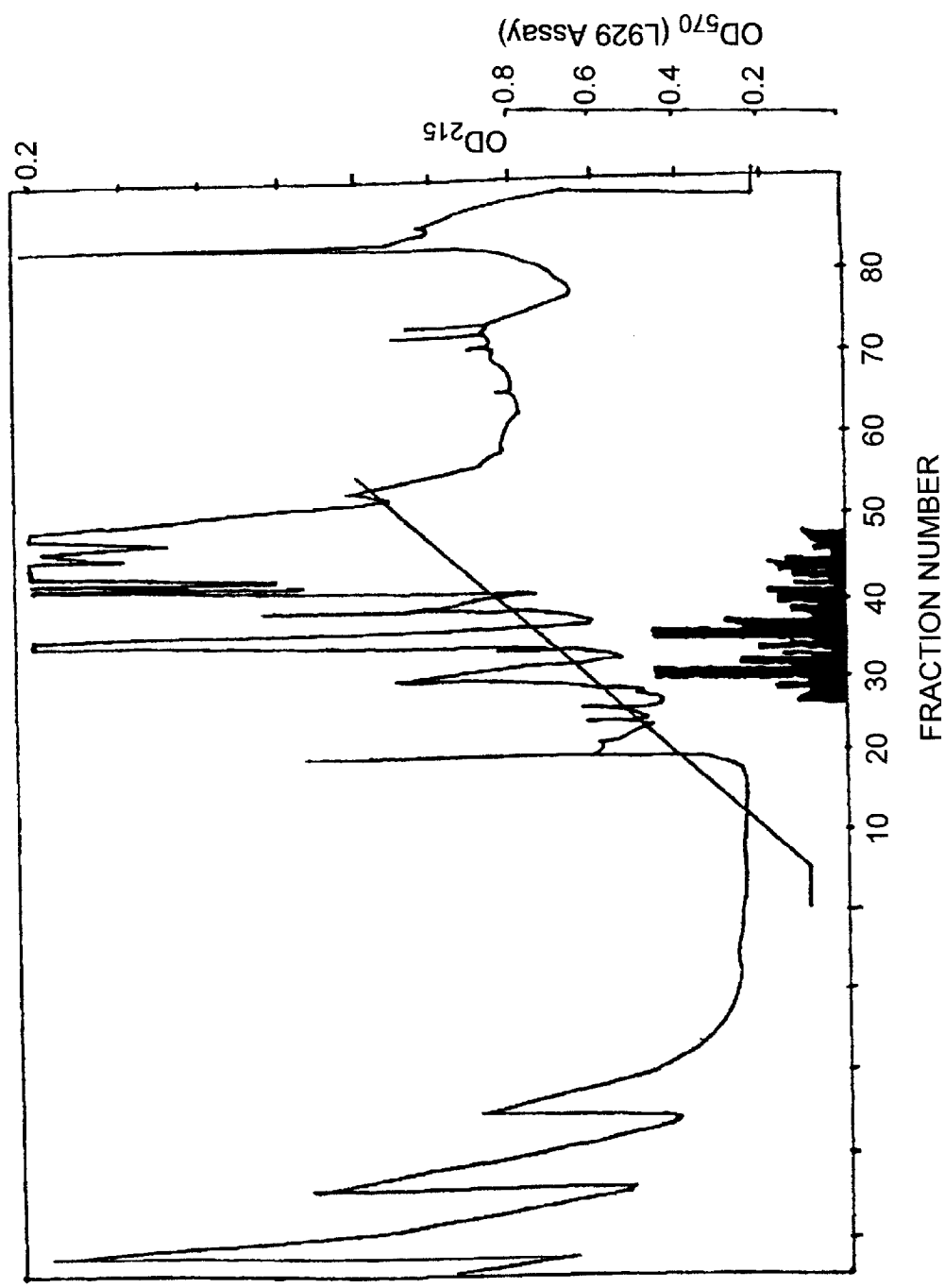
Figure 28:
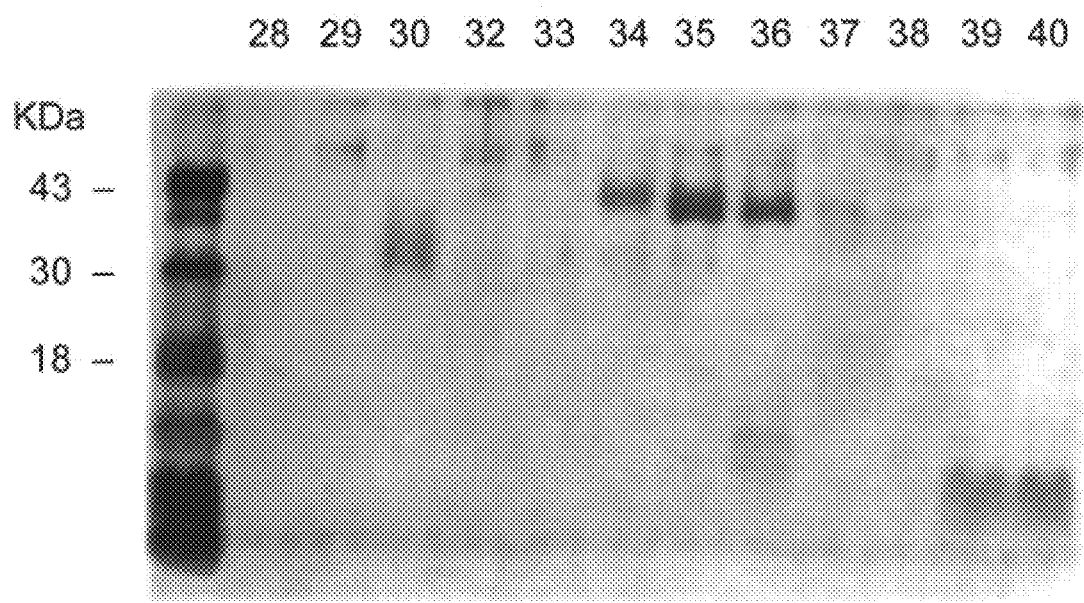
Figure 29:
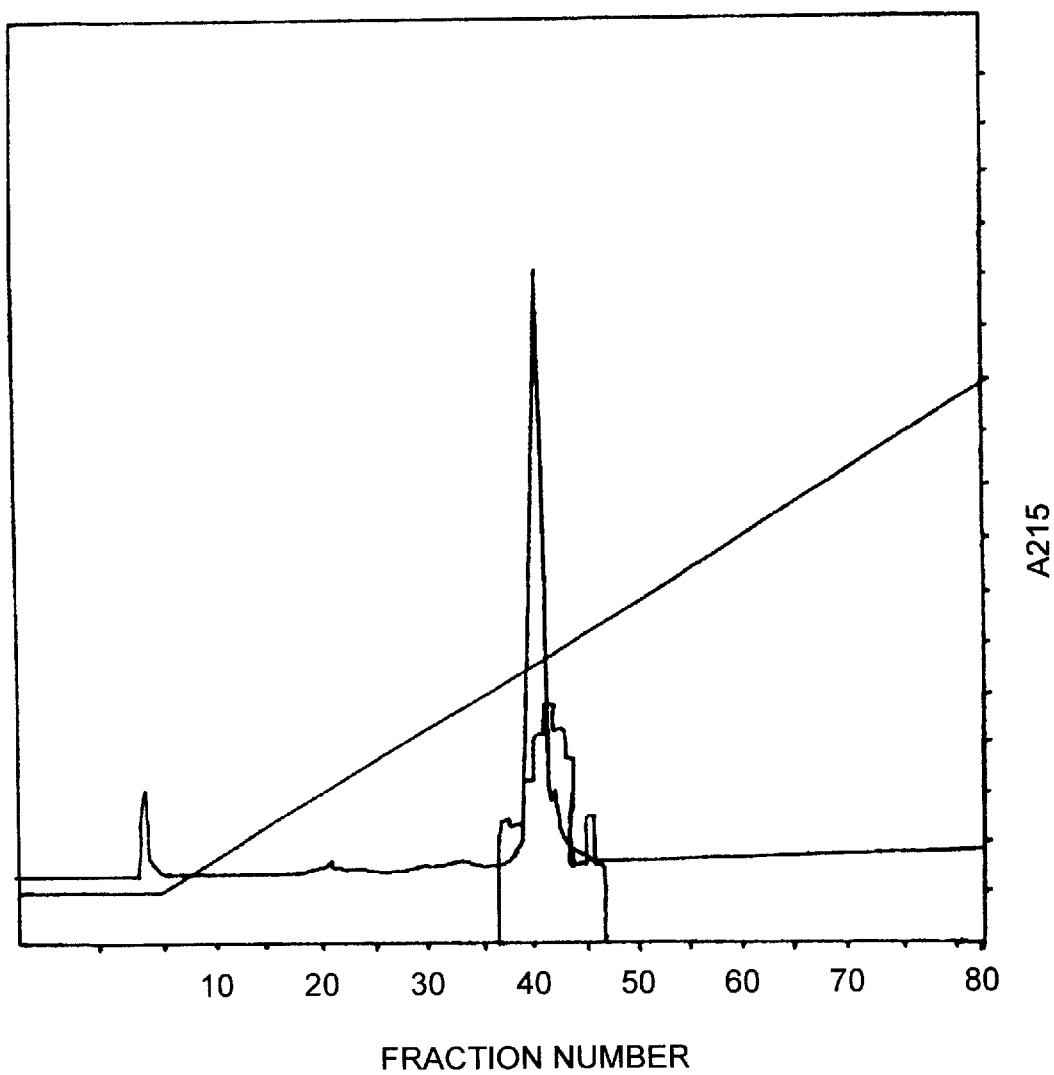
Figure 30:
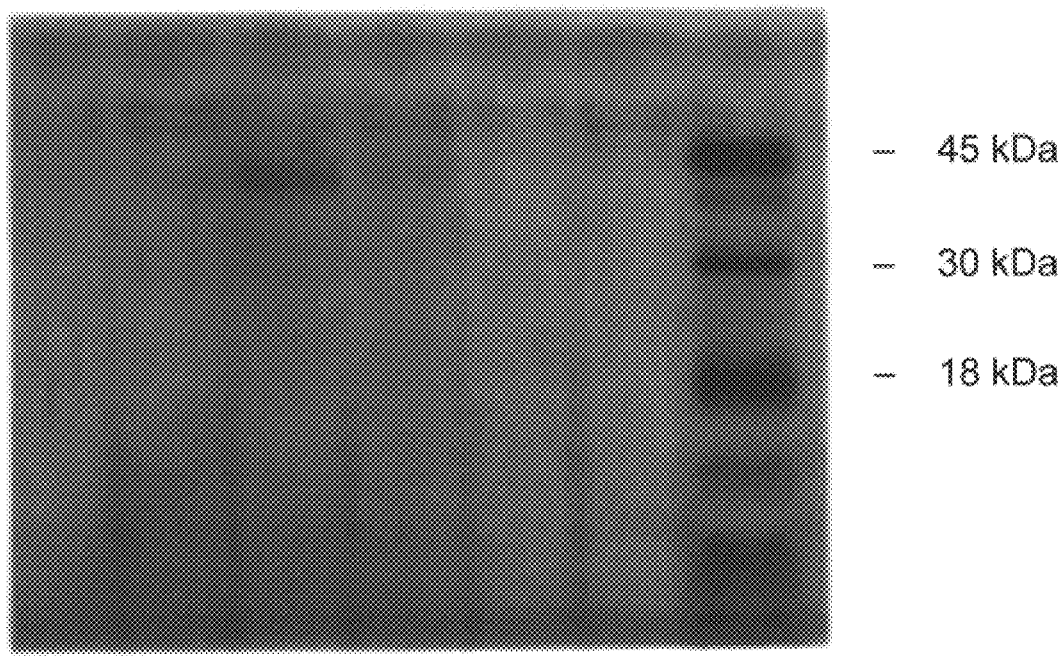

The 24 hour medium (4425 ml) was collected by centrifugation and concentrated by Amicon YM5 filter to about 100 ml. This material was passed through a TNF-affinity gel (0.7×2 cm) at a flow rate of 0.1 ml/min and the gel was washed extensively with 50 mM Tris-HCl pH 7.5. The bound proteins were eluted with 50 mM NaPO$_4$-HCl, pH 2.5 and TNF inhibitor was separated from other contaminating proteins by HPLC-RPC8. As seen in FIG. 27 two TNF-inhibitor peaks are observed. SDS-PAGE analysis of the RPC8 fractions shows that the molecular weights of the two peaks correspond roughly to 30kDa and 40kDa proteins (FIG. 28). The 30kDa protein (TNF-1NH1) was subjected to amino-terminal sequence analysis, and found to be the same sequence as that of urinary 30kDa TNF-inhibitor described above. However, the protein sequence of the 40kDa protein reveals that it is not the same as the 30kDa protein (see Example 11). Further purification of the second TNF inhibitor peak in the human urine, which is seen around fraction 35 in FIG. 8, shows that it is also the 40kDa TNF-inhibitor protein (FIGS. 29 and 30).

The 40kDa TNF inhibitor is also a glycoprotein. This was detected using Concanavalin A-peroxidase after the protein was transferred onto a nitrocellulose filter as described in Example 1.D. The molecular weight of N-glycanase treated 40kDa TNF inhibitor was shown on SDS-PAGE to be about 36kDa. (See procedure described Example 1.D.).

Following the procedures as outlined in Example 1.E. above, it may be determined that the deglycoslyated 40kDa TNF inhibitor also binds to TNF alpha. In addition, the deglycosylated 40kDa protein may also be shown to bind to TNF beta (lymphotoxin).

Example 11

Protein Sequencing of U937 Derived 30kDa TNF Inhibitor, 40kDa TNF Inhibitor, and Urinary 40kDa TNF-Inhibitor Amino terminal sequence of the proteins were determined using Applied Biosystem Protein Sequencer, Model 470.

Both native and reduced-carboxymethylated proteins were sequenced. Approximately 200 pmoles of reverse phase (RP-8) purified TNF inhibitors were applied to a polybrene filter and subjected to automated Edman degradation. The resulting sequence is shown in FIG. 31. It can be seen that the U937-derived 30kDa protein is the same as that formed and identified in urine. The 40kDa TNF inhibitor protein is not the same as the 30kDa TNF inhibitor protein. The urinary 40kDa TNF inhibitor protein does not contain two amino terminal residues; otherwise, it is same as that of the U937-derived 40kDa protein.

Example 12

Primary Structure of the 40kDa TNF Inhibitor

About 40 ug of the reduced and carboxymethylated TNF inhibitor (40kDa) was digested with endoprotease V8 as described above, and the resulting peptides were separated on an RPC18 column (FIG. 32). The peptides purified were sequenced using an Applied Biosystem Protein Sequencer, Model 470.

About 90 ug of the reduced and carboxymethylated TNF inhibitor was treated with 5 ug of endopeptidase Arg-C in 0.2M ammonium bicarbonate at 37° C. After 24 hours of digestion, the Arg-C digested material was loaded onto an HPLC-RP8 column to separate peptides (FIG. 33). Purified peptides were sequenced as before. Some of the peptides were further digested with TPCK-trypsin or chymotrypsin. About 500 pmole of arg-C16 peptide was treated with 3 ug of TPCK-trypsin (Boehringer Mannheim) in 0.2M ammonium bicarbonate at 37° C. for 7 hours, and peptides were separated using RP8 (FIG. 34). About 200 pmole of the peptide arg-C10 was digested with one ug of chymotrypsin (Boehringer Mannheim) at 37° C. for three and a half hours, and the resulting peptides were separated on an RPC18 (FIG. 35).

A partial structure of the TNF inhibitor (40kDa) was determined by aligning various overlapping peptides (FIG. 36). A complete primary structure of the 40kDa TNF inhibitor is shown in FIG. 38. Residues not identified by protein sequencing were deduced by review of the sequence of the cDNA clone that encodes the 40kDa TNF inhibitor and that is discussed in Example 14A and described in FIG. 39.

Example 13

Identification of cDNA Clones for the 40 kDA TNFa Inhibitor

The information presented in Example. 9 shows that U937 cells treated with PMA and PHA produce a TNFa inhibitor with a molecular weight of approximately 40kDa. This protein has been purified and it's amino acid sequence has been substantially determined, as described in Example 12. Table 5 shows the sequences of several peptides derived from this protein and gives the sequences of mixed sequence oligonucleotide probes used to isolate genes coding for the 40kDa TNF inhibitor described here.

The gene encoding sequences comprising the 40kDa inhibitor may be isolated from the human genomic library described in Example 5, or a cDNA library constructed from mRNA obtained from U937 cells that had been treated with PMA and PHA for about 9 hours (See Example 14). Each library should contain approximately 1.0×10⁶ recombinant.

TABLE 5

| Peptide Sequence | Probe Name | Probe Sequence |
|---|---|---|
| EYYDQTA | 40KD-P2' | ``` 5'GAATATTATGATCAAACAGC 3'  C  G C C C G G                    T ``` |
| AQUAFT | 40KD-P1 | ``` 5'GTAAAACGAACTTGAGC 3'  C C   C  G G G C G  T T   T ``` |
| KQEGCR | 40KD-PG | ``` 5'AAACAAGAAGGATGTCG 3'  C  G G G G CAC             T ``` |
| QMCCSKC | 40KD-P5 | ``` 5'CATTTAGAACAACACATTTG 3'  C  C GCTG G    C  T ``` |
| DQTAQMC | 40KD-P6' | ``` 5'GATCAAACAGCACAAATGTG 3'  C C  C G G G G     T T ``` |
| PGWYCA | 40KDP7 | ``` 5' CCAGGATGGTATTGTGC 3'  C C   C C  G G  T T ``` |

Example 14

Isolation of 40kDa TNF Inhibitor cDNA Sequences from PMA/PHA-Induced U937 Cells

U937 mRNA was isolated from cells that had been induced by PMA/PHA for 9 hours. It was then selected on an oligo-dT column, and the polyadenylated mRNA thus isolated was used to make dscDNA using reverse transcriptase followed by E. coli polymerase I/RNase H. The dscDNA was subjected to a polymerase chain reaction using, as primers, the degenerate probes (40KD-P1' and 40KD-P7) shown in Table 5. The DNA products from this reaction were probed on a Southern blot with probe 4OKD-P6' (see Table 5) identifying a single band that contained this sequence. This band was isolated on an agarose gel and cloned into M13 phage DNA (strain mp18). After transformation into E. coli strain JM109 and plating on medium containing X-gal and IPTG, clear plaques were identified that contained the correct cDNA insert. The sequence of the DNA in this clone is shown in FIG. 37 along with the translation product predicted from this sequence. This amino acid sequence matches the peptide sequence shown in FIG. 36 (residues 12–104) and FIG. 38.

Example 14A

Isolation of 40kDa TNF Inhibitor cDNA Clone from PMA/PHA-Induced U937 Cells mRNA was isolated (Chirgwin, J. M. et al., Biochemistry 18, 5294–5299) from human U937 cells that had been exposed to PHA and PMA for 9 hours. mRNA was purified from this RNA using oligo-dT cellulose (Aviv, H. and Leder, P., 1972, Proc. Natl. Acad. Sci. (USA) 69, 1408–1412). 5 ug of this mRNA was used to synthesize 3 ug of blunt-ended, double-stranded cDNA (Gubler, U. and Hoffman, B. J., 1983, Gene 25, 263–269). After addition of EcoRI linkers, the cDNA was purified by sephacryl S-400 (Pharmacia) spun column chromatography and ethanol precipitated. One hundred ng of this cDNA was ligated into 1 ug of EcoRI-digested and alkaline phosphatase-treated lambda gt-10 and packaged in vitro using giga-pack gold (Stratagene). The packaged cDNA yielded 2.5×10⁶ recombinants when plated on E. coli C600 hfl. 1.2×10⁶ members of this library were screened in duplicate with ³²P-labeled probe 40KD-P6+7 (5' GGG CGT ATG TGC TGT CCT CAC AGG 3') as described (Benton, W. D. and Davis, R. W., 1977, Science 196, 180–182). Twelve positive hybridizing clones were isolated and rescreened with probes 40KD-P6' and 40KD-P7 (see Table 5 in Example 13). Four of these clones hybridized to all three probes. One of these clones, c40DK#6, was digested with EcoRI, and a 2.2 kb insert was isolated and subcloned in both orientations into the bacteriophage M13 vector, mp19 (Yarrish-Perron, C., et al., 1985, Gene 33, 103–119). The sequence was determined from both strands using the chain termination method (Sanger, F. and Coulson, A. R., 1975, J. Mol. Biol. 94, 441–448) with Taq DNA polymerase (U.S. Biochemical). This sequence is shown in FIG. 39 along with its deduced translation product. The sequence contains a single open reading frame extending from the is ATG triplet at base 93 that extends well beyond the c-terminal sequence of the 40kDa protein at the GAC triplet at base 863.

Example 15

The 40kDa TNF Inhibitor Inhibits TNF Beta as Well as TNF Alpha

Both the 30kDa TNF inhibitor and the 40kDa TNF inhibitor were examined to determine if they were also capable of inhibiting the activity of TNF beta (lymphotoxin). Various concentrations of TNF-beta (purchased from Endogen) were incubated with each of the inhibitors for one hour at room temperature. The resultant mixtures were analyzed via the L929 cell assay system as described in Example 1.B.1. for TNF alpha. These experiments revealed that the 30kDa TNF inhibitor had little inhibitory effect on TNF beta. However, the 40kDa TNF inhibitor showed significant TNF beta inhibition. The results of these experiments can be seen in FIG. 40.

Example 16

Preparation of Human Genomic DNA Library for 40kDa Inhibitor

An appropriate human genomic DNA library for 40kDa TNF inhibitor may be performed as described in Example 5 for 30kDa TNF inhibitor.

Example 17

Preparation of Genes for the Expression of the 40kDa TNF Inhibitor cDNA in *Escherichia coli*

Portions of the TNF inhibitor (40kDa) cDNA gene coding for soluble TNF binding activities (FIG. 39) have been prepared for expression in *E. coli* as described below.

Because it has been difficult to definitively determine the c-terminal sequence of the mature 40kDa TNF inhibitor derived from urine or U937 cells, we constructed 3 derivatives of its cDNA coding sequence based on sequence analysis of the cDNA clone. The first extends to the putative transmembrane sequence of this protein base pair 863 (FIG. 39) and ends with the peptide sequence . . . Gly Ser Thr Gly Asp. The next two are 51 (Δ51) and 53 (Δ53) amino acids shorter than this clone and end at base pair 710 . . . Ser Pro Thr, and base pair 704 . . . Ser Thr Ser, respectively.

Each of these three C-termini were created by in vitro mutagenesis ("MutaGene", BioRad, Richmond, Calif.) of M13 clones of the cDNA of the 40kDa TNFa inhibitor. The longest clone was created first by use of the following synthetic oligonucleotides:

1. 5' CAC TGG CGA CTA AGC TTC GCT CTT C 3'
2. 5' GCG GCG CAC GCC GGA TCC GAT CTT GGA GGA TGA TTA AAT GTT GCC CGC CCA G 3'

Oligonucleotide 1 inserts a translation termination codon after amino acid 235, Asp, and creates a HindIII restriction endonuclease recognition site at that point. Oligonucleotide 2 adapts the N-Terminal sequence of the mature protein, Leu Pro Ala . . . bp 159 (FIG. 39) for expression in *E. coli* by 1) inserting a Met, ATG codon at amino acid position 1, and 2) inserting a translational coupler sequence and 5' BamHI restriction endonuclease recognition site. The mutagenized fragment was removed by BamHI/HindIII digestion of Rf DNA of the mutant M13 clone and inserted into an *E. coli* expression plasmid as described in Example 7. Clones bearing this gene construction are called TNF.40.

The two shortened clones were constructed as above using the mutagenized M13 derivative of the 40kDa TNFa inhibitor clone isolated above and the following oligonucleotides:

5' GTCCCCCACCTAAGCTTCGGAGTATGG 3' Δ51
5' GTCCACGTCCTAAGCTTCCCACCCGGA 3' Δ53

These two oligonucleotides introduce translation termination codons at bp 710 and 704. respectively (FIG. 39). Clones bearing these gene constructions are called TNF:40 Δ51 and TNF: 40 Δ53 respectively.

Example 18

Expression of Genes Encoding 40kDa TNF Inhibitor in Animal Cells

Expression of the 40kDa TNF inhibitor clone in animal cells may be performed as described in Example 9. The extensive region located 3¹ of the c-terminus of the 40kDa TNF inhibitor may be deleted and a stop codon engineered into the position just following the c-terminal Aspartic acid.

Example 19

Figure 23:
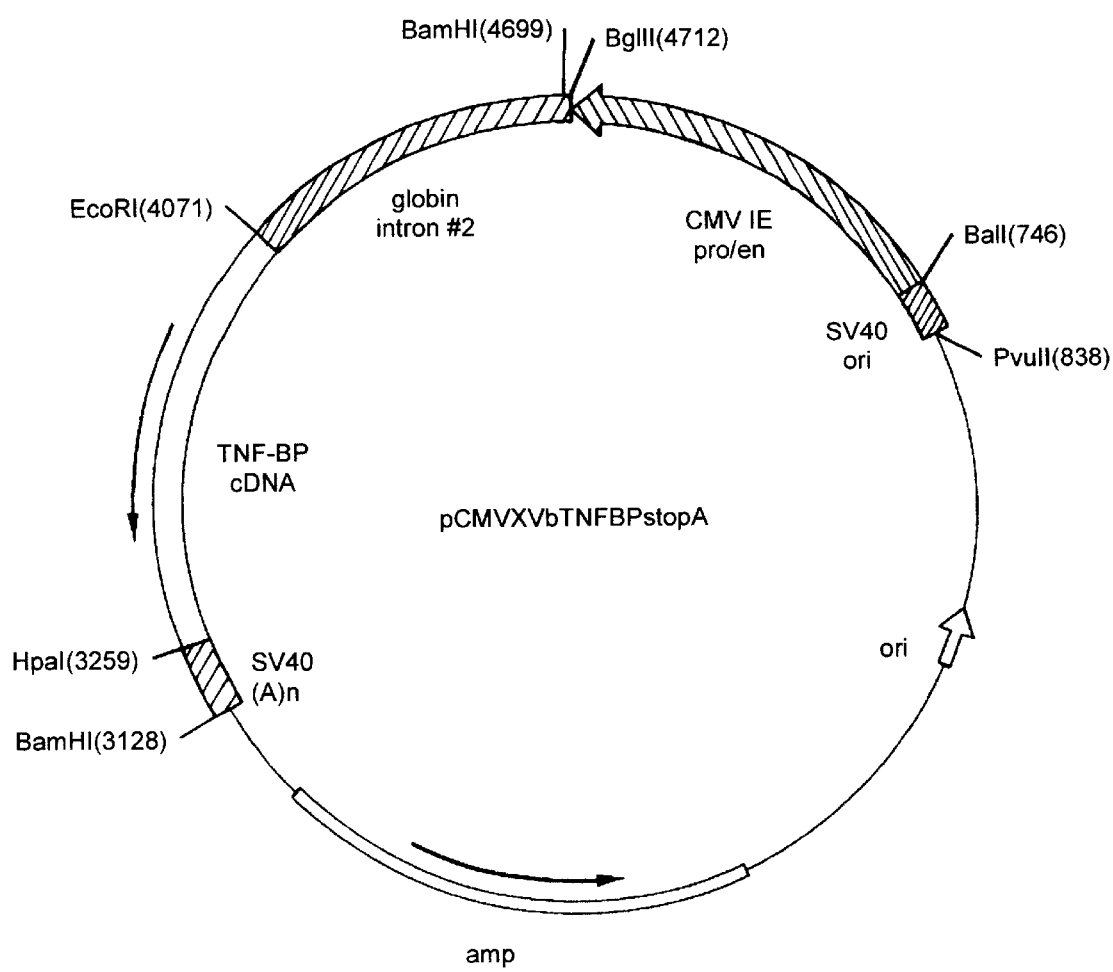

Expression of the Complete cDNA Encoding 30kDa TNF Inhibitor in Mammalian Cells Increases TNF Receptor Sites An expression vector was made that incorporated the entire 30kDa TNF inhibitor cDNA (2.1 kb) shown in FIG. 21, named p30KXVA, and was in all other respects identical to the vector shown in FIG. 23 (i.e., the TNF-BP sequences shown in that figure were replaced by the 2.1 kb cDNA using the unique EcoRI site in the plasmid). See Example 9 for a more complete description of the expression vector. This plasmid was introduced into COS7 cells using the lipofection procedure described by Feigner et al. (Proc. Natl. Acad. Sci. USA, 84, 7413 (1987)). Transfected cells were analyzed for their ability to bind [¹²⁵I]TNFa. FIG. 41 shows the results of the binding assay of cells that were mock-transfected or transfected with the expression vector p30OKXVA. The number of binding sites on plasmid-transfected cells is dramatically higher than the number on the control cells. The complete cDNA clone (i.e., the open reading frame that encodes a much larger protein than the 30kDa urine-derived inhibitor), in fact, represents a cDNA clone of a TNF receptor.

Example 20

Expression of cDNA Encoding 40KDa TNF Inhibitor in Mammalian Cells Increases TNF Receptor Sites An expression vector was made using the 2.4 kb cDNA fragment isolated from the lambda phage page #6 described in Example 14A. This plasmid was identical to that described in Example 9 (FIG. 23) except that the 40kDa TNF inhibitor cDNA sequences were substituted for the 30kDa TNF inhibitor cDNA sequences in that plasmid. Plasmids were isolated with the 2.4 kb EcoRI cDNA fragment in each orientation, named p40KXVA (sense orientation) and p40KXVB (anti-sense orientation). These plasmids contain the SV40 origin of replication, the cytomegalovirus immediate early promoter and enhancer, the rabbit B-globin second intron, the 40KDa TNF inhibitor cDNA, and the SV50 early polyadenylation signal (for a more complete description of this vector, see Example 9) in a pBR322-based plasmid. These plasmids were transfected into COS7 cells which were then assayed for TNF binding (see FIG. 42). Cells transfected with p40KXVA exhibited a higher number of TNF binding sites on the cell surface than either COS7 cells alone or COS7 cells transfected with p40KXVB, suggesting that this cDNA encodes a TNF receptor. Other mammalian cells such as CHO cells could be developed that could overproduce this receptor or that secrete 40KDa TNF inhibitor into the tissue culture medium in ways described in Example 9.

Example 21

Inhibitor Isolated from Human Monocytes

Human monocytes were prepared from 550 ml of blood as described by (Hannum, C. H. et al. Nature 343, 336–340, 1990). The fresh monocytes ($2\times10^7$ cells) were seeded in 500 ml of serum free RPMI1640 medium and treated with 10 ng/ml of PMA and 5ug/ml of PHA-P for 24, 48 and 72 hours at 37° C. After the incubation, the media were collected by centrifugation and concentrated to 50 ml. The concentrated media were loaded onto a TNF-affinity column (2 ml bed volume) one sample at a time and eluted with acid as in Example 1. The eluted material was further purified using a HPLC RPC-8 column under the same conditions as in Example 1, and each fraction was assayed with L929 cytoxicity assay. FIG. 43 shows the two peaks of TNF inhibition activity. These two peaks correspond to the 30kDa and 40kDa TNF inhibitors which were also found in the culture medium of U937 cells that was treated with PMA and PHA and identified in urine.

Example 22

Expression and Purification of Shorter Forms of the 40kDa TNF Inhibitor (Δ51 and Δ53) from E. coli.

Cells(300 ml of E. coli cultures (40kDa TNF inhibitor Δ51 and 40kDa TNF inhibitor Δ53)) grown separately under induced condition for 2 hours were resuspended in 10 ml of 50 mM Tris-HCl, pH 7.5 containing 2 mM EDTA (TE buffer) and French pressed at 20,000 G for 10 min. The resulting pellets were washed once with TE buffer. The washed pellet was resuspended in 2 ml of 6M Guanidine-HCl 100 mM Tris-HCl, pH8.5/4 mM PMSF, and incubated at room temperature for one hour. After incubation, 500 mM DTT was added to a final concentration of 4 mM, and the mixture was incubated at room temperature for another hour. Insoluble material was removed by centrifugation at 20,000G for 15 min. 500 mM oxidized glutathione was added to the supernatant to a final concentration of 2 mM, and the mixture was incubated at room temperature for 10 min. This material was then diluted in 20 ml of 0.6% Tris base solution with 5 mM cysteine. PMSF was added to a final concentration of 2 mM. After 16 hours of incubation at 4° C., this material was dialyzed against 300 volumes of 50 mM Tris-HCl, pH 7.5 for 3 hours at 4° C., then centrifuged at 20,000 G for 15 min. The supernatant was loaded onto a TNF-affinity column (.7×2 cm, 13 mg rhTNF/ml of affigel-10) at a flow rate of 0.09 ml per min. This column was extensively washed with 50 mM Tris-HCl, pH 7.5. The bound proteins were eluted with 50 mM NaH2PO4-HCl, pH 2.5. The acidic eluates were loaded onto an RP8 column (2×200 mm, spelco) and the TNF inhibitors were eluted with a linear gradient of acetonitrile in 0.1% TFA at a flow rate of 1 ml per gradient per min. (FIG. 44A and 45A). Fractions were examined by L929 cytotoxicity assay to localize the TNF inhibitors. The major peak on each RP8 profile contains the TNF-inhibiting activity (FIG. 44C and 45C). The E. coli-produced TNF-inhibitors (40kDa TNF inhibitors Δ53 and 40kDa TNF inhibitors Δ51) migrate to the expected location on SDS-PAGE (FIG. 44B and 45B). The amino terminal sequence of these materials shows that the E. coli-produced TNF-inhibitors have the following sequence:

Met-Leu-Pro-Ala-Gln-Val-Ala-Phe-Thr-Pro-Tyr-Ala-Pro-Glu

By using this procedure, about 150ug of each 40kDa TNF inhibitor (Δ51 and Δ53) was obtained from 30 ml of the culture. The yield was a few percent, however, the yield can be increased to over 30% by improving each step of this purification.

Both of these 40kDa TNF inhibitors (Δ51 and Δ53) inhibit not only TNF-alpha but also TNF-beta.

Example 23

Expression and Purification of Full Length 40kDa TNF Inhibitor

An active 40kDa TNF inhibitor was purified from an E. coli strain carrying plasmids which have a gene for full length mature 40kDa TNF inhibitor (as in Example 12). The method used to isolate an active inhibitor was the same as that of example 22. This active inhibitor inhibits both TNF-alpha and TNF-beta, and the amino terminal sequence is same as shown in Example 22.

Example 24

Amino Acid Composition of the 40kDa TNF Inhibitor

U937-produced mature 40kDa TNF inhibitor was analyzed for total amino acid composition by the PTC-amino acid analysis system. The actual and predicted composition data for full length mature 40kDa TNF inhibitor as shown in FIG. 38 are shown in Table 6.

Example 25

Production of Chemically Modified TNF Inhibitors

In order to increase the half-life of the TNF inhibitors in plasma, TNF inhibitors which are chemically modified with polyethylene glycol (PEG) may be made. The modification may be done by cross linking PEG to a cysteine residue of the TNF inhibitor molecules. Since all of the cysteine residues in the TNF inhibitors form disulfide bonds, mutant TNF inhibitors may be constructed which contain an extra cysteine residue at the amino terminus, glycosylation sites, and the carboxyl terminus of each inhibitor. The mutagenesis may be carried out by PCR using oligonucleotides containing the desired mutation. As for the 30kDa TNF inhibitor, an extra cysteine residue was added at residue number 1, 14 or 105. These mutant proteins were expressed in *E. coli* by using the same system described in Examples.7, 22 and 23, and refolded to active TNF inhibitor. The mutant proteins are as active as the non-mutated proteins. Pegylation of these proteins will be carried out, and the activity will be assessed. The 40kDa mutants will be constructed as above and pegylation will be performed to obtain active proteins and will have increased the stability of the TNF inhibitor.

It is to be understood that the application of the teachings of the present invention to a specific expression system will be within the capabilities of one having ordinary skill in the art in light of the teachings contained herein. Thus, it will be apparent to those of ordinary skill in the art that various modifications and variations can be made in the processes and products of the present invention. It is intended that the present invention covers these modifications and variations provided they come within the scope of the appended claims and their equivalents.

TABLE 6

| | Calculated # by DNA sequence | Experimental # |
|---|---|---|
| Asx | 14 | 13.0 |
| Glx | 23 | 22.6 |
| Ser | 25 | 23.2 |
| Gly | 14 | 17.8 |
| His | 4 | 4.5 |
| Thr | 26 | 23.9 |
| Ala | 17 | 17 |
| Arg | 14 | 15.1 |
| Pro | 26 | 22.3 |
| Val | 13 | 8.7 |
| Ile | 4 | 3.4 |
| Leu | 10 | 8.6 |
| Phe | 5 | 4.6 |
| Lys | 6 | 5.4 |
| Tyr | 5 | 5.0 |
| Trp | 3 | ND |
| Met | 3 | ND |
| Cys | 22 | ND |

ND: not determined.

What is claimed is:

1. An isolated nucleic acid comprising a nucleotide sequence that encodes a polypeptide having TNF inhibitory activity, wherein the polypeptide has an amino acid sequence as shown in FIG. 20 or a fragment thereof, but that has at least one non-native cysteine residue at the N-terminus, C-terminus, residue 14, or residue 105.

2. The nucleic acid of claim 1, wherein said cysteine residue in said TNF inhibitor is at residue 105.

* * * * *

UNITED STATES PATENT AND TRADEMARK OFFICE
CERTIFICATE OF CORRECTION

PATENT NO.   : 6,541,620 B1
DATED        : April 1, 2003
INVENTOR(S)  : Michael T. Brewer, Robert C. Thompson and Tadahiko Kohno It is certified that error appears in the above-identified patent and that said Letters Patent is hereby corrected as shown below:

Title page,
Item [57], ABSTRACT, delete "30kDa" before "TNF inhibitor or a fragment thereof";

Column 5,
Line 48, delete "Δ51A," and insert therefor -- Δ51 (A), --;

Column 8,
Line 13, delete "a Δ51" and insert therefor -- Δ51 --;

Column 19,
Line 3, delete "intone" and insert therefor -- in one --;

Column 23,
Line 60, delete "TNF-aff igel" and insert therefor -- TNF-affigel --;

Column 24,
Lines 18 and 19, delete "40° C." and insert therefor -- 4° C. --;

Column 29,
Line 61, delete "tacd" and insert therefor --tacI --;

Column 36,
Line 64, delete "p30OKXVA" and insert therefor -- p30KXVA --;

Column 38,
Line 10, delete "2 mM" and insert therefor -- 20 mM --.

Signed and Sealed this

Twenty-third Day of September, 2003

JAMES E. ROGAN
*Director of the United States Patent and Trademark Office*